United States Patent
Peterka et al.

(10) Patent No.: US 8,224,669 B2
(45) Date of Patent: Jul. 17, 2012

(54) CHRONIC DISEASE MANAGEMENT SYSTEM

(75) Inventors: Bruce A. Peterka, Milwaukee, WI (US); Reginald M. Hislop, III, Mukwonago, WI (US); Brian Hand, Waukesha, WI (US)

(73) Assignee: Anchor Holdings, Inc., West Allis, WI (US)

( * ) Notice: Subject to any disclaimer, the term of this patent is extended or adjusted under 35 U.S.C. 154(b) by 2784 days.

(21) Appl. No.: 10/882,606

(22) Filed: Jul. 1, 2004

(65) Prior Publication Data

US 2006/0004603 A1   Jan. 5, 2006

(51) Int. Cl.
G06Q 10/00 (2012.01)
G06Q 50/00 (2012.01)

(52) U.S. Cl. .............................................. 705/3; 705/2
(58) Field of Classification Search .................. 705/2–4
See application file for complete search history.

(56) References Cited

U.S. PATENT DOCUMENTS

| | | | |
|---|---|---|---|
| 4,803,625 A | 2/1989 | Fu et al. | |
| 4,951,197 A * | 8/1990 | Mellinger ..................... | 600/300 |
| 5,307,263 A | 4/1994 | Brown | |
| 5,331,549 A | 7/1994 | Crawford, Jr. | |
| 5,357,427 A | 10/1994 | Langen et al. | |
| 5,822,715 A | 10/1998 | Worthington et al. | |
| 5,832,448 A | 11/1998 | Brown | |
| 5,897,493 A | 4/1999 | Brown | |
| 5,960,403 A | 9/1999 | Brown | |
| 5,997,476 A | 12/1999 | Brown | |
| 6,018,713 A * | 1/2000 | Coli et al. .......................... | 705/2 |
| 6,039,688 A * | 3/2000 | Douglas et al. ............... | 600/300 |
| 6,101,478 A | 8/2000 | Brown | |
| 6,168,563 B1 | 1/2001 | Brown | |
| 6,246,992 B1 | 6/2001 | Brown | |
| 6,248,065 B1 | 6/2001 | Brown | |
| 6,277,071 B1 * | 8/2001 | Hennessy et al. ............. | 600/300 |
| 6,368,273 B1 | 4/2002 | Brown | |
| 6,379,301 B1 | 4/2002 | Worthington et al. | |
| 6,381,577 B1 * | 4/2002 | Brown .............................. | 705/2 |
| 6,409,662 B1 | 6/2002 | Lloyd et al. | |
| 6,443,890 B1 | 9/2002 | Schulze et al. | |
| 6,497,657 B2 | 12/2002 | Nunome | |
| 6,513,532 B2 * | 2/2003 | Mault et al. ................... | 600/595 |
| 6,551,243 B2 | 4/2003 | Bocionek et al. | |
| 6,714,894 B1 * | 3/2004 | Tobey et al. ................... | 702/188 |
| 7,062,220 B2 * | 6/2006 | Haynes et al. ................. | 434/353 |

(Continued)

OTHER PUBLICATIONS iMetrikus; "MediCompass serving healthcare consumers and professionals"; iMetrikus Capabilities Overview Diabetes Care.

(Continued)

Primary Examiner — Robert Morgan
Assistant Examiner — Anita Molina
(74) Attorney, Agent, or Firm — Drinker Biddle & Reath LLP

(57) ABSTRACT

A health care management system and method for chronic disease management such as diabetes management, hypertension management and like chronic diseases. The system is utilized by both patients and clinicians to manage the patients' chronic diseases and for clinicians to better manage a population of patients.

9 Claims, 55 Drawing Sheets

U.S. PATENT DOCUMENTS

| | | |
|---|---|---|
| 2001/0037060 A1 | 11/2001 | Thompson et al. |
| 2001/0037217 A1 | 11/2001 | Abensour et al. |
| 2002/0068858 A1 | 6/2002 | Braig et al. |
| 2002/0072933 A1 | 6/2002 | Vonk et al. |
| 2003/0009088 A1 | 1/2003 | Korth et al. |
| 2003/0036683 A1 | 2/2003 | Kehr et al. |
| 2003/0040821 A1 | 2/2003 | Case |
| 2003/0072424 A1 | 4/2003 | Evans et al. |
| 2003/0093301 A1 | 5/2003 | Chesney et al. |
| 2003/0144874 A1 | 7/2003 | Barret et al. |
| 2003/0159030 A1 | 8/2003 | Evans |

OTHER PUBLICATIONS

Health Hero Network; Health Hero Press Releases; "Financial Times Cites Health Hero Network Among Leaders in Patent Race"; http://www.healthhero.com/press/press_releases/pr_06_12_03.html; Jun. 12, 2003.

Health Hero Network; Health Hero Press Releases; "Health Hero Network Files Fundamental Patent Application Covering Its Technology Platform"; http://www.healthhero.com/press/press_releases/pr_08_28_03.html; Aug. 28, 2003.

* cited by examiner

| Food Group | Assigned Units | My Plan Units | Select | My Food! |
|---|---|---|---|---|
| Starch | 4 | 0 | | |
| Meat/Protein | 7 | 0 | | |
| Vegetable | 13 | 0 | | |
| Fruit | 19 | 0 | | |
| Milk | 25 | 0 | | |
| Fat | 31 | 0 | | |
| Sweets | 99 | 0 | | |

Education, Assigned Chapters

| Chapter | Assign Date | End Date | Trainer | Training Type | View Chapter |
|---|---|---|---|---|---|
| Alcohol and Diabetes | 04/12/2004 | | Thomas, Julie | Individual | View Chapter |
| Working with Your Health Care Team | 04/21/2004 | | Bedi, Kabir | Individual | View Chapter |
| Choosing Food | 05/11/2004 | | Hand, Brian | Individual | View Chapter |
| What's In Food? | 05/15/2004 | | Hand, Brian | Individual | View Chapter |
| Sugar and Fat Substitutes | 05/13/2004 | | Hand, Brian | Individual | View Chapter |
| Taking Charge of Your Meal Plan | 05/13/2004 | | Hand, Brian | Individual | View Chapter |
| Physical Activity | 05/12/2004 | | Hand, Brian | Group | View Chapter |

Fig. 13

Alcohol and Diabetes

Overview

This module provides participants with information about the use of alcohol. Several factors need to be considered by people with diabetes when deciding whether or not to drink alcoholic beverage; including personal desires and beliefs and the effect of alcohol on blood sugar, weight, lipid levels, nerves, and medications. Guidelines for alcohol use and ways to include alcohol in the meal plan are discussed.

Alcohol is a subject that participants may be reluctant to bring up. The health professional needs to inquire in a nonjudgmental way about the use of alcohol so that this subject can be adequately addressed. Although alcohol may be contraindicated for some people, it can be safely included in the diet of many participants if certain guidelines are followed.

Objectives

CHRONIC DISEASE MANAGEMENT SYSTEM

BACKGROUND OF THE INVENTION

Currently, the health care industry finds challenges in managing chronic diseases such as diabetes and hypertension due to a lack of real time patient monitoring as well as a lack of patient education relating to the chronic diseases. Patients not properly monitored can reach critical levels and become seriously ill. Increased medical and insurance costs are direct results.

BRIEF DESCRIPTION OF THE DRAWINGS

FIG. 9 is a screen in a Customized Diet Plan section of the Diet category.

FIG. 12 is a screen in the My Meal Plan Today section.

FIG. 13 is a screen in the Education category in the PRS.

FIG. 14 is a screen in the Education category.

FIG. 17 is a screen in an Exercise Entry section in the Exercise category.

FIG. 18 is a screen in an Exercise Plan section of the Exercise category.

FIG. 24 is a diabetes education screen in an Education group in the CMS.

FIG. 25 is a personal data screen in a General Information group in the CMS.

FIG. 26 is a diabetes information screen in a Medical/Health group in the CMS.

FIG. 33 is a patient group screen in the General Information group.

FIG. 35 is a group education assignment screen in the Education group.

FIG. 36 is an assign group education screen in the Education group.

DETAILED DESCRIPTION

The invention includes a health care management system and method for chronic disease management such as diabetes management, hypertension management and like chronic diseases. The system and method are utilized by both patients and clinicians to manage patients' chronic disease and for clinicians to manage a population of patients. Hereafter, the chronic disease discussed with reference to the described embodiment is diabetes but it should be noted that the system is equally applicable to other chronic diseases.

The following terms shall be used as follows. An entity is a health care organization that uses the system. An entity can have one or more facilities. A facility is a hospital, clinic, treatment center, etc. related to an entity. A clinician can work at different facilities within an entity as well as at different facilities among different entities. A patient can be treated at different facilities within an entity as well as at different facilities among different entities.

Figure 1A:
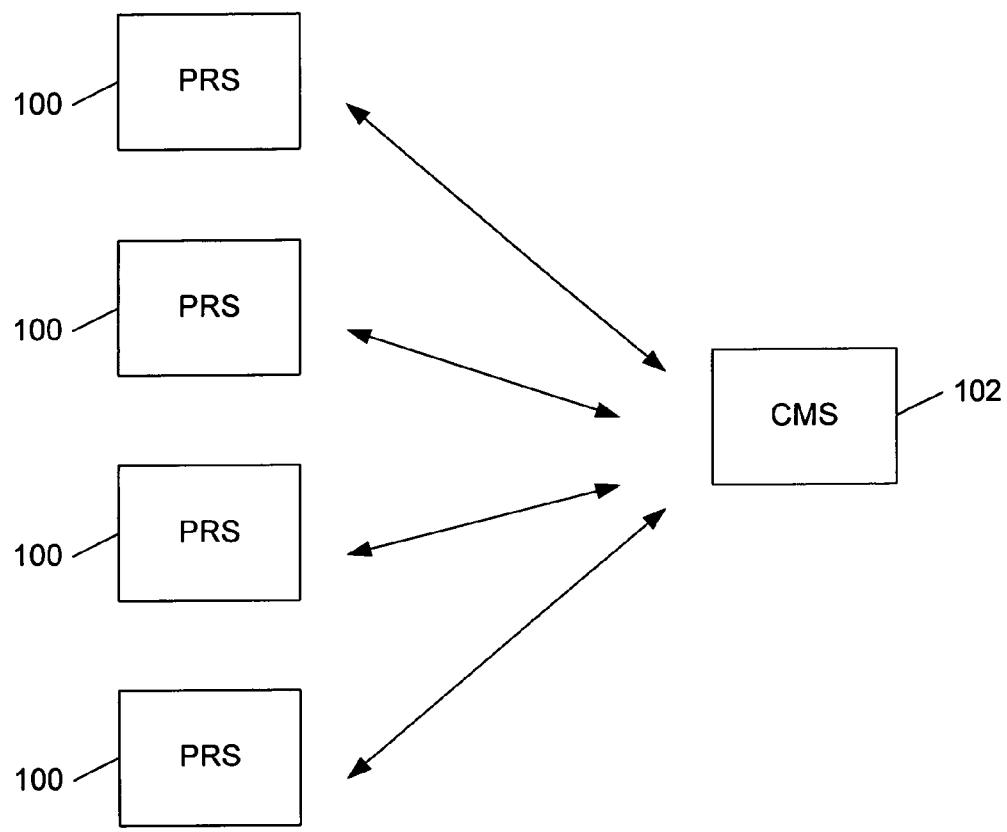
FIGS. 1A and 1B are schematics of embodiments of a system including a clinical medical system (CMS) and a plurality of patient residence systems (PRS).
Figure 1B:
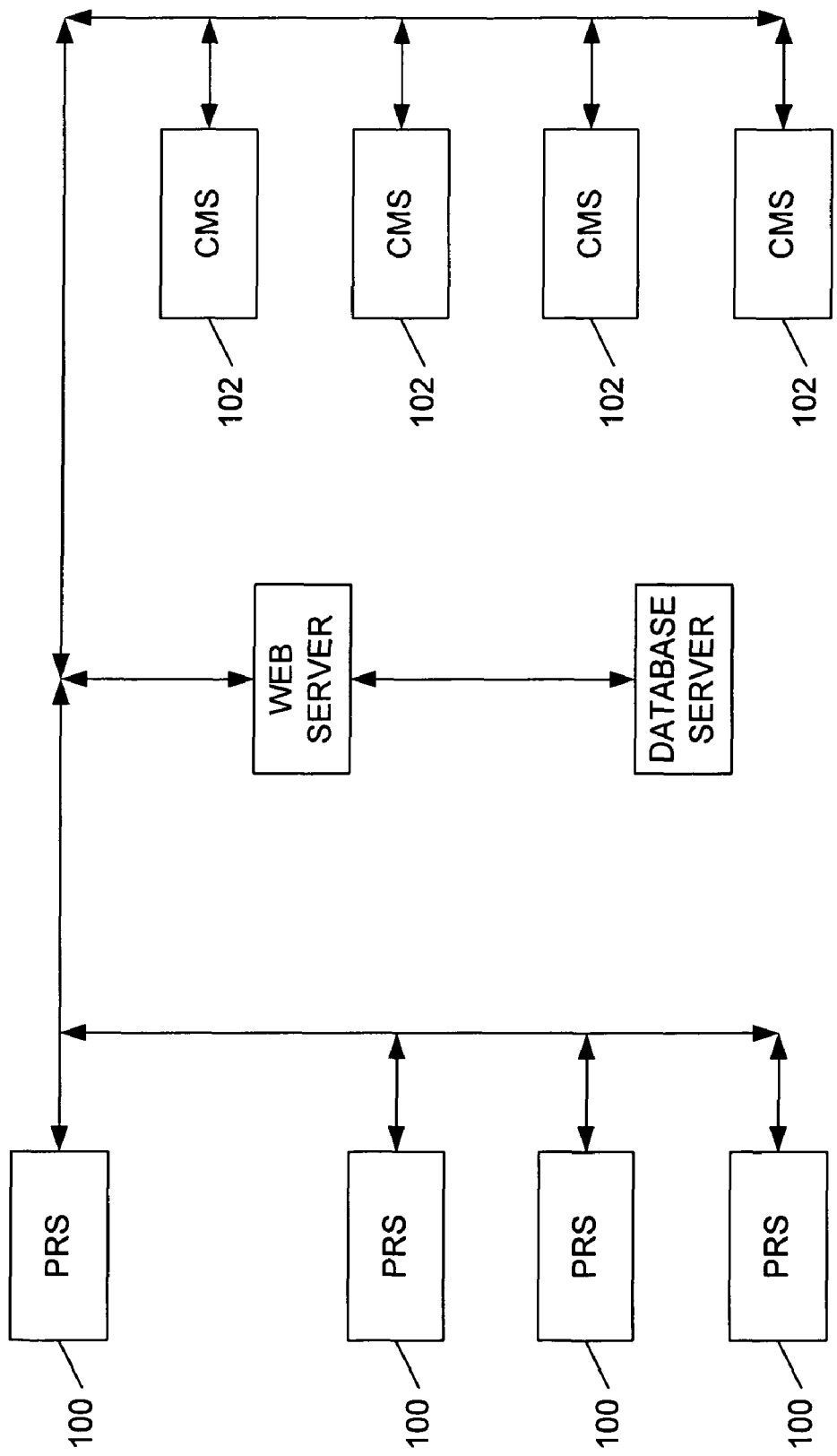

As set forth in FIGS. 1A and 1B, the system consists of two components; a component for patient use termed the patient residence system (PRS) 100 and a component for administrators, clinicians, data entry personnel and trainers termed the clinical medical system (CMS) 102. The terms PRS and CMS will be used throughout for referencing each component and should not be considered limiting.

Patient Residence System (PRS)

The PRS 100 is installed at a patient's residence or other appropriate location. The PRS allows an individual patient to view their medical information, their educational assignment and progress, their diet and their exercise habits, and to upload their biological readings. Specifically with respect to diabetes education, education through the PRS provides information on diets, exercises and identification of warning signs. The PRS provides an educational experience through a published knowledge base on diabetes and provides an interactive educational experience. When clinicians can monitor the educational progress of patients, this helps identify which patients need more help in understanding the subject. Use of the PRS 100 enables a patient to receive immediate care if a patient is showing warning signs.

Figure 2:
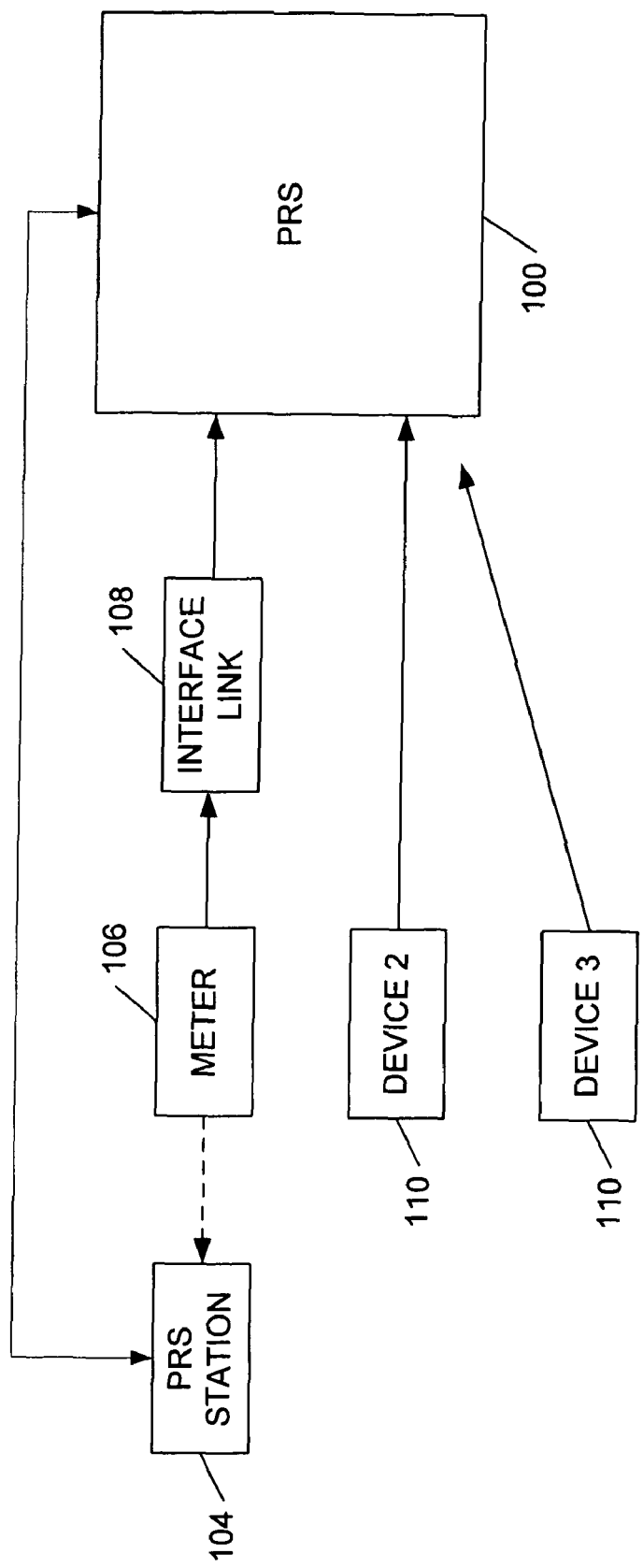
FIG. 2 is a schematic of the PRS and a PRS station.

With reference to FIG. 2, the PRS 100 is in communication with a PRS station 104 such as a computing device, preferably a touch screen monitor. A patient can have multiple PRS stations, for example, in multiple residences. A conventional glucose meter 106 used by the patient to take daily glucose readings can be put in communication with the PRS 100 via the PRS station 104 (as shown in dashed lines) or via an interface link 108 such as the MetrikLink device available from iMetrikus of Carlsbad, Calif. Other devices 110 for taking biological measurements can also be put in communication with PRS 100 such as blood pressure devices, scales, thermometers, and the like. The patient can also enter data manually into the PRS station 104. All of the biological data is sent to the PRS 100 for processing. Preferably, the PRS 100 is a completely web based system and all information viewed from the PRS 100 resides on the same database as the CMS 102.

Figure 3:
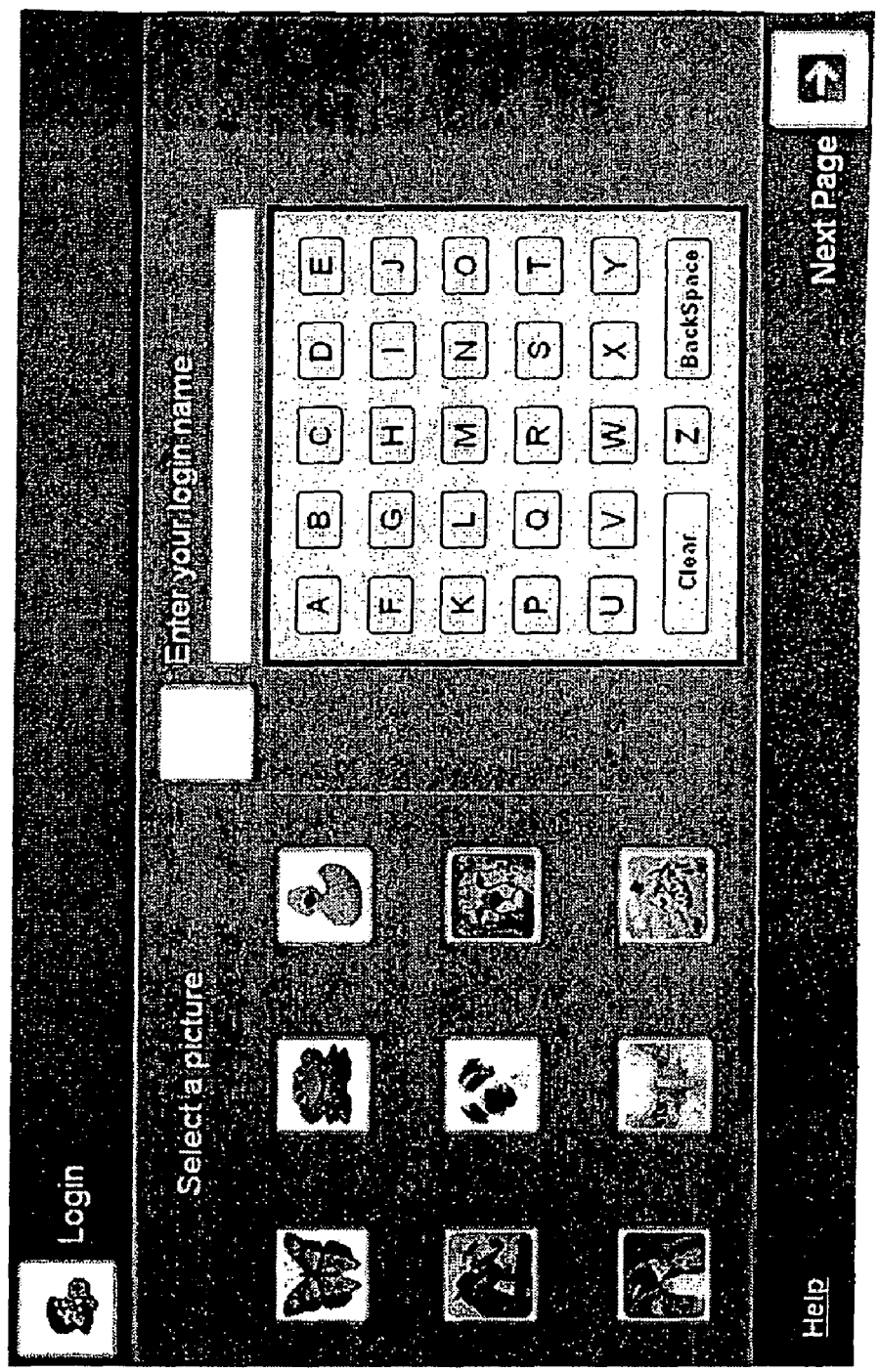
FIG. 3 is a patient login screen in the PRS.
Figure 4:
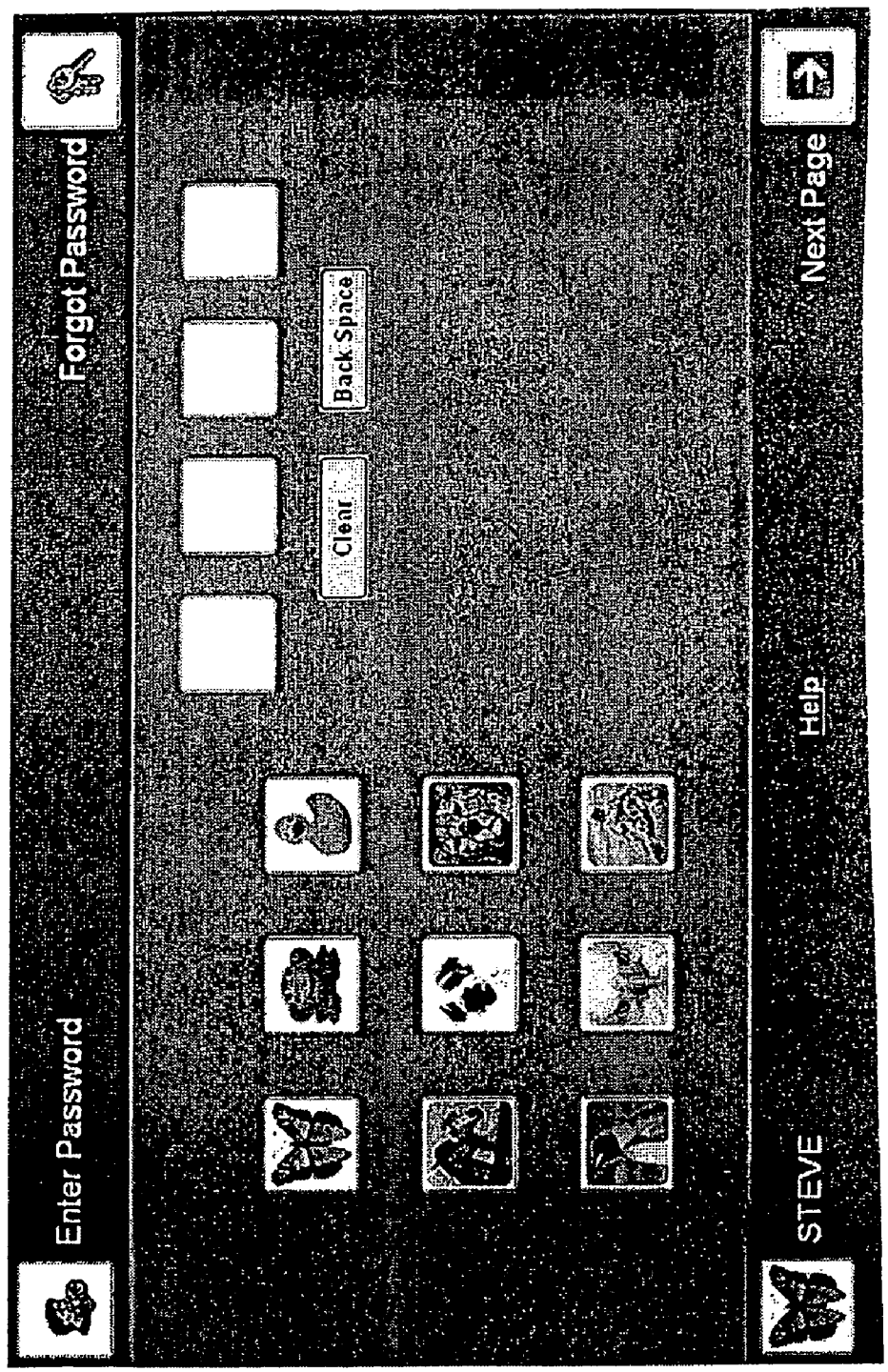
FIG. 4 is a patient login screen in the PRS.

To access the PRS and with reference to FIGS. 3 and 4, a patient logs onto the PRS station 104 using a user name and password. Preferably, and as shown in FIG. 3, the patient selects a picture then, optionally, types in a user name by pressing on the keypad. Patient logon can be accomplished by other means such as card readers, voice recognition, and the like. Thereafter, and as shown in FIG. 4, the patient enters a password by selecting four of the pictures. If the patient forgets their password, they are able to send a message to the CMS 102 to receive a new password.

Figure 5:
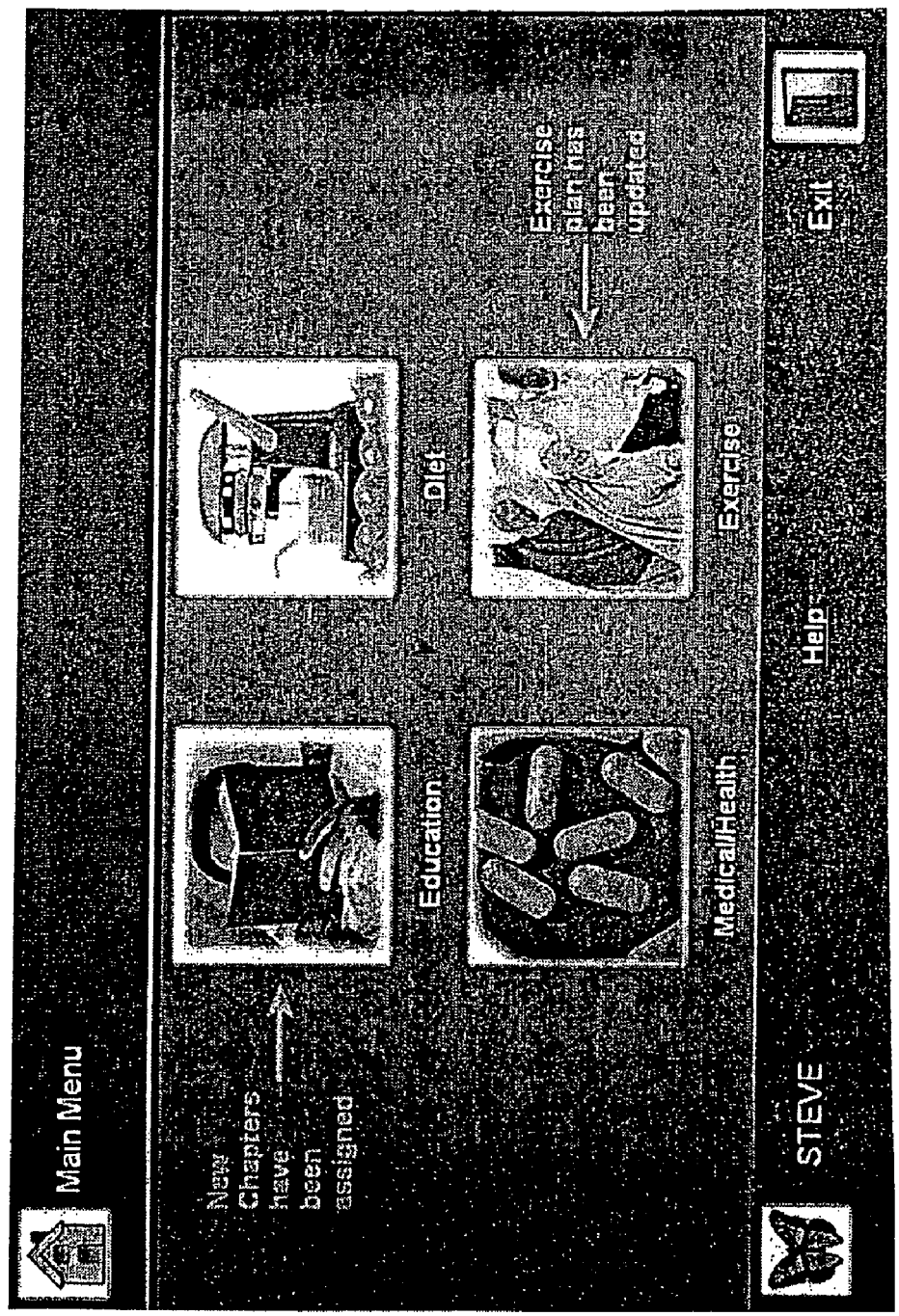
FIG. 5 is a main menu screen in the PRS.

Turning now to the sample screen at FIG. 5, upon login, the patient is directed to a main menu, has a choice of viewing information relating to Medical/Health, Diet, Education and Exercise, and is altered to new information such as the "New Chapters have been assigned" message and the "Exercise plan has been updated" message, for example. The patient selects one of these categories by pressing on its associated icon.

Figure 6:
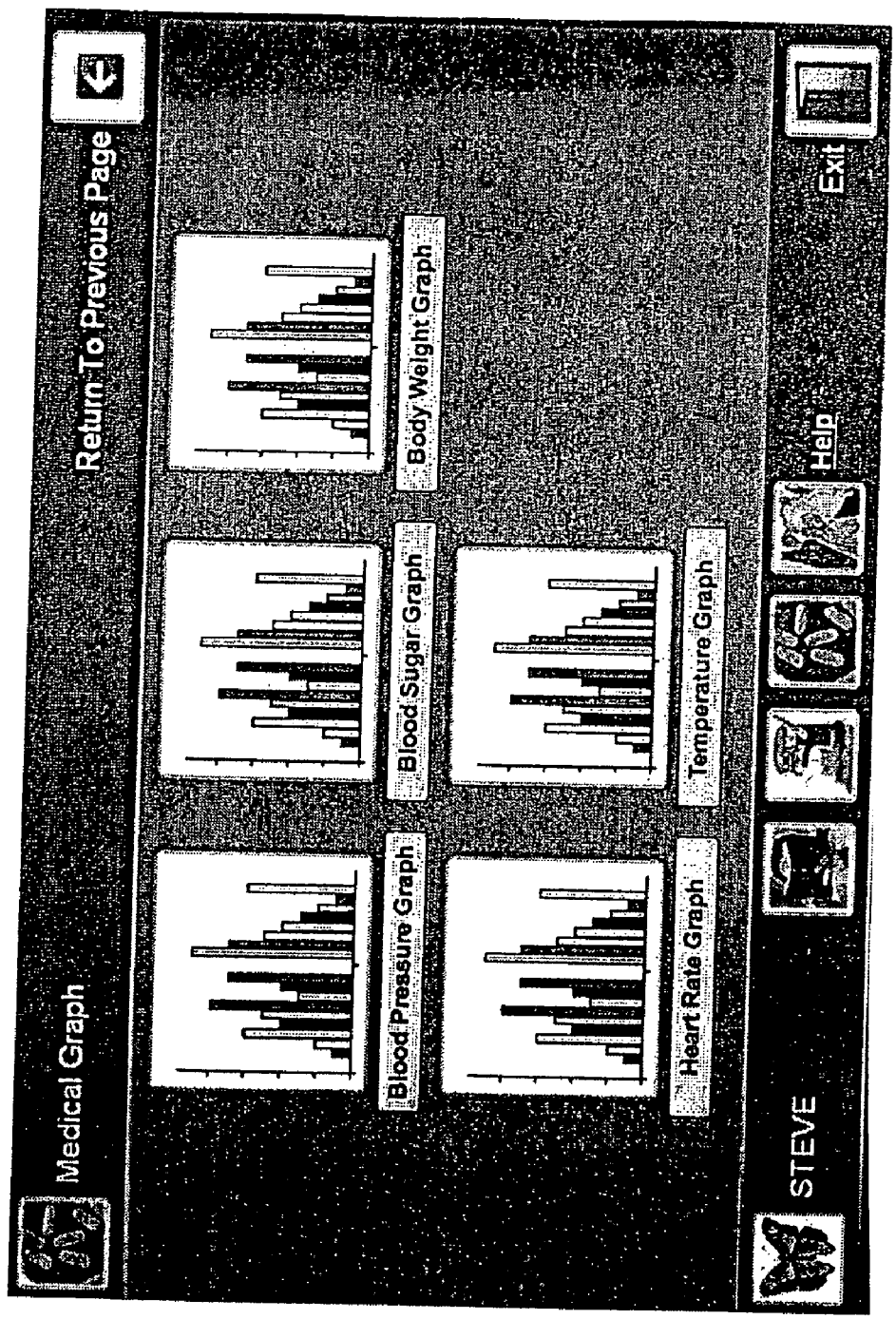
FIG. 6 is a menu screen in a Medical/Health category in the PRS.
Figure 7:
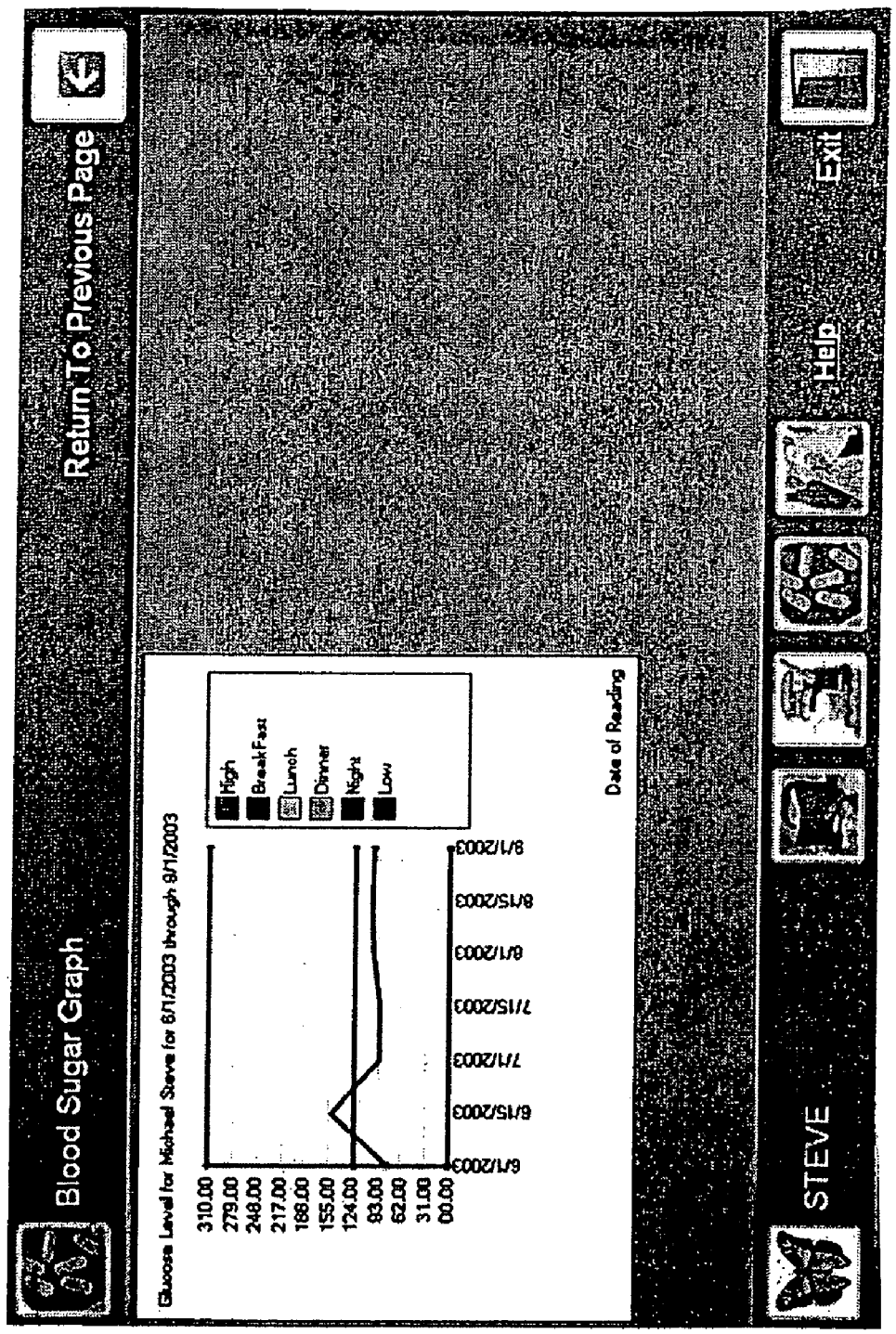
FIG. 7 is a glucose level graph screen in the Medical/Health category.

Medical/Health. The Medical/Health category pertains to the medical and health aspects of a patient's disease and specifically enables a patient to view his/her biological readings, preferably in chart format. As set forth on FIG. 6, there is illustrated the five charts of blood pressure, blood sugar, body weight, heart rate and temperature. The patient can click on any one of charts for a more detailed view, as is set forth on FIG. 7 for blood sugar. Preferably, the data shown comes from the devices attached to the PRS 100 in that it is validated data. Alternatively, the patient can enter biological reading data manually by kind, date and time into the PRS for analysis by a clinician accessing the CMS. The Medical/Health category includes information on skin wounds. The patient has the ability to enter data relating to skin wounds in fields such as date, body location, odor, drainage, pain level, pain description and color and the ability to upload a photograph of the wound into the PRS for analysis by a clinician accessing the CMS.

Figure 8:
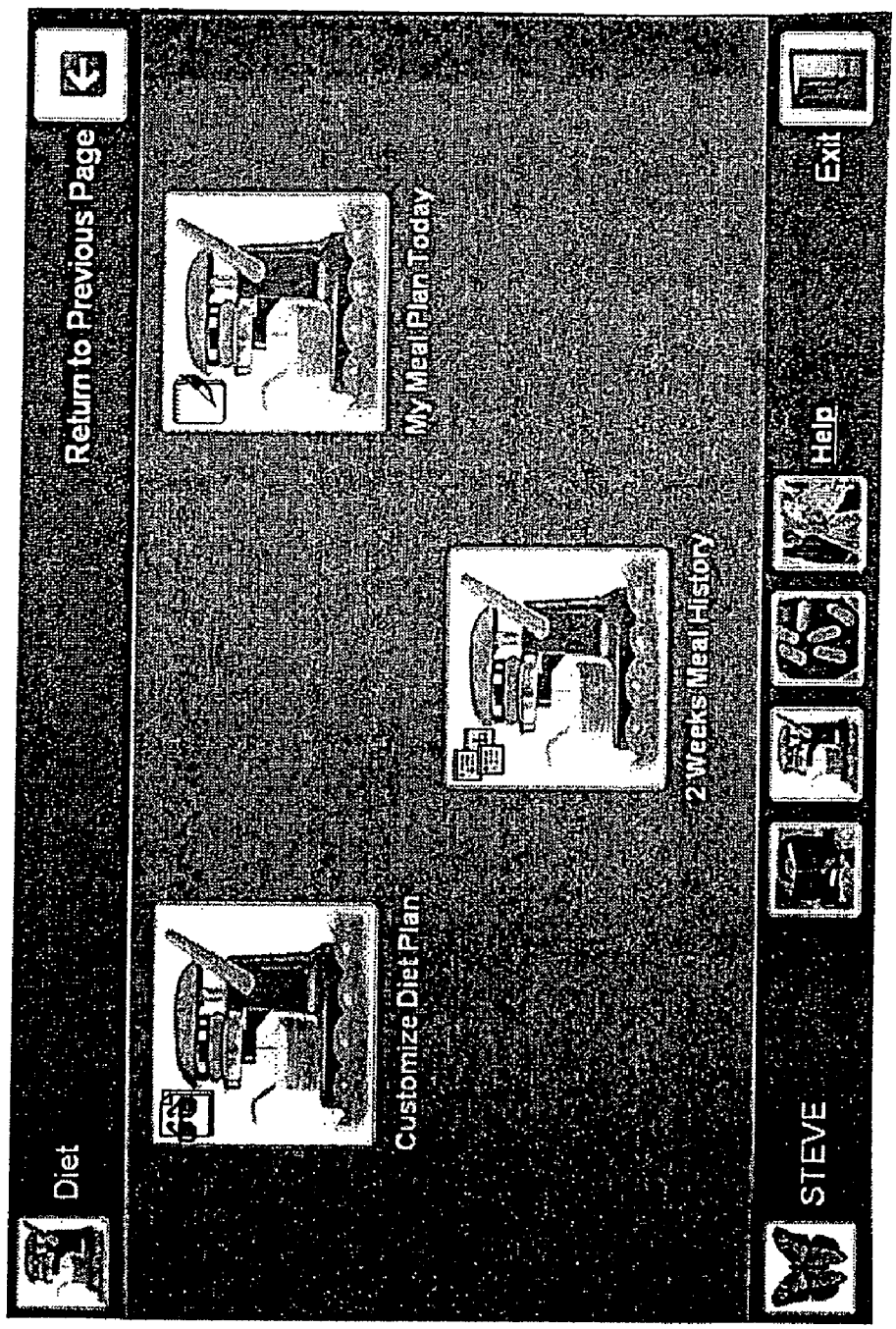
FIG. 8 is a menu screen in a Diet category in the PRS.
Figure 10:
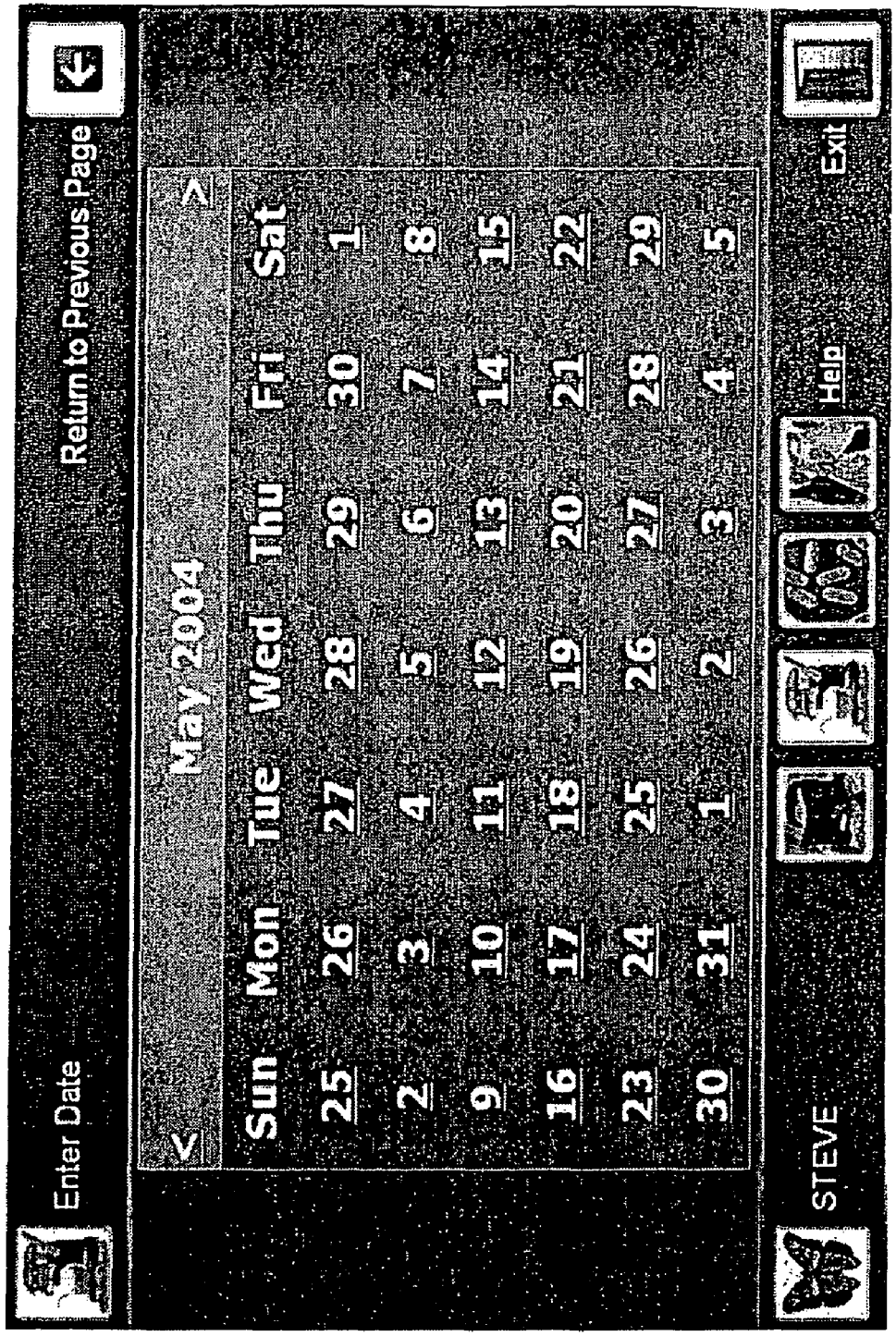
FIG. 10 is a calendar screen in a My Meal Plan Today section of the Diet category.
Figure 11:
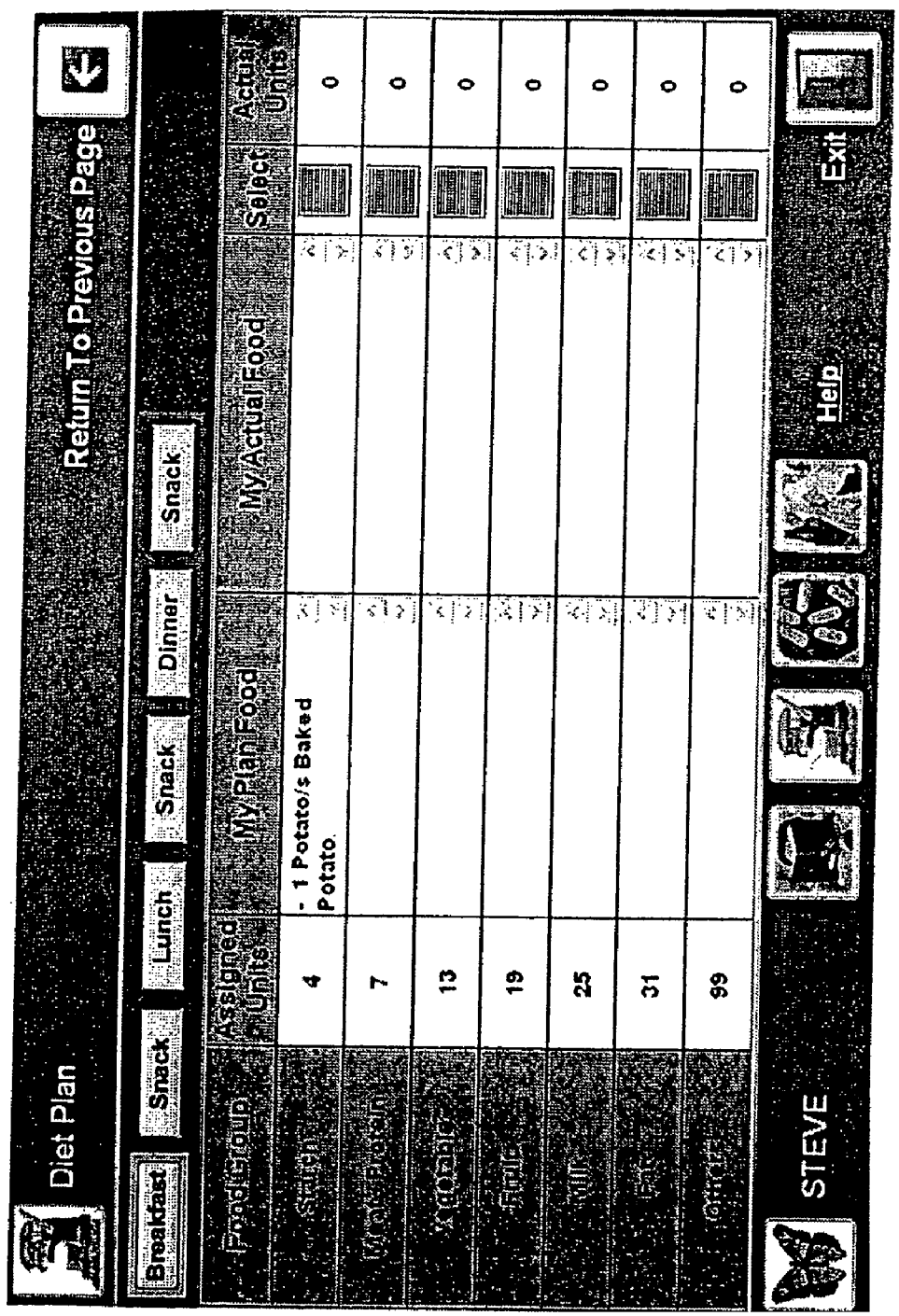
FIG. 11 is a screen in the My Meal Plan Today section.
Figure 12:
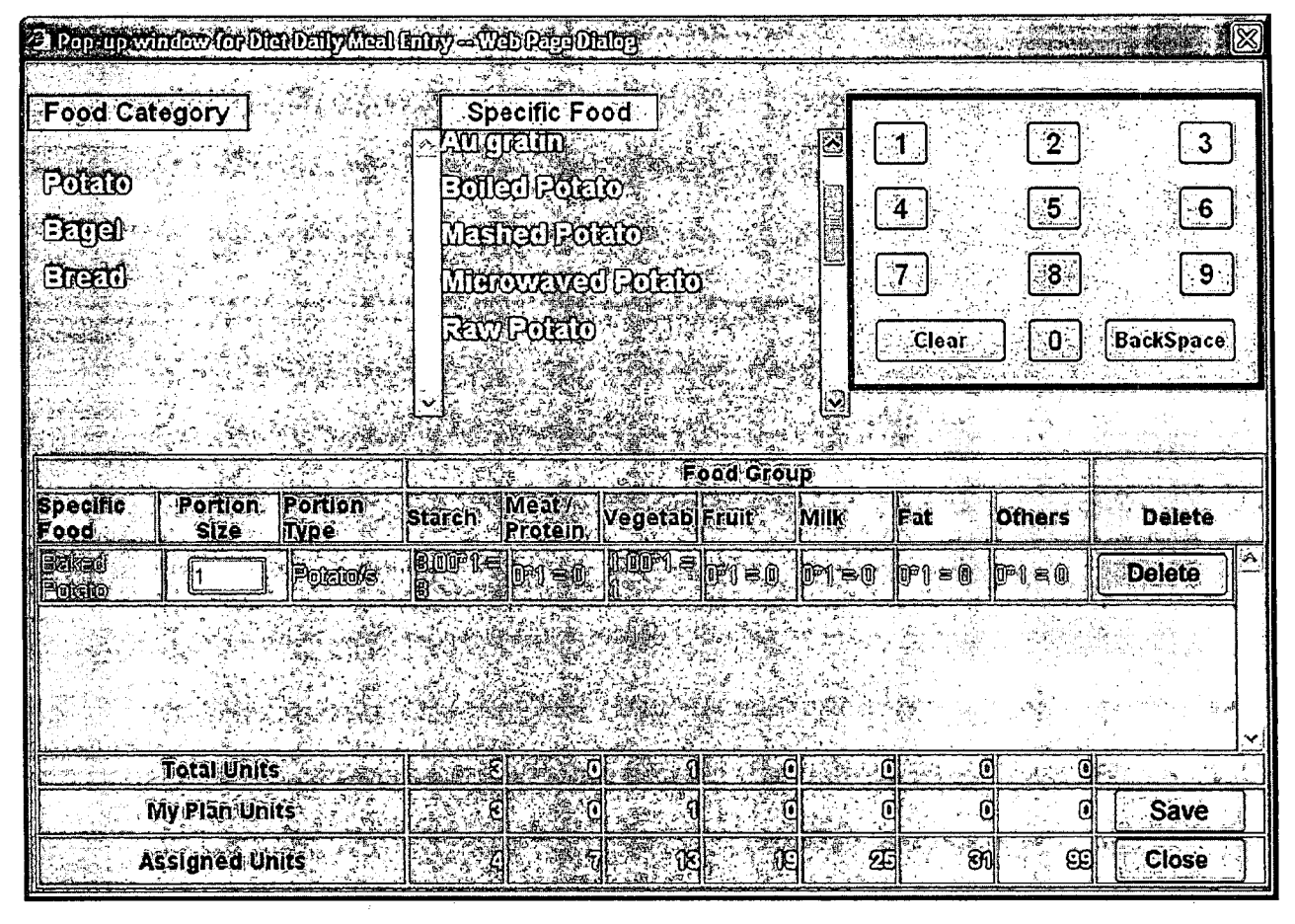

Diet. The Diet category pertains to a patient's food intake and specifically allows the patient access to information relating to a dietary plan. A clinician prescribed dietary plan can be provided to the patient. The patient is allowed to set up a customized menu plan based upon the diet plan set by the clinician. The patient, through the PRS station 102, enters their diet intake on a daily basis in units of starches, meat groups, fruits and vegetables or through entry of foods based upon their established menu. Calculations are made as to calories, carbohydrates, and protein. Preferably, the patient enters their diet intake using pictorial or text views of different foods categorized by food group. For example, FIG. 8 shows a menu screen of options for the patient to view including Customized Diet Plan, My Meal Plan Today and 2 Weeks Meal History. Upon selecting Customized Diet Plan, the patient is able to view his/her assigned meal plan as is shown in FIG. 9 by meal period such as Breakfast, Snack, Lunch, Snack, Dinner and Snack. Upon selecting My Meal Plan Today, a calendar is illustrated as shown in FIG. 10. By selecting a date, the screen as shown in FIG. 11 comes up to aid the patient in entering his dietary choices by time of day and dietary choice. Dietary choices are entered by food category and specific food as shown for example on the sample screen of FIG. 12, wherein all of the calculations and categorizations are done automatically for the patient.

Figure 15:
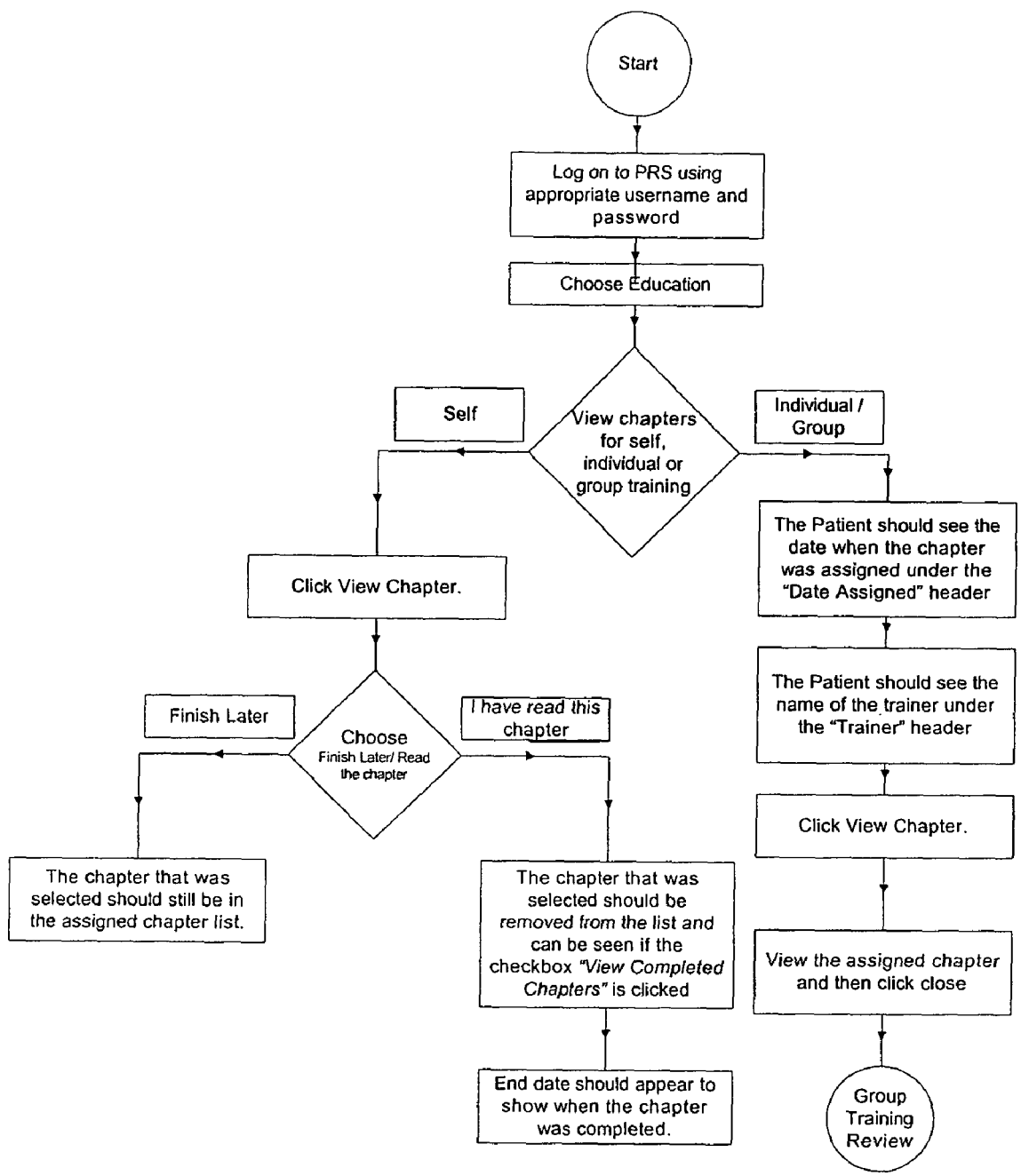
FIG. 15 is a flowchart of a portion of the Education category in the PRS.

Education. The Education category pertains to activities that impart knowledge regarding a disease and specifically allows the patient access to reading materials assigned by the clinician. Upon accessing the Education category, the patient is able to view the clinician assigned reading chapters. The PRS updates the system with the status of the patient's reading assignments and can send an alert message to the clinician if the patient has finished a particular assignment in an allotted time period and can send an alert message if the patient has not finished a particular assignment in the allotted time period. For example, upon selecting the education icon, a screen of assigned reading chapters is shown as is set forth on FIG. 13. The screen lists chapter, assign date, end date, trainer and training type. To access a chapter, the patient selects the view chapter icon and the assigned reading is pulled up such as shown in sample screen at FIG. 14. See FIG. 15 for a sample flowchart of a portion of the Education category.

Figure 16:
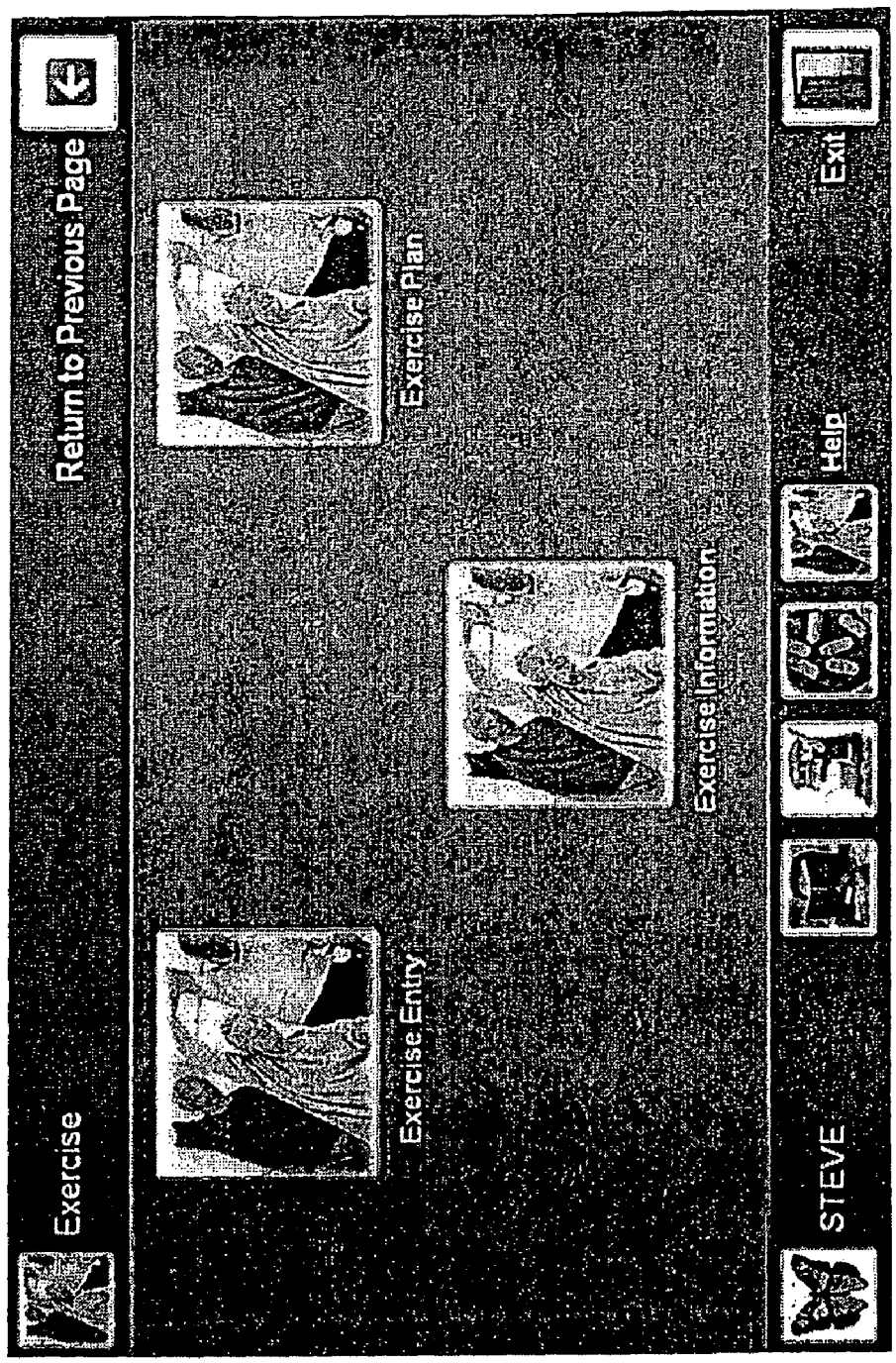
FIG. 16 is a menu screen in the Exercise category in the PRS.
Figure 17:
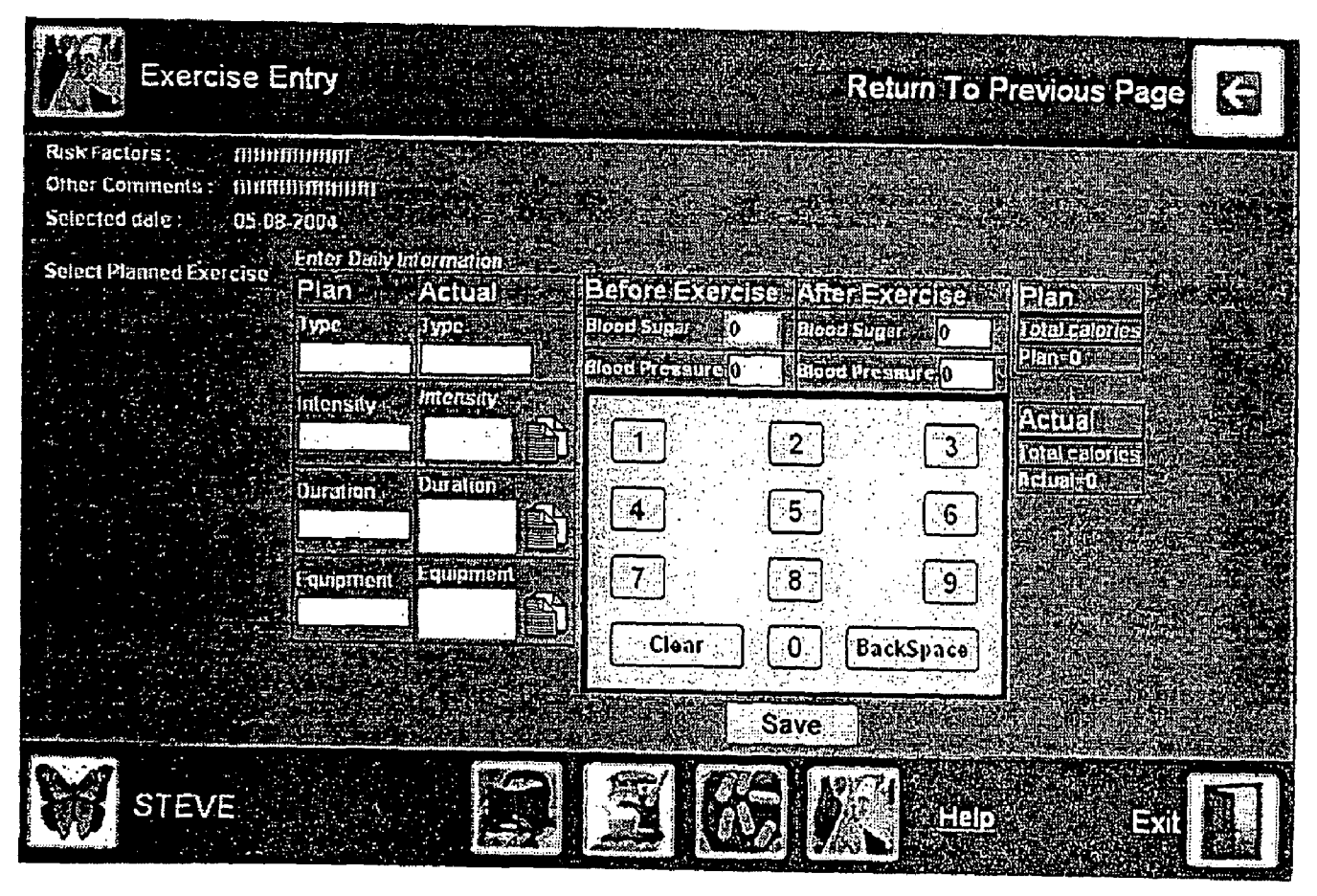
Figure 18:
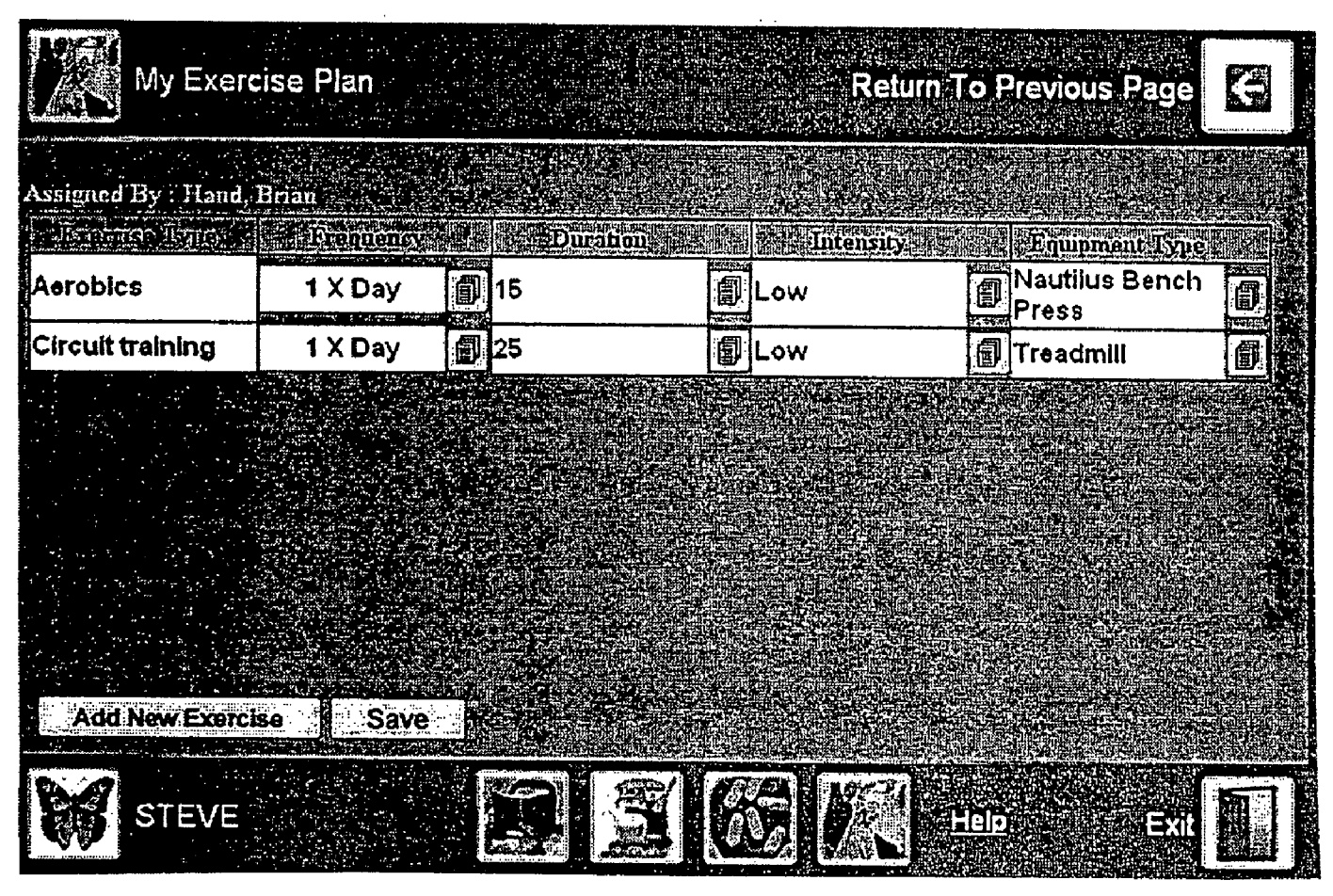
Figure 19:
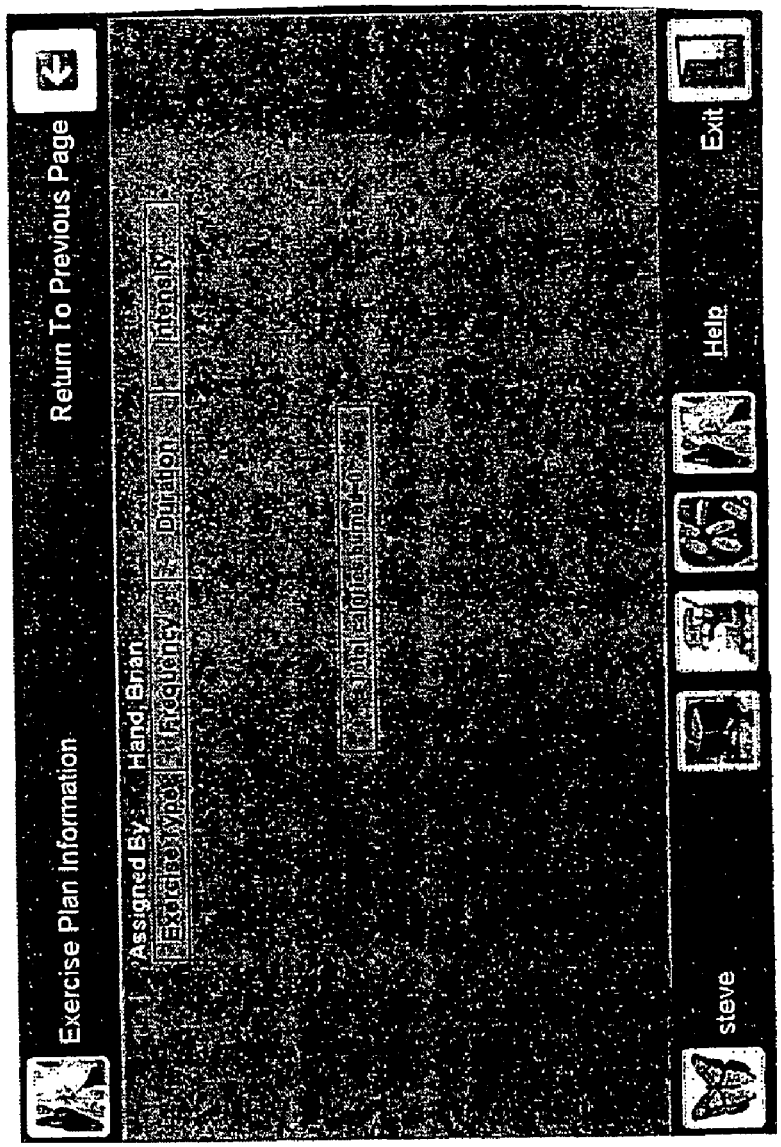
FIG. 19 is a screen in an Exercise Information section of the Exercise category.

Exercise. The Exercise category pertains to a patient's activities requiring physical exertion and specifically sets forth the exercise plan prescribed by the clinician. The patient can set up a customized exercise plan based upon the exercise plan set by clinician. The patient enters his/her activity on a daily basis or by selecting a date from a calendar. A patient can view the comparison between their prescribed exercise plan and their actual exercise. For example, upon selecting the exercise icon, a screen such as shown in FIG. 16 is provided with Exercise Entry, Exercise Plan and Exercise Information icon options. When a patient selects the Exercise Entry icon, a calendar similar to that shown in FIG. 10 is accessible for the patient to select a day. Thereafter, a screen such as shown in FIG. 17 is provided for the patient to enter exercise information. When a patient selects the Exercise Plan icon, a screen such as shown in FIG. 18 is provided illustrating the exercise type, frequency, duration, intensity, and equipment type. New exercises can be added at this screen. When the patient selects the Exercise Information icon, a screen such as that shown in FIG. 19 is accessible to provide the patient exercise information.

The PRS can also include an online help utility that may include audio or video clips. The PRS and CMS can also include an instant messaging capability to enable real time communications between a clinician and a patient.

Clinician Medical System (CMS)

The CMS 102 is installed in health or other hospital care facility providing treatment to patients. As shown in FIG. 1, the CMS 102 receives data from multiple PRS 102 to provide real-time monitoring of a population of patients. The CMS 102 allows its users to capture patient-related data as well as provide analysis capabilities for identifying problems in a population or group of patients. Availability of real-time problem identification and analysis capabilities aids clinicians in providing better care and preventative care to patients.

Users of the CMS, the types of which are detailed below, are able to monitor time spent in dealing with diabetes patients, to track educational hours, to track patient's educational hours for historical analysis, to increase productivity by viewing patient summary reports rather then going to piles of detailed paper work, to get summary information on individuals or groups, to view information graphically as well as textually, to use customized parameters for viewing graphical or textual information on individuals or groups, and to access online knowledge base relating to medications.

With respect to technical requirements for the CMS, Windows is the preferred operating system and SQL server 2000 is the preferred choice of a database. The CMS is preferably a complete web based system. It should be noted that the CMS preferably allows integration with third party health care software systems.

A user is able to log in to the CMS if they have a valid username and password. A user has the ability to change their password or request access to a forgotten password. The CMS uses security and permissions assigned to groups of users. Each user group has access to certain modules and restrictions on other modules. Under certain circumstances, for example, one group might be able to browse and edit information in a particular module while another group could only browse the same. Upon login, the user selects an entity and a facility, preferably from a pull down menu of options permissible to their login.

Figure 20A:
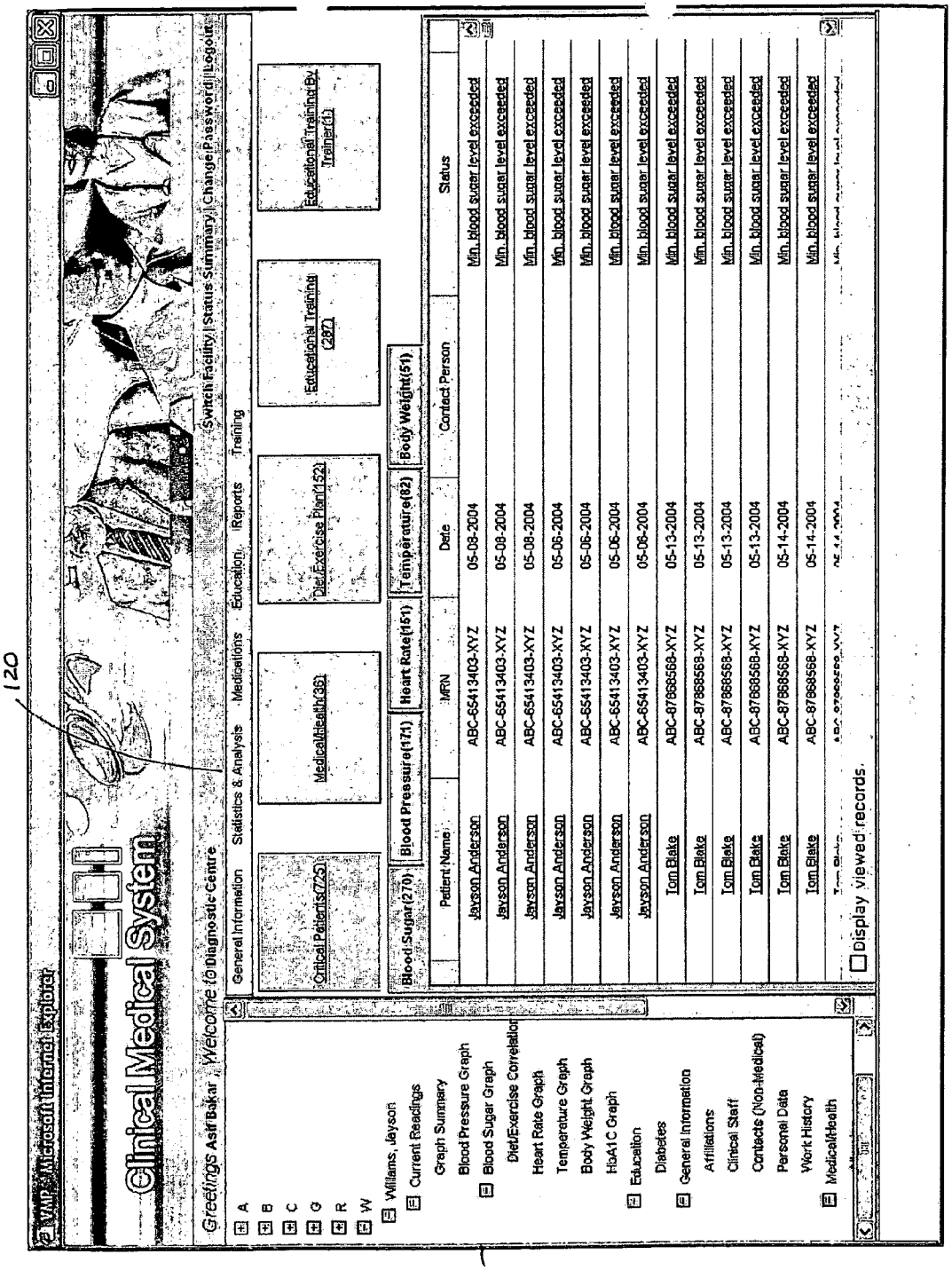
FIGS. 20A and 20B are main menu screens in the CMS.
Figure 20B:
Figure 21:
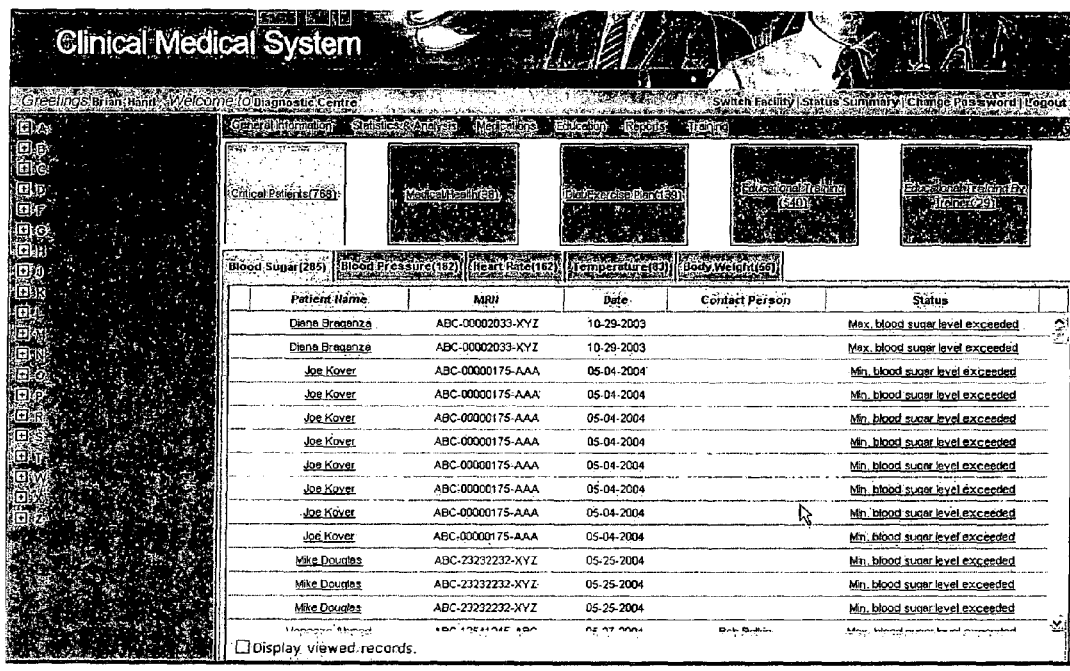
FIG. 21 is a screen showing Medical/Health alerts upon login to the CMS.

The users of the CMS include entity level administrators, facility level administrators, clinicians, data entry personnel and trainers. Each user role may have more than one sub-role with varying levels of user privileges. As users log in to the CMS, each user will be shown a status summary screen showing the status of various parameters within the system. Specific status parameters are available to each type of user. For example, entity and facility level administrators can set up any status alerts. Physician status alerts can include number of critical patients and number of scheduled patients for that day. Non-physician clinician status alerts can include number of scheduled trainings, number of feedback reviews, number of educational reviews and number of educational sessions. Data entry personnel status alerts can include number of patients to enter/edit data by entity and by facility. Trainer status alerts can include a day's scheduled training for individuals and for groups. See for example the alert categories of Critical Patients, Medical/Health, Diet/Exercise Plan, Educational Training and Education Training By Trainer boxes on FIGS. 20A and 20B. See FIG. 21 for a sample listing of Critical Patient alerts.

Patient information is available in the CMS as individual patient information and group information. Group information can be structured as any confirmation of individuals as the CMS user desires and defines. Preferably, individual patient information is selectable along a left axis 118 of the screen in a navigation tree and group information is selectable along the top axis 120 of the screen in pull down menus as is shown on the main menu screen of FIGS. 20A and 20B.

Individual Patient Information. Individual patient information in the CMS along axis 118 is organized alphabetically by the starting letter of the patient's last name, with only the letters A, B, C, G, R and W shown in the drawings for simplicity. To access an individual patient, the letter corresponding to their last name is selected, then the full name is selected from those shown, for example fictional Jayson Williams in FIGS. 20A and 20B. Information regarding patient Jayson Williams is divided into groups for ease of navigation and viewing. For example, the information can be divided into the groups of Current Readings, Education, General Information, Medical/Health and Lifestyle, see for example the sample screen of FIGS. 20A and 20B.

Turning now to the Current Readings group for viewing individual patient information captured within the CMS, this section provides visual summaries of various biological readings identifying a patient's current conditions. For example, the following visual information is available: Graph Summary, Blood Pressure Graph, Blood Sugar Graph, Heart Rate Graph, Temperature Graph, Body Weight Graph and HbA1C Graph.

Figure 22A:
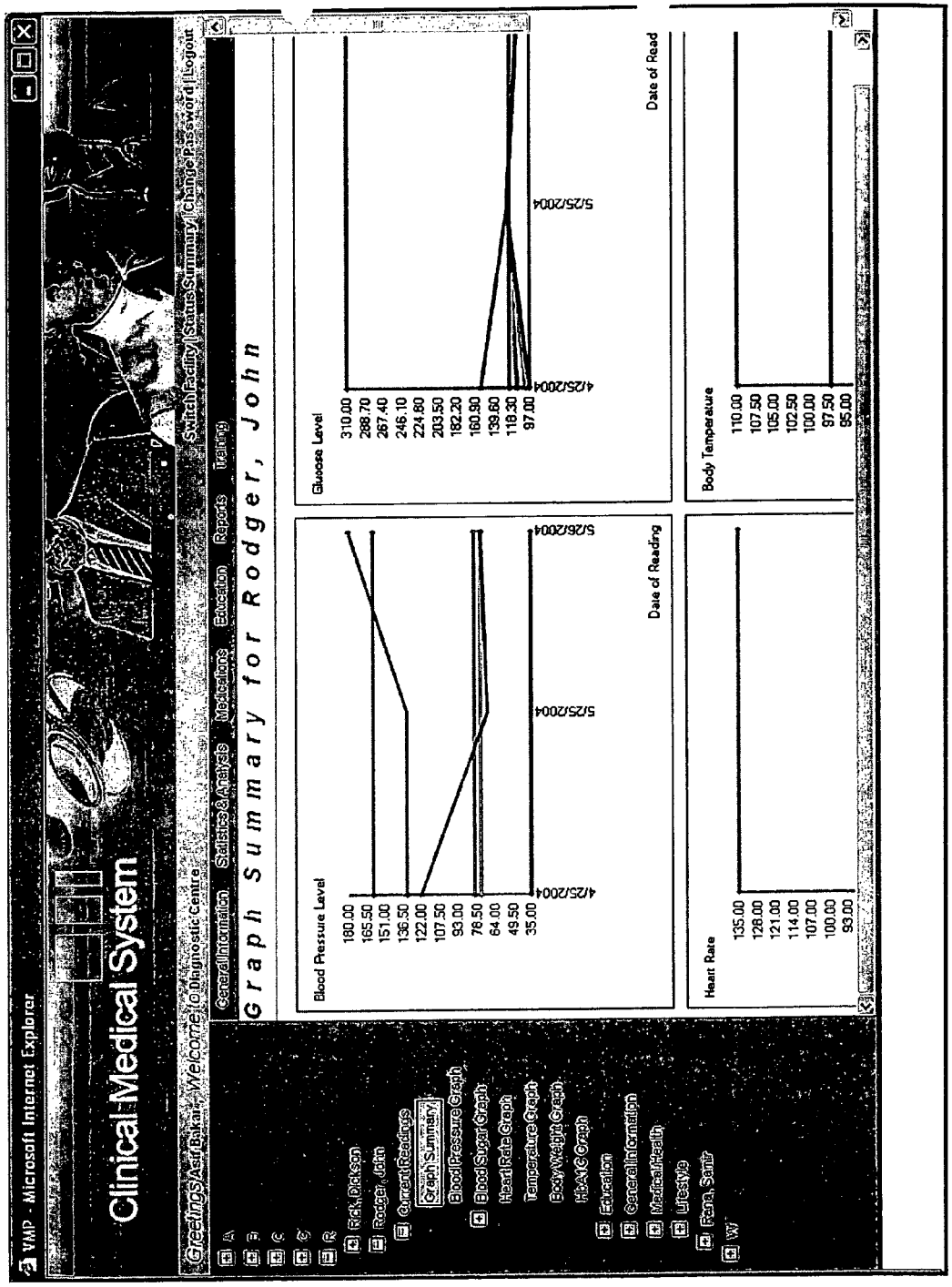
FIGS. 22A, 22B and 22C are graph summary screens in a Current Readings group in the CMS.
Figure 22B:
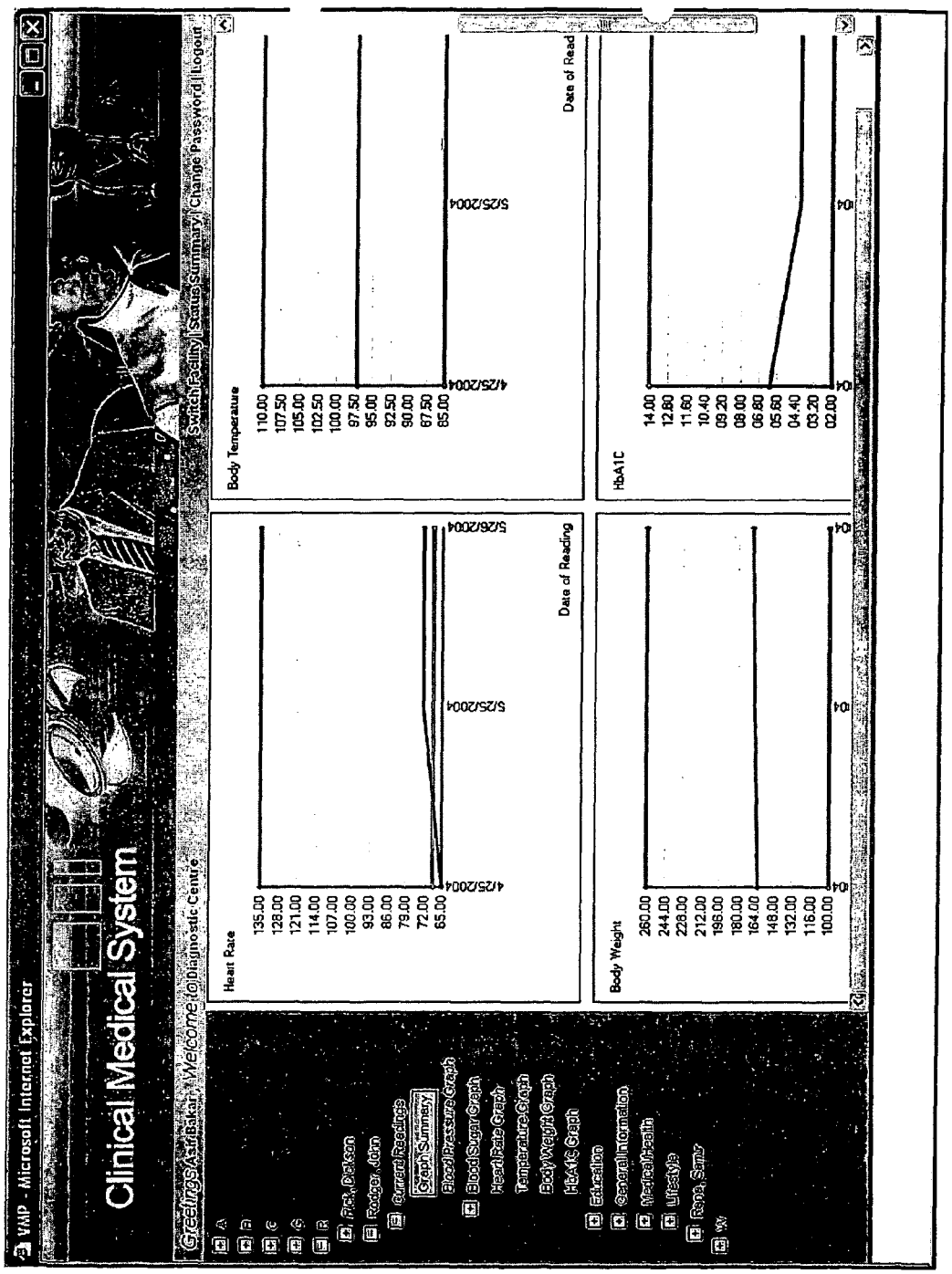
Figure 22C:
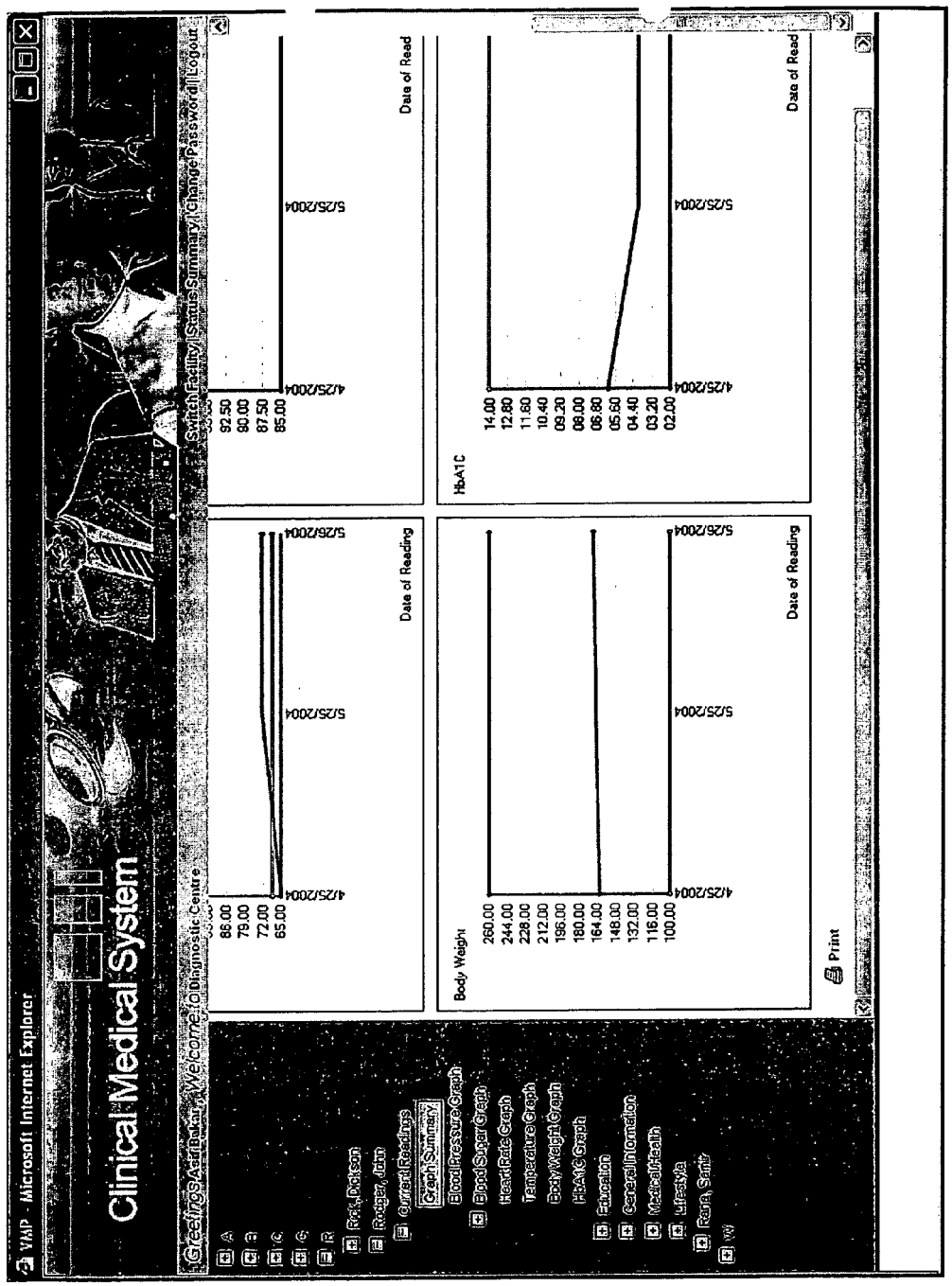

Under the Graph Summary section, a user is provided with graphs displaying blood pressure level, glucose level, heart rate, body temperature, body weight and HbA1C, see for example the screen of FIGS. 22A, 22B and 22C. The user has the ability to change the time span of each individual visual graph or of all of the graphs. Changing of time span is based upon calendar control so a user can pick the date ranges from a calendar or in the alternative, enter a date range manually. The user has the ability to change HI-LO values for each individual graph or for all of the graphs. The HI-LO values established by the user can be set using system defaults, can be set for closer patient monitoring, and can be set using short term values that expire after a time set by the user then return to the values previously set. The HI-LO values can be so set for individual patients or groups of patients. The user has the ability to click on any individual graph to view a larger image of the graph in a new window.

Under the Blood Pressure Graph section, the user is provided with a graph displaying the blood pressure information. The user has the ability to change the time span of the graph either using calendar control or manually. Three radio buttons are provided which allow for showing the data in grid format, graph format, and both formats. A textual information table shows the last three readings based on the last three clinic visits or the last three readings inputted into the PRS.

Figure 23:
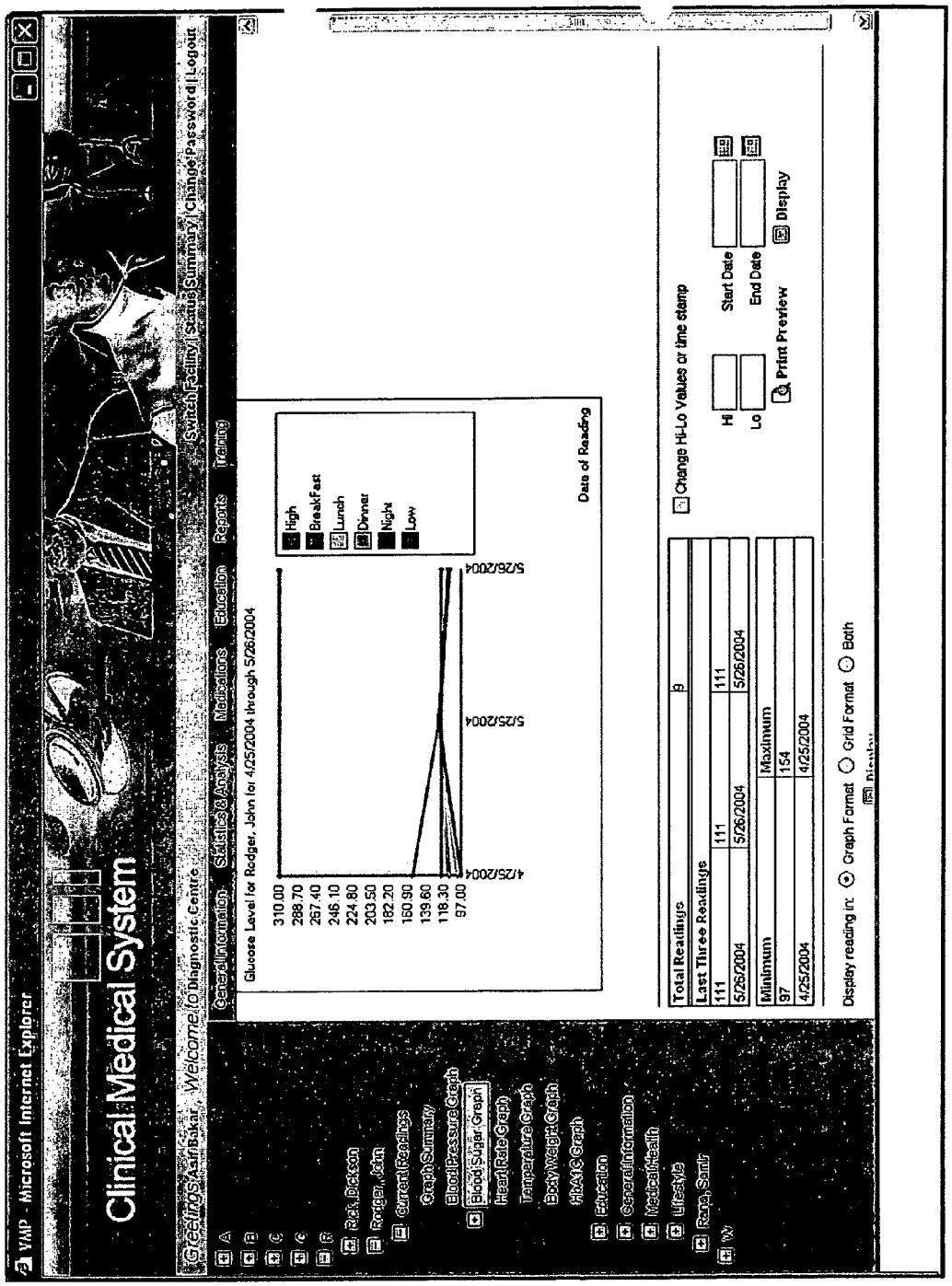
FIG. 23 is a glucose level graph screen in the Current Readings group.

Under the Blood Sugar Graph section, a graph is displayed of glucose levels, see for example the screen of FIG. 23. The user has the ability to change the time span of the graph either manually or using calendar control. A textual information table is provided showing minimum and a maximum blood sugar levels. Three radio buttons are provided for showing the data in grid format, graph format, and both formats. A textual information table is provided showing the last three minimum and maximum blood sugar readings based all the data available in the system.

Under the Heart Rate Graph section, a graph is displayed of heart rate readings. The user can change the time span of the graph either manually or using calendar control. Three radio buttons allow for showing the data in grid format, graph format, and both formats. A textual information table is provided showing the last three readings based on the last three clinic visits or the last three readings inputted into the PRS.

Under the Temperature Graph section, a graph is displayed of temperature readings. The user can change the time span of the graph either manually or using calendar control. Three radio buttons allow for showing the data in grid format, graph format, and both formats. A textual information table is provided showing the last three readings based on the last three clinic visits or the last three readings inputted into the PRS.

Under the Body Weight Graph section, a graph is displayed of body weight. The user can change the time span of the graph either manually or using calendar control. Three radio buttons allow for showing the data in grid format, graph format, and both formats. A textual information table is provided showing the last three readings based on the last three clinic visits or the last three readings inputted into the PRS.

Under the HbA1C Graph section, HbA1C levels are displayed. The user can change the time span of the graph either manually or using calendar control. Three radio buttons allow for showing the data in grid format, graph format, and both formats. A textual information table is provided showing the last three readings based on the last three clinic visits or the last three readings inputted into the PRS.

Turning now to the Education group for viewing individual patient information captured within the CMS, this section provides the ability for users to schedule patient education, monitor patient educational progress and to take action on various education-related activities. This group has the two separate functions of assignment of educational reading chapters and monitoring of the status of educational training.

Figure 24:
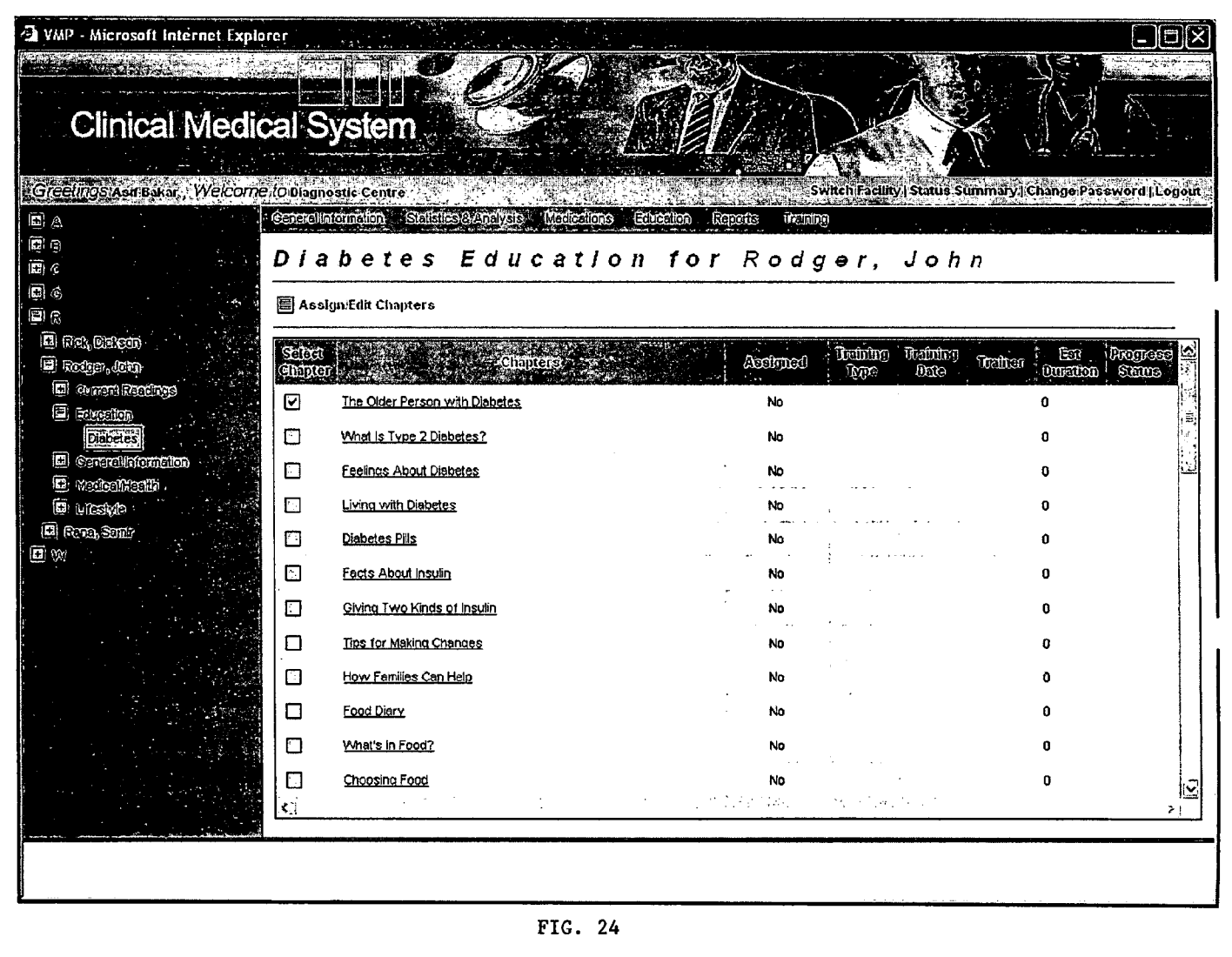

In accessing the Education group as set forth on FIG. 24, a user can assign educational reading chapters to individual patients. The readings can be from a variety of sources such as, for example, the American Diabetes Association's Diabetes Education Program or other such sources. The user has the ability to view all available educational chapters and all educational chapters assigned to the patients. The user has the ability to assign a chapter to a patient for group training, individual training or self-training. In the case of group training, the user identifies the trainer who is to conduct the group training. In case of individual training, the user identifies the trainer who is to conduct the individual training. In case of self-training, the patient is informed through pager, telephone, email, and/or the PRS that a training has been assigned to them as self-paced training. The user has the ability to view the progress of a patient on a particular educational chapter. Estimated duration of each assigned chapter can also be provided.

During the course of working on a specific educational chapter in the PRS, a patient can provide feedback. The feedback is available and viewable for the user of the CMS. The user has the ability to manage feedback by acting on it. After reading the feedback, the user presses an "Acknowledge" button to submit that the feedback has been read.

When scheduling a "Needs Review" for a patient, a user enters comments to describe why a patient needs a review. The user assigns a clinician to perform the review for the patient. The clinician assigned to do the review is informed about the assignment through pager, telephone or email. The clinician receives a status alert upon login to the CMS identifying the scheduled review session. The clinician selects an "Acknowledge" button to acknowledge the review session and has the ability to schedule the review session. Upon completion of the review session, the "Seeds Review" can be marked complete with a date and time stamp.

Turning now to the General Information group for viewing individual patient information captured within the CMS, this group provides the general information relating to Affiliations, Clinical Staff, Contacts (Non-Medical), Personal Data, and Work History.

The Affiliations section is used to view, to add and to edit information relating to affiliations of the patient for non-medical entities that track the social aspect of a patient's life.

The Clinical Staff section is used to display specialists associated with the healthcare of the patient. The user has the ability to add a new specialist, edit an existing specialist, inactivate an existing specialist and view all specialists assigned to a patient including their name, specialty, address, and contact information.

The Contacts (Non-Medical) section is used to display a patient's contact information. A user has the ability to add new contacts, edit existing contacts, inactivate contacts, and to view all contacts.

Figure 25:
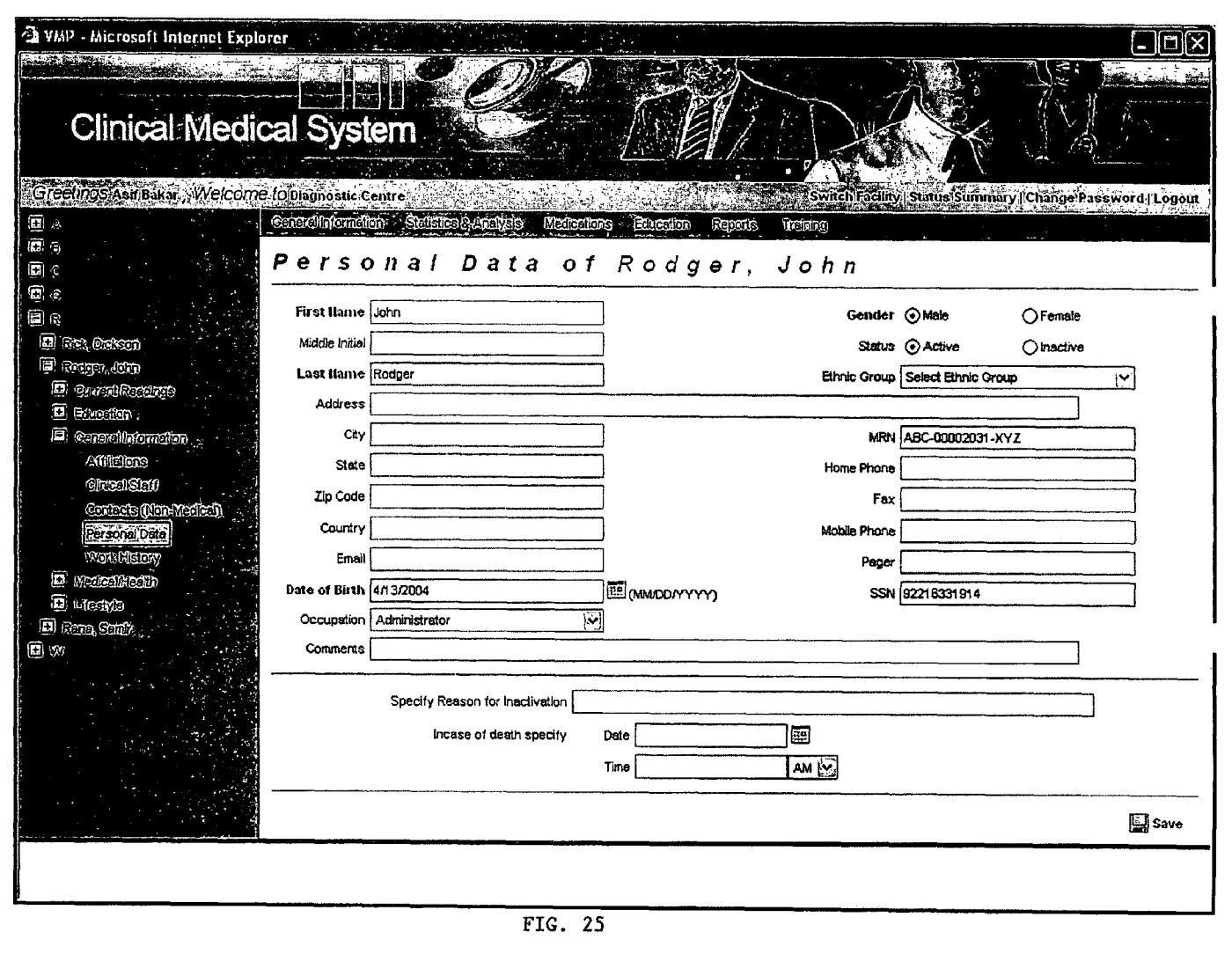

The Personal Data section is used to add, to view and to edit patient personal demographic information. This section shows the same information that is captured during data entry of a new patient into the CMS. FIG. 25 is an exemplary screen for entering and editing personal data.

The Work History section is used to view data relating to a patient's work history. A user has the ability to add new work history, edit existing work history, view work history overview, and view details of the work history. Work history information can include employer name, length of work, address of employer, employer contact information, and type of work.

Turning now to the Medical/Health group for viewing individual patient information captured within the CMS, this group is used to describe medical and health related information for a given patient. The following is a list of exemplary medical/health information: Allergies, Diabetes, Last Visit, Medical History, Medication, Psycho-Social and Skin Wounds.

The Allergies section is used to view, to add and to edit data relating to a patient's allergies. The user can assign new allergies to a patient, edit allergies by changing the symptoms related to the allergy, add a "diagnosed by" clinician name, inactivate allergies assigned to a patient, and view active patient allergies and their symptoms as well as inactive allergies and their symptoms.

Figure 26:
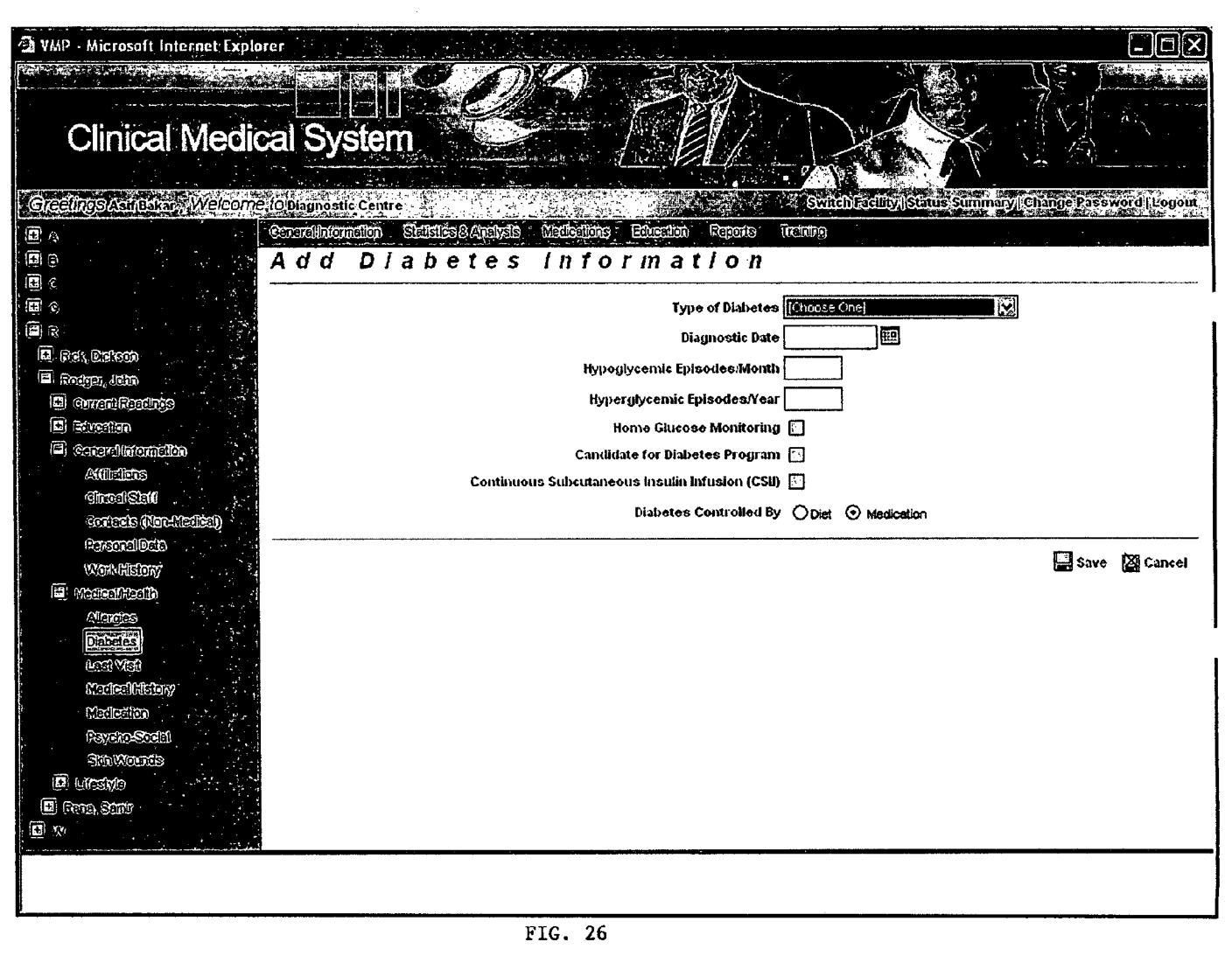

The Diabetes section is used to view, to add and to edit data relating to the type of patient diabetes. A user is able to add patient diabetes information such as is shown on the sample screen of FIG. 26.

Figure 27:
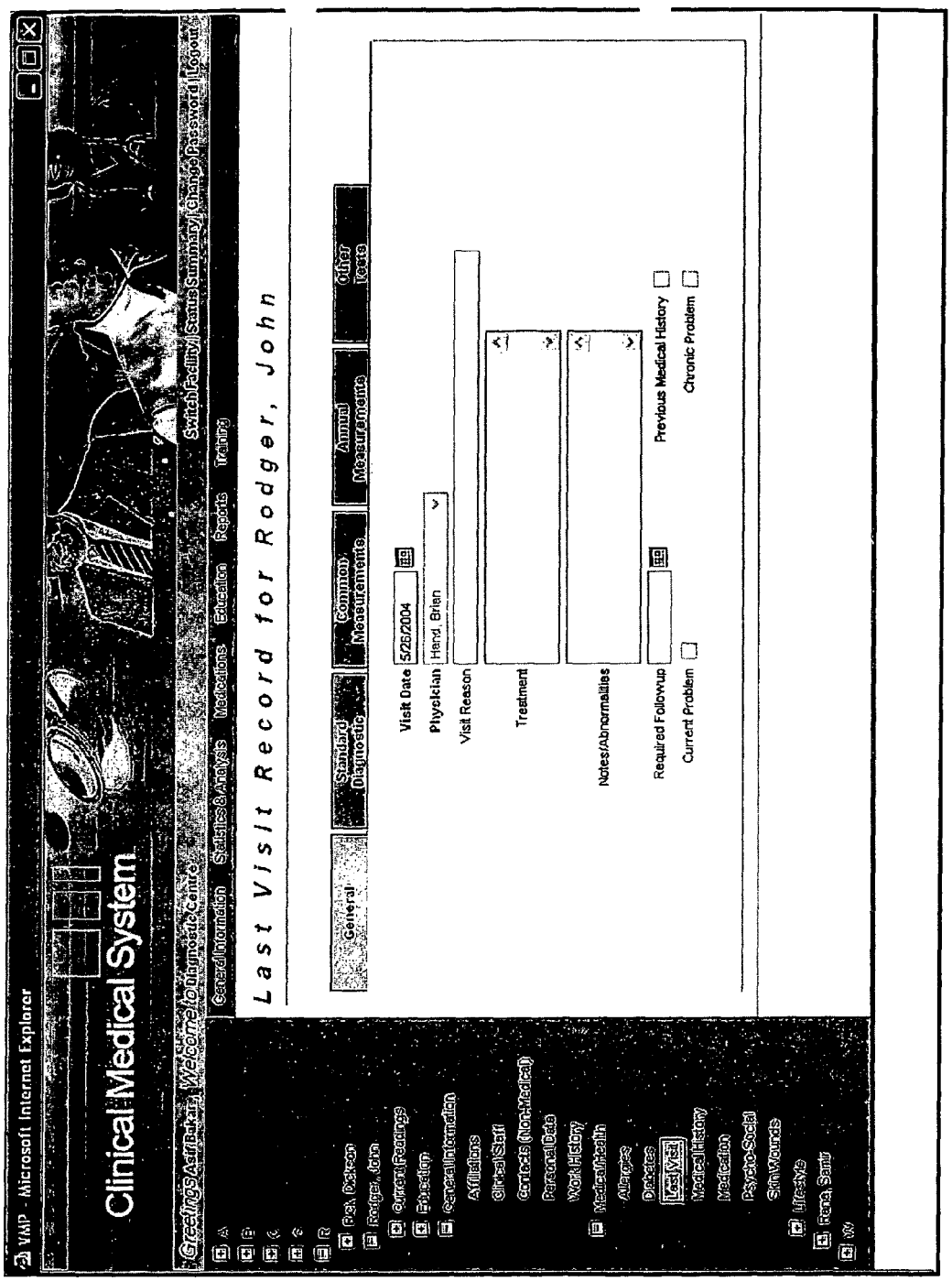
FIG. 27 is a last visit screen in the Medical/Health group.

The Last Visit section is used to view data relating to patient's last visit at a facility based upon user login. The user has the ability to add the reason for the visit and if the problem was solved or not solved during the last visit, to view blood sugar levels from last visit, to view lab results from last visit, to view blood pressure readings from last visit, to view any abnormalities, to view progress notes, and to view any specialist a patient might have seen. See FIG. 27 for a sample screen.

The Medical History section is used to capture and view patient visit information. The user has the ability to enter current patient visit information, to edit historical patient visit information, to view historical patient visit information and to view history based upon procedures performed on a patient.

Figure 28:
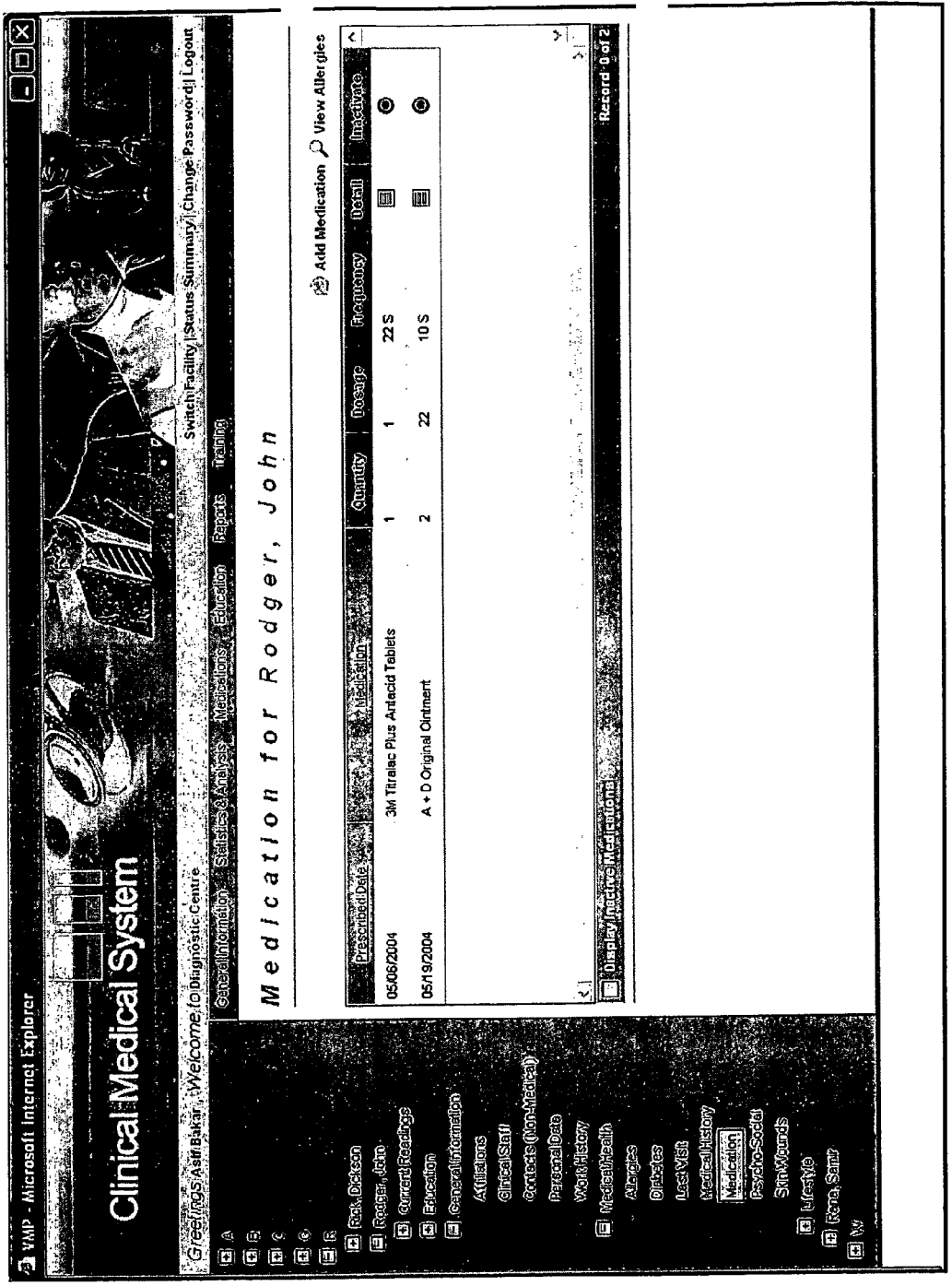
FIG. 28 is a medication screen in the Medical/Health group.

The Medication section is used to capture new medication information as well as view current and past patient medication information. See, for example, the screen of FIG. 28. A user has the ability to enter new medication names, to edit medication information and to view medication history. Medication history includes medication start and stop dates and current and past history on medications used by the patient. The user has the ability to inactivate a medication, to view past medications that have been inactivated, to edit medication information, and to reference current patient allergies from the Medication section.

The Psycho-Social section is used to capture information relating to a patient's general mental health. The user has the ability to view, to add and to edit psychosocial information.

The Skin Wounds section is used to capture information relating to a patient's wound history. This section allows the clinician to understand how prone a patient might be to injury.

The user has the ability to view, to add and to edit information relating to a patient's skin wounds from information received from the patients' PRS.

Turning now to the Lifestyle group for viewing individual patient information captured within the CMS, this group is used to describe patient information relating to their diet and exercise. The combination of diet and exercises provides a good view into a patient's overall lifestyle. The lifestyle information captured within the CMS included can include information on sexual activity, tobacco use, alcohol use and occupation.

Figure 29:
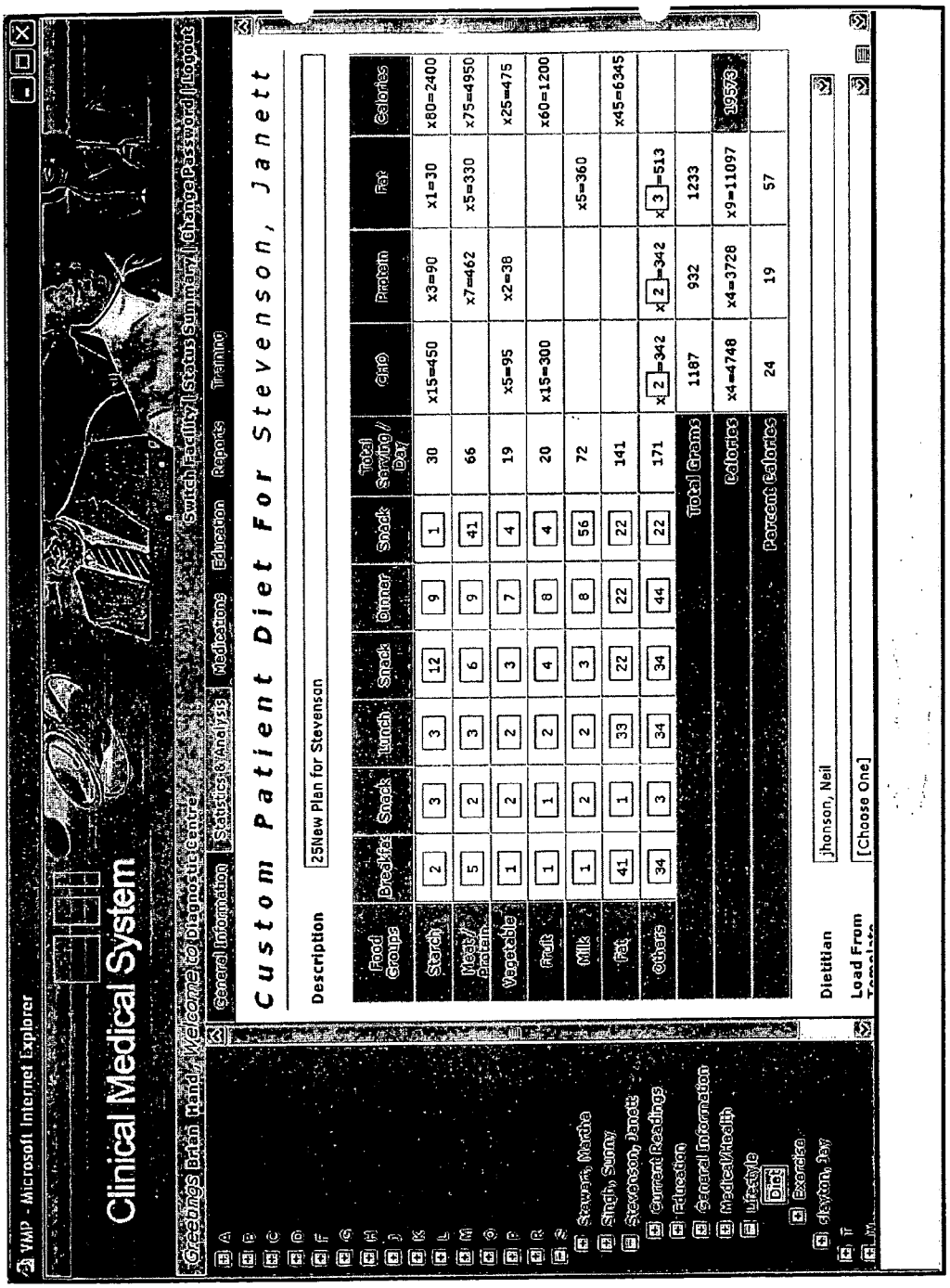
FIG. 29 is a diet plan screen in a Lifestyle group in the CMS.

The Diet section is used to view, to add and to edit data relating to a patient's diet plan as well as a patient's diet history. See FIG. 29 for a sample screen. This section is used for capturing a patient's diet history and a user has the ability to add patient diet history, to capture information about what a patient has eaten or drank for each meal, to capture nutritional supplements, to calculate the calories from the intake amount, to calculate carbohydrates, proteins and fats, and to capture other nutrients. The system has the ability to capture exceptions to normal eating habits, to provide a comparison of actual daily diet versus the baseline diet assigned by the clinician, to capture if a person is fasting, to capture information about who cooks in the family, to capture information about who does the grocery shopping, to capture information about barriers to eating, to capture information about foods that can not be eaten by a patient, to capture information about foods that a patient does not like to eat, to capture allergies related to food, to capture religious and/or cultural related food a patient cannot eat, to capture information about how often a patient eats out, to capture times of the day when a patient eats, to capture nutritional supplements information, and to capture current weight along with weight changes.

This Diet section is also used for creating a diet plan for the patient based upon a patient's diet and medical history. The user has the ability to enter a new diet plan, to assign a template diet plan, to edit an existing diet plan, to use a diet plan template to create a new diet plan, to add new diet plan templates, to create a custom diet plan, and to view diet plan histories. The diet plan information entered within the CMS is made available to the patient via the PRS.

Figure 30:
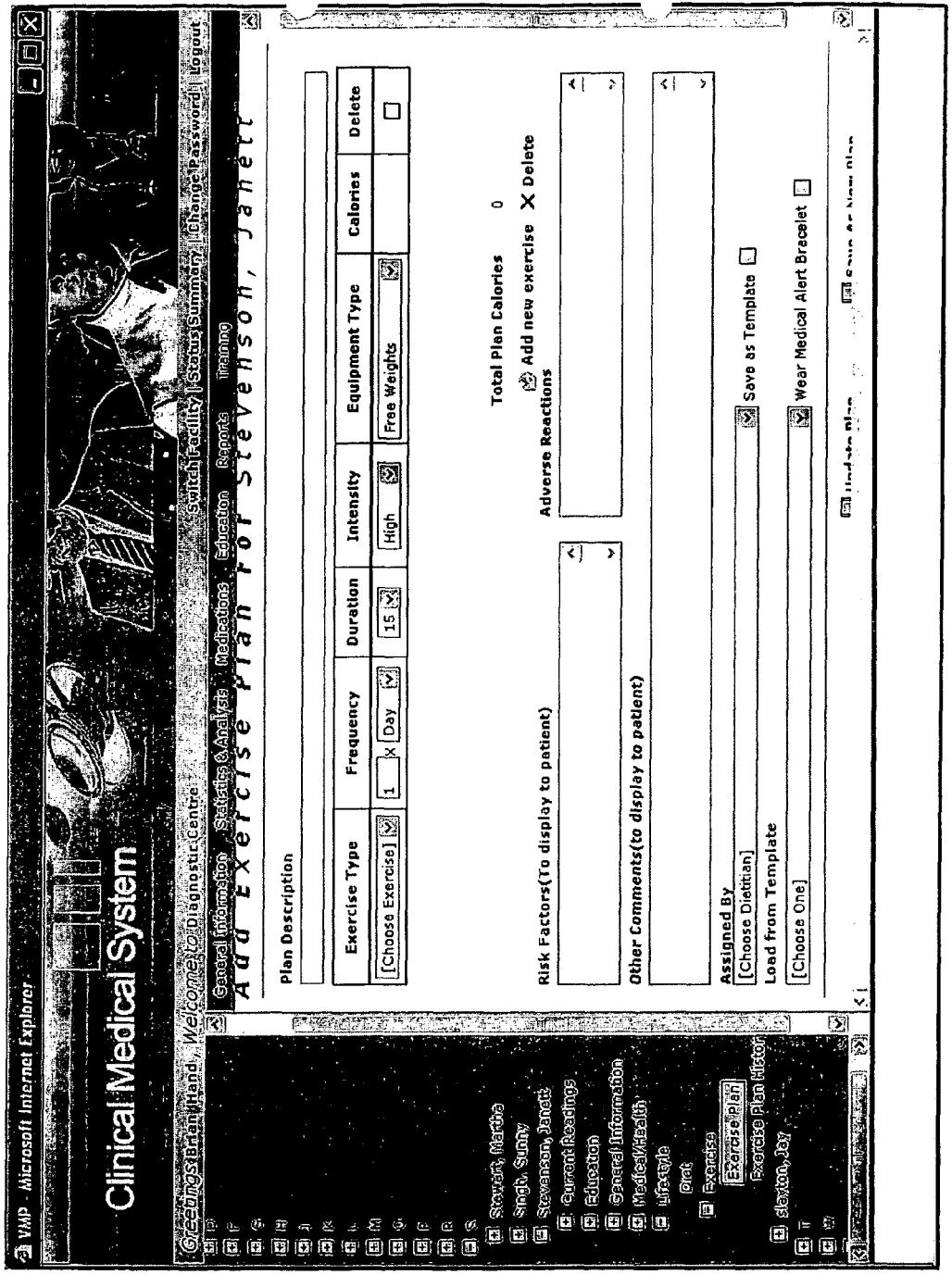
FIG. 30 is an exercise plan screen in the Lifestyle group.
Figure 31:
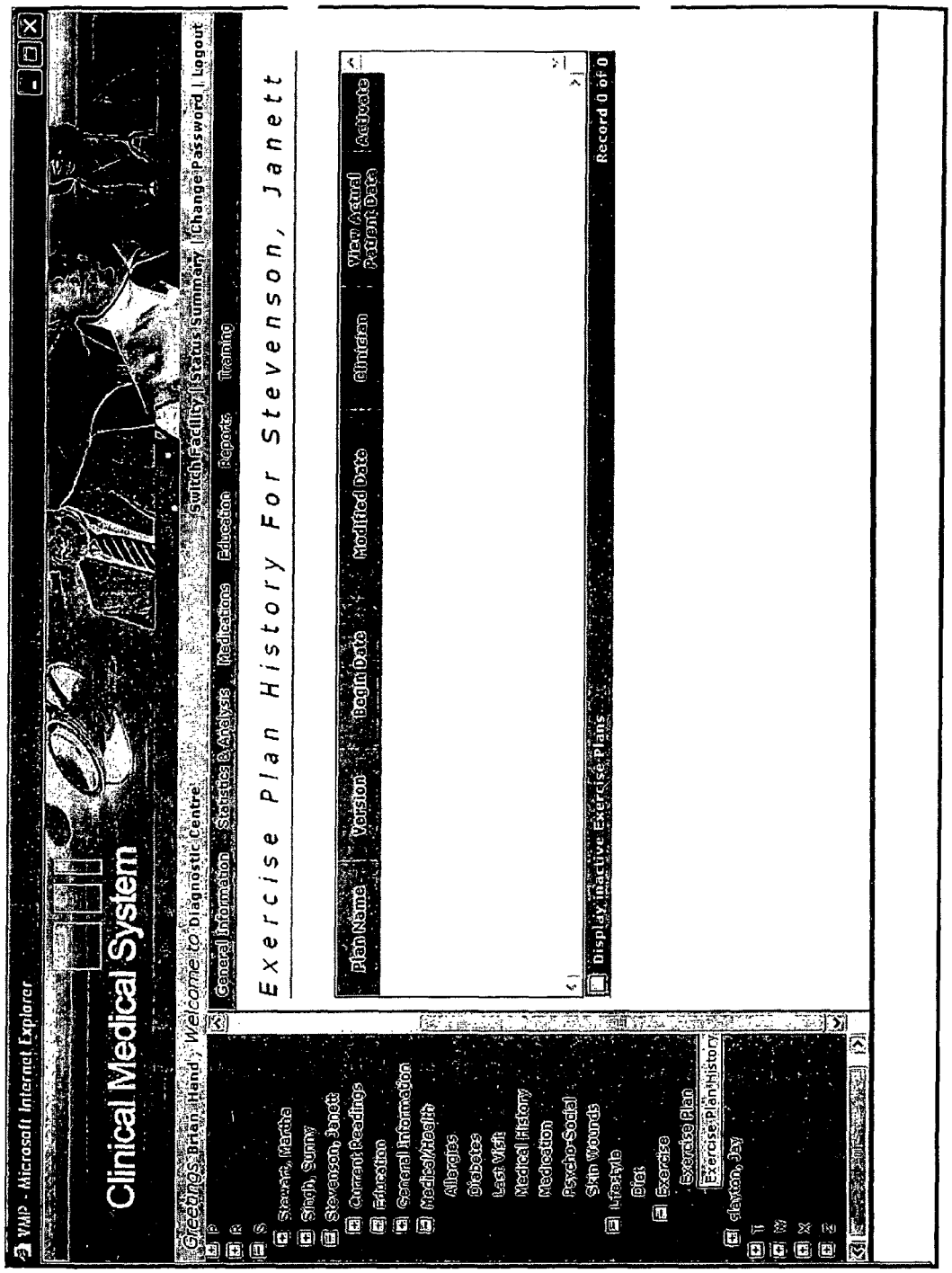
FIG. 31 is an exercise plan history screen in the Lifestyle group.

The Exercise section is used to view, to add and to edit data relating to a patient's exercise. See FIG. 30 for a sample screen to add an exercise plan and FIG. 31 for an exercise plan history. The user has the ability to create a new exercise plan, to edit an existing exercise plan, to view all past exercise plans, and to inactivate an exercise plan.

Group Information. Turning back to FIGS. 20A and 20B, users of the CMS 102 are preferably able to access group information along the top axis 120 of the screen. It should also be specifically noted that the system of the present invention can be used to gather group patient data for analysis and/or research purposes. Group information is divided into the following groups: General Information, Statistics and Analysis, Medications, Education, Reports, and Training.

The General Information group is divided into sections of Status Summary, Patient Search, Assign Patients to Clinician, Add Patient, Affiliations, Affiliation Types, Allergies, Diet Plans, Patient Groups, Exercise Plans, Patient-Personnel Reports, and Personnel-Facility Reports.

The Status Summary section is preferably the section visible upon login as was detailed above. This section is particularly useful in bringing to the attention of the user the patients needing the most attention.

The Patient Search section is used to search for patients by last name, partial name, full name or medical records number.

The Assign Patients to Clinician section is used to capture information relating to each patient and the clinical staff working with a particular patient. The user has the ability to view the relationship between patient and the clinical staff and to view all patients assigned to a particular clinician.

Figure 32:
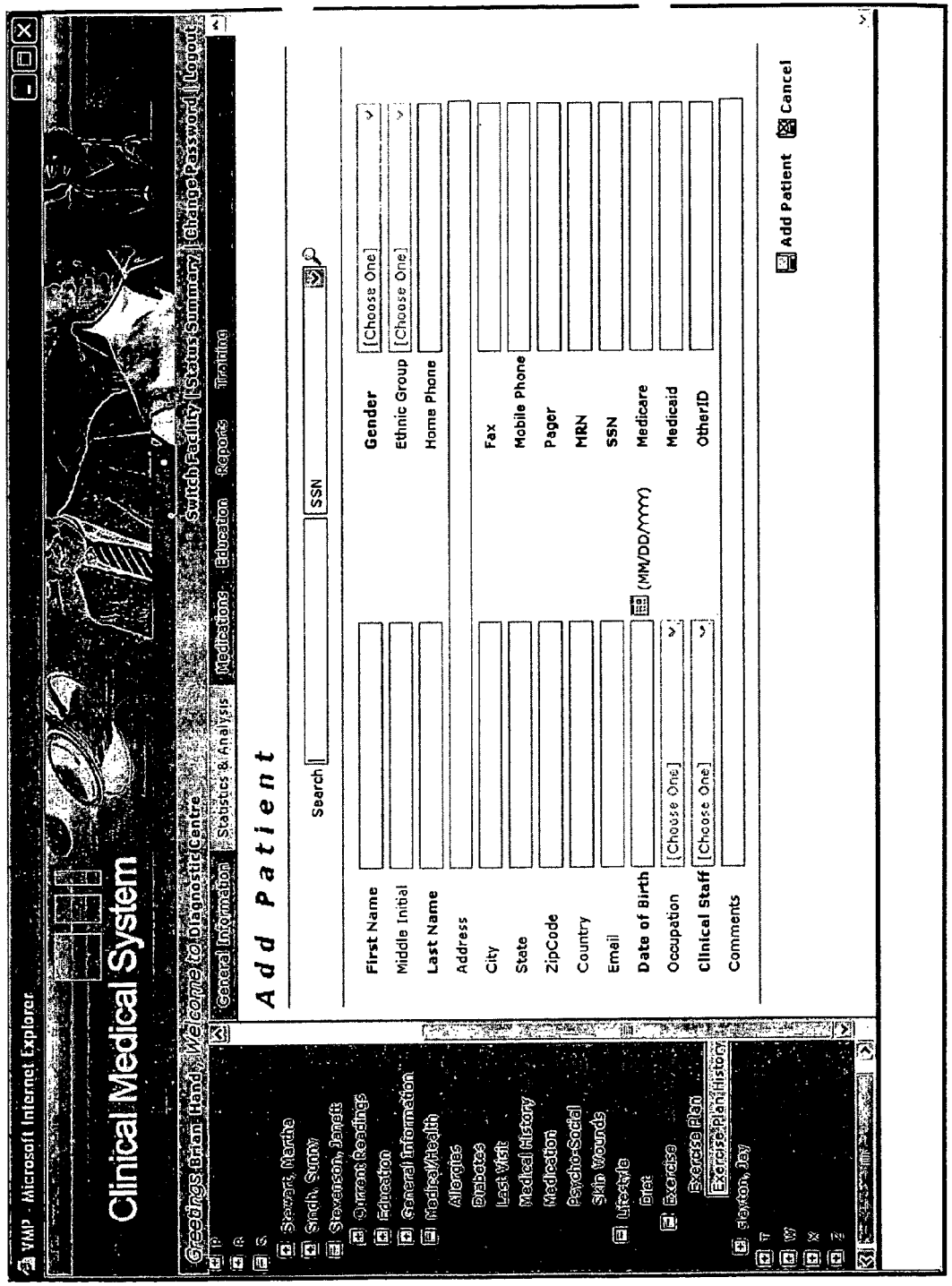
FIG. 32 is an add patient screen in a General Information group in the CMS.

The Add Patient section is used to view, to add and to edit patient information. See FIG. 32 for a sample screen.

The Affiliations section captures information relating to any type of organization that any patient could be associated with. The user has the ability to add new affiliations, to edit new affiliations, to view patient affiliations, to import data for affiliations, and to inactivate an affiliation.

The Affiliations Types section provides a listing of all types of affiliations.

The Allergies section is used to add, to edit or to inactivate new allergies in the CMS.

The Diet Plans section captures information for creating diet plan templates. These diet plan templates are used throughout the system. The user has the ability to create a new diet plan template, to edit an existing diet plan template, and to inactivate an existing diet plan template.

Figure 33:
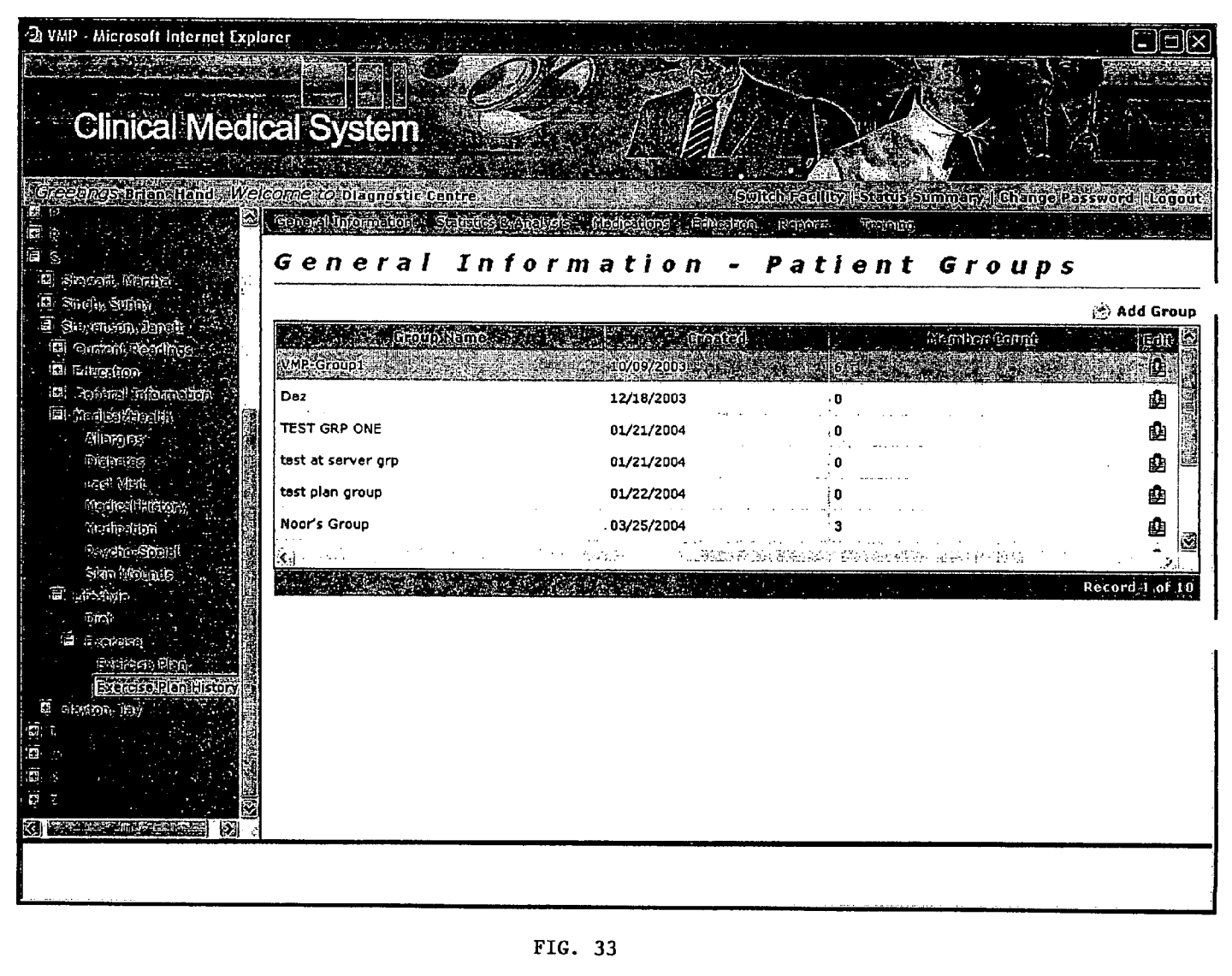

The Patient Groups section captures information for creating patient groups. These groups are used for scheduling educational training, monitoring or viewing group reports. The user has the ability to create a new group, to edit an existing group, to inactivate an existing group, to add new patients to a group, to delete patients from a group, to view inactive groups, to view other groups and to report on patients in multiple groups. See FIG. 33 for a sample screen.

The Exercise Plans section captures information for creating exercise plan templates. These templates are used throughout the system. The user has the ability to create a new exercise template, to edit an existing template, and to inactivate an existing template.

The Patient-Personnel Report sets forth a listing of patients assigned to personnel or personnel assigned to a patient.

The Personnel-Facility report sets forth a listing of a personnel assigned to a facility or facilities assigned to a given person.

Turning now to the second group of the Group Information, the Statistics and Analysis group captures basic count reporting information for numerous parameters. The CMS generates the following counts: Male/Female Count, Diabetic Type Count, Age Range Count, IFG/IGT, Insulin Oral Hypoglycemic, Diet Controlled and Ethnic Group Demographics.

Specifically, the Male/Female Counts section sets forth the number of male and female patients. The Diabetic Type Counts section sets forth the number of patients that are type 1 and type 2. The Age Range Counts section sets forth patient counts by age range. IFG/IGT section sets forth the number of patients that are impaired fasting glucose (IFG) and the number of patients that are impaired glucose tolerance (IGT). The Insulin Oral Hypoglycemic section sets forth the number of patients that are insulin oral hypoglycemic. The Diet Controlled section sets forth the number of patients who are controlling their blood sugar level through diet. The Ethnic Group Demographics section sets forth the number of patients by ethnic group.

Turning now to the third group of the Group Information, the Medications group acts as a knowledge base reference for clinicians. The Medications group is divided into the following sections to help users gather information on various medications for patient groups: Allergies, Current Medications, Dosage and Directions, Start/Stop Date, and Medication History.

The Allergies section provides information on allergies for patient groups. The user has the ability to search on allergies to find patients associated with a particular allergy, and to search patient groups to find all allergies associated with a patient group.

The Current Medications section provides information on current medications assigned to patient groups. The user has the ability to search on medications to find patients associated with a particular medication, and to search groups to find all medications associated with a group.

The Dosage and Directions section provides information on the amount of medication to be taken at any given time and how often the medication should be taken in a given day. The user has the ability to search on medications to find patient's dosage and directions and to search patient groups to find all medications dosage and directions.

The Start/Stop Date section provides information on all medications assigned to patient groups with their start and stop dates. The user has the ability to search on medications to find patients associated with a particular medication and show the medication start and stop date and to search groups to find all medications associated with a group and show the medication start and stop dates.

The Medication History section provides information on current and discontinued medications.

Figure 34:
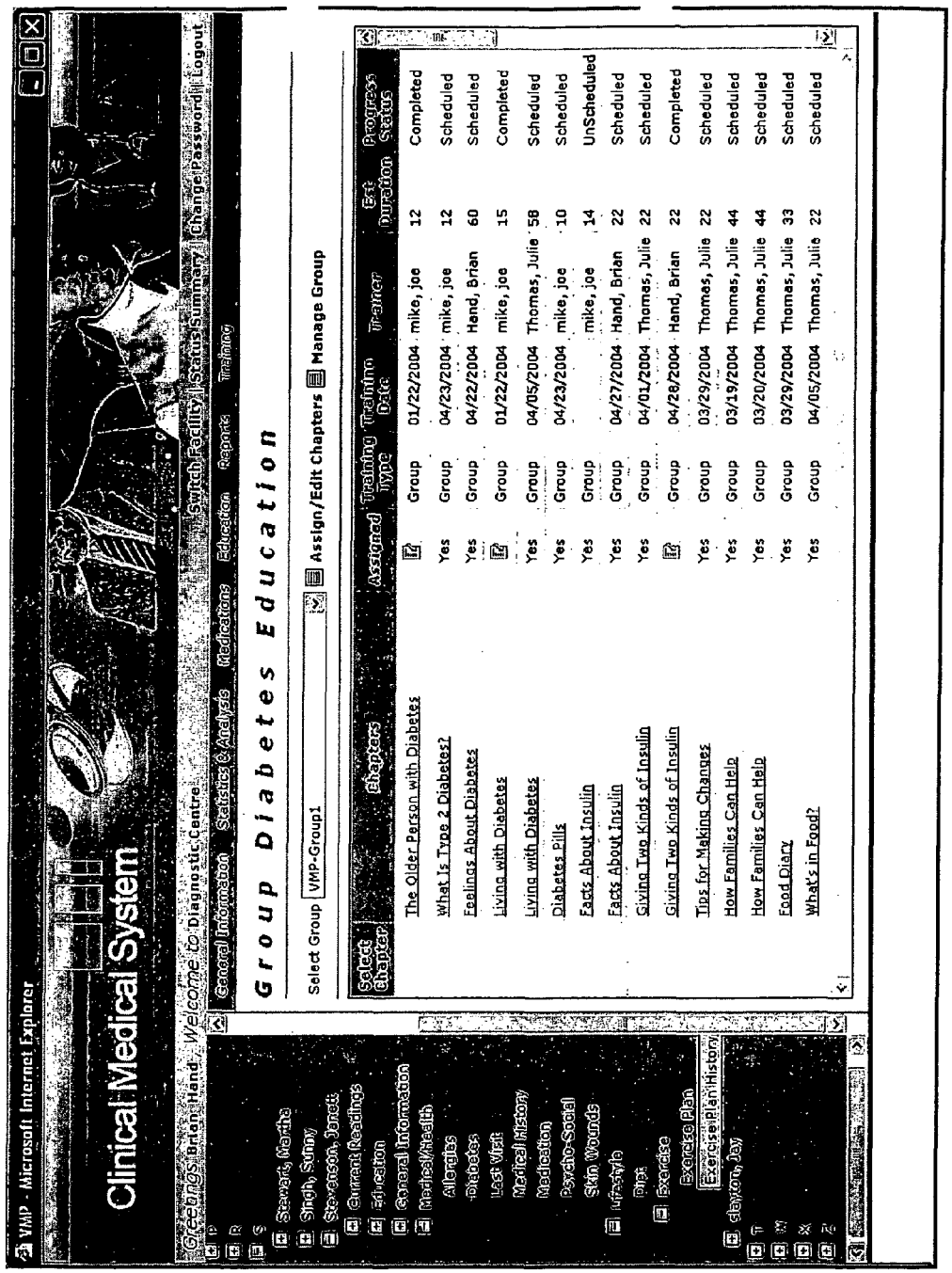
FIG. 34 is a group diabetes education screen in an Education group in the CMS.
Figure 35:
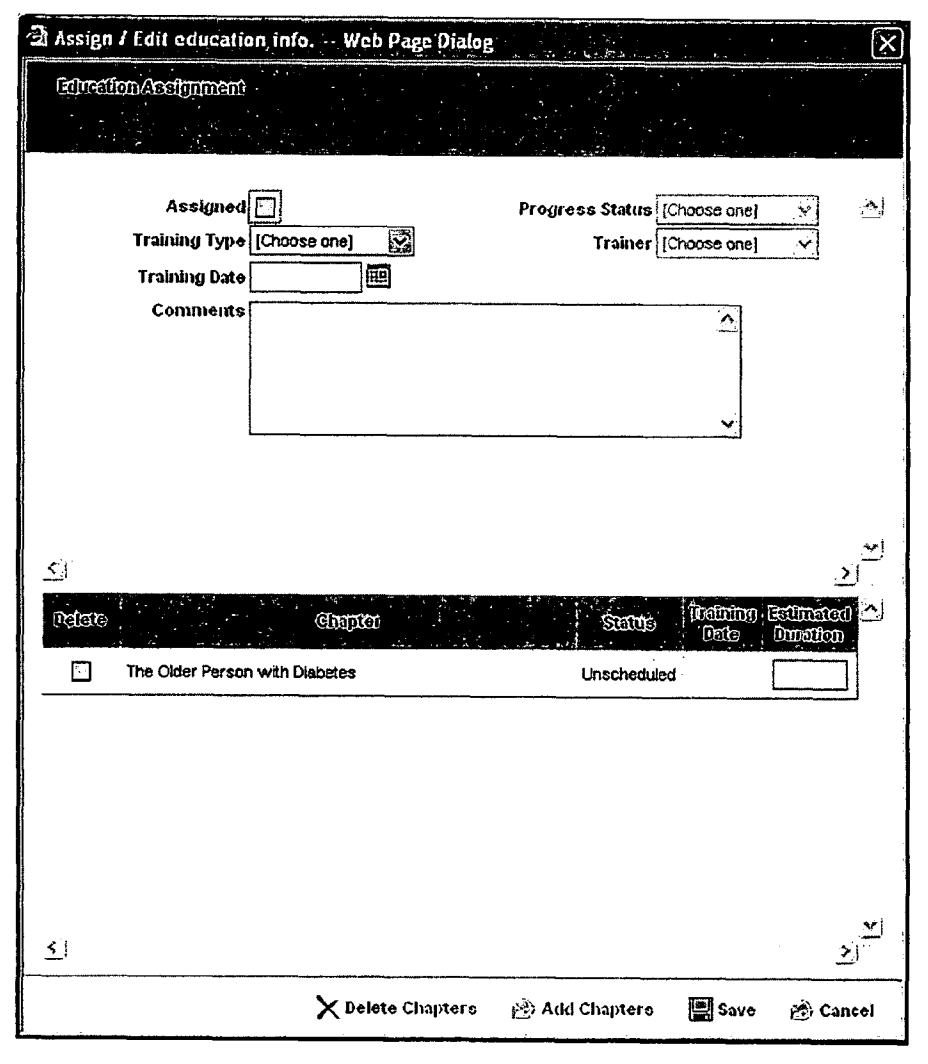
Figure 36:
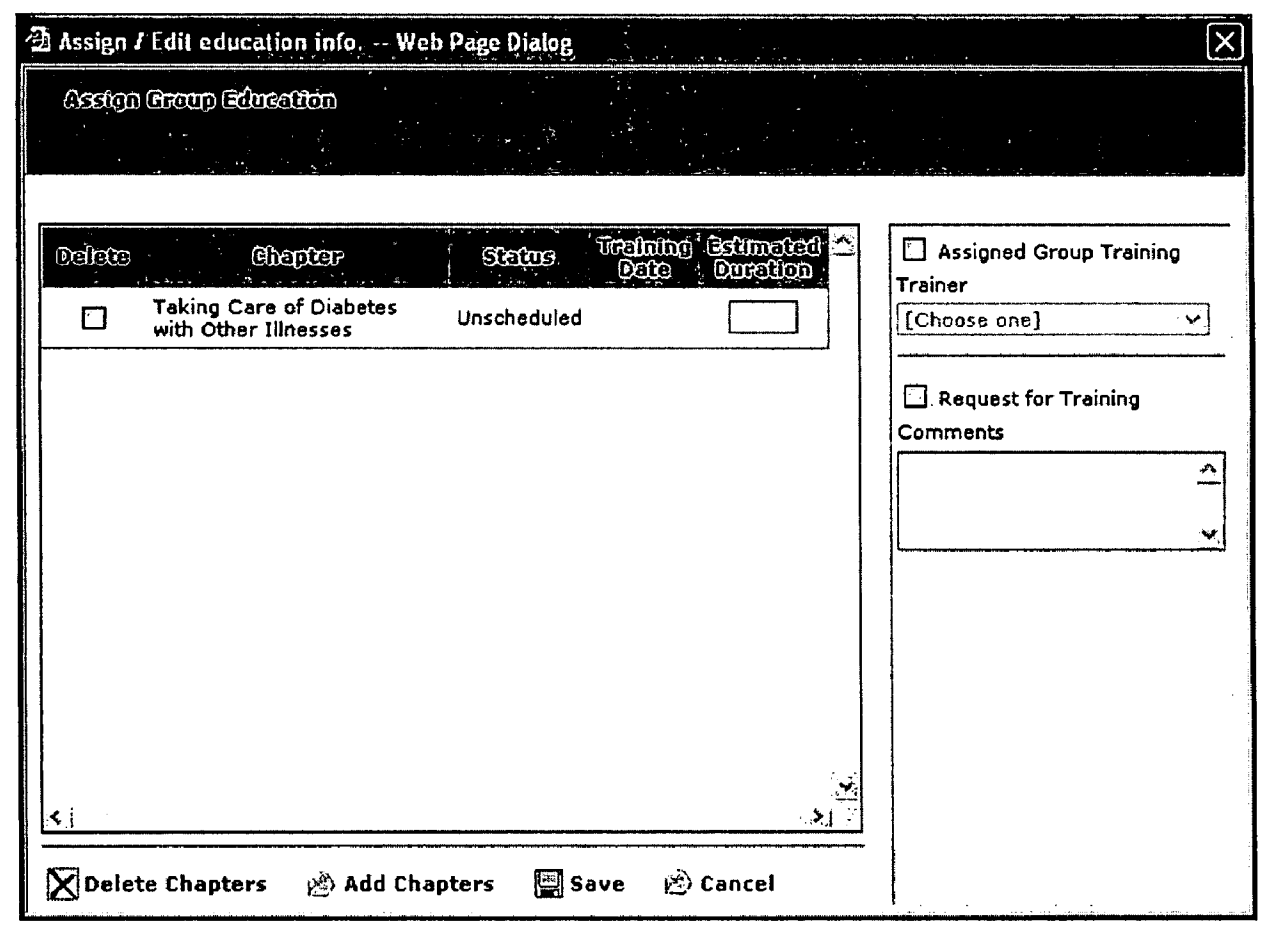
Figure 37A:
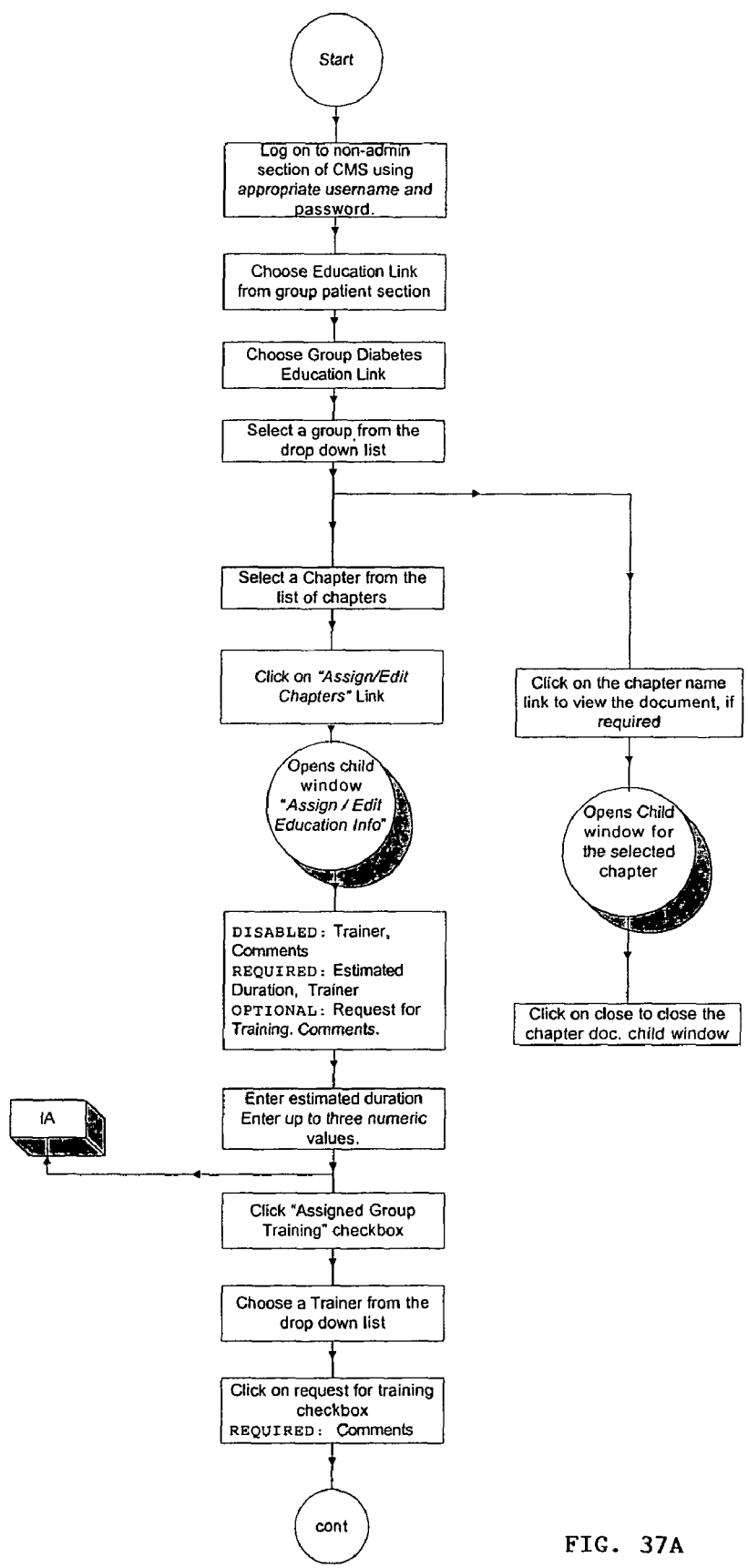
FIGS. 37A and 37B are flowcharts in the Education group.
Figure 37B:
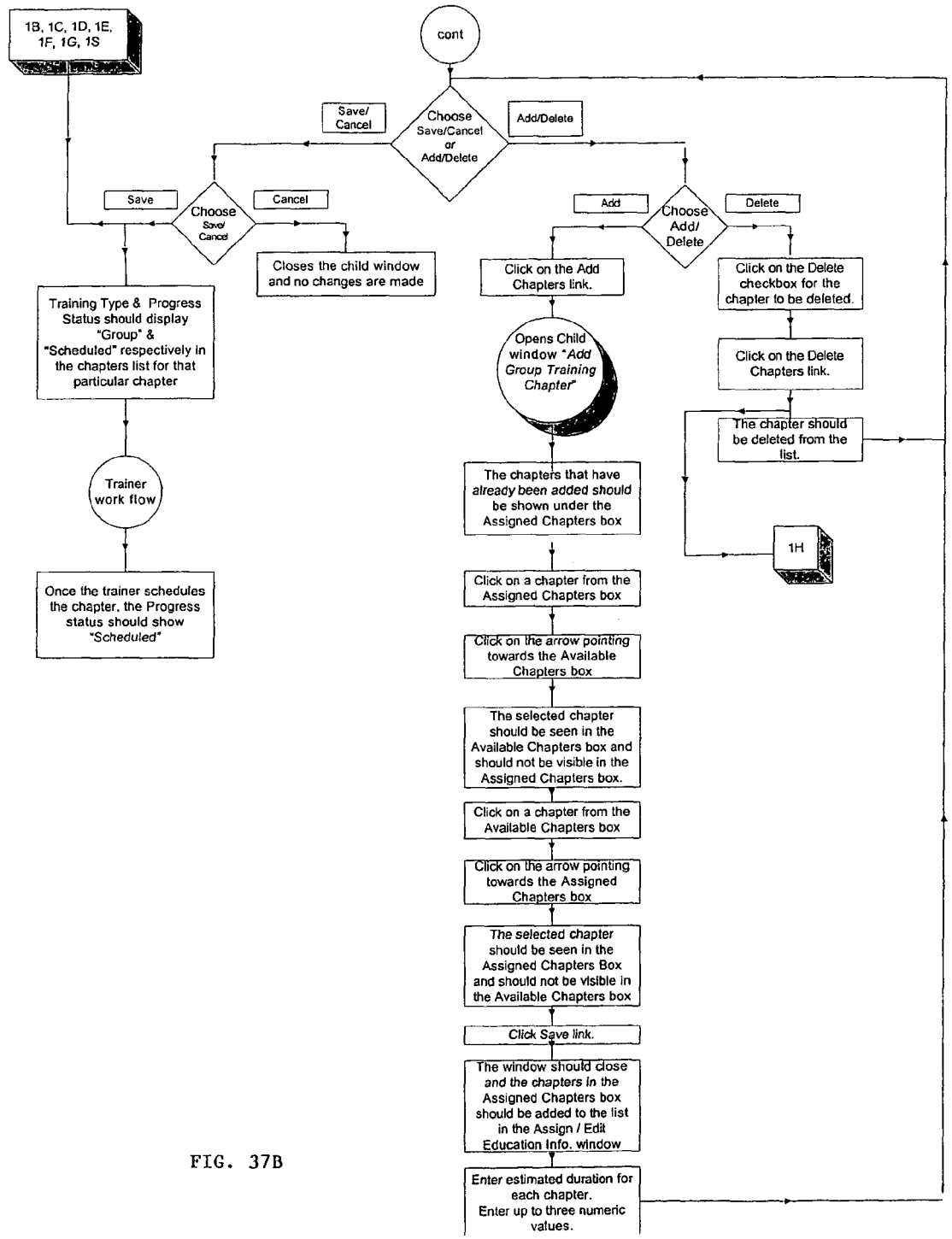

Turning now to the fourth group of the Group Information, the Education group is used to create education schedules for groups of patients as well as to update and manage the progress of a group. The user has the ability to search on individual patients, to schedule individual or group educational training sessions, to view an individual or group educational training schedule, to update progress of an individual or group educational training session, to check off individual patient attendance within a group, to enter and update the duration of time spent training an individual or group, to update 'Need Review' sessions for individual patients as well groups, to provide clinician feedback for individual patients as well as groups, to show completion of "Need Review" sessions, and to report on time spent training by individual clinicians. See FIGS. 34, 35 and 36 for sample screens and FIGS. 37A and 37B for a sample flowchart.

Figure 38:
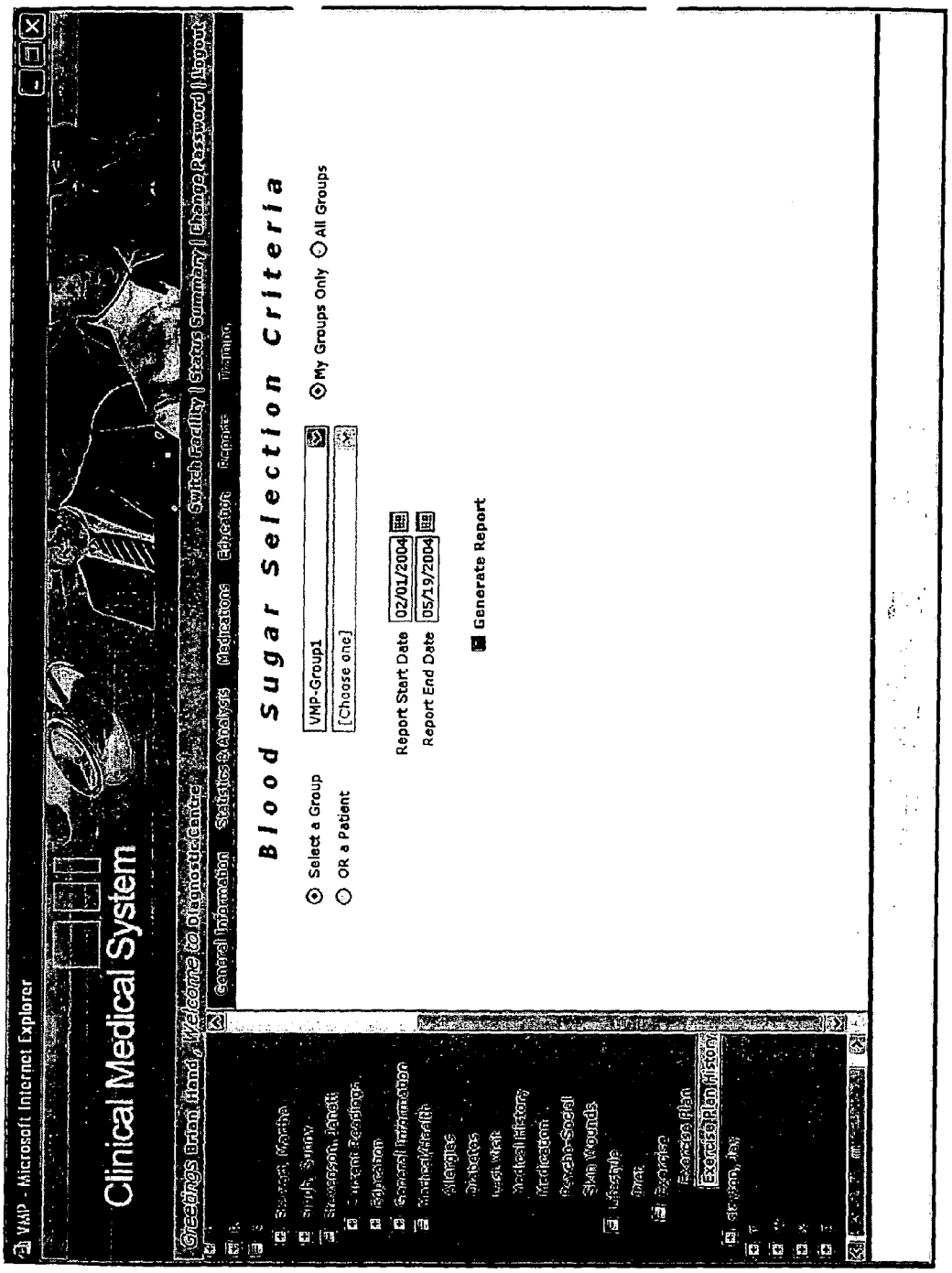
FIG. 38 is a blood sugar selection criteria report screen within the Reports group of the CMS.
Figure 39:
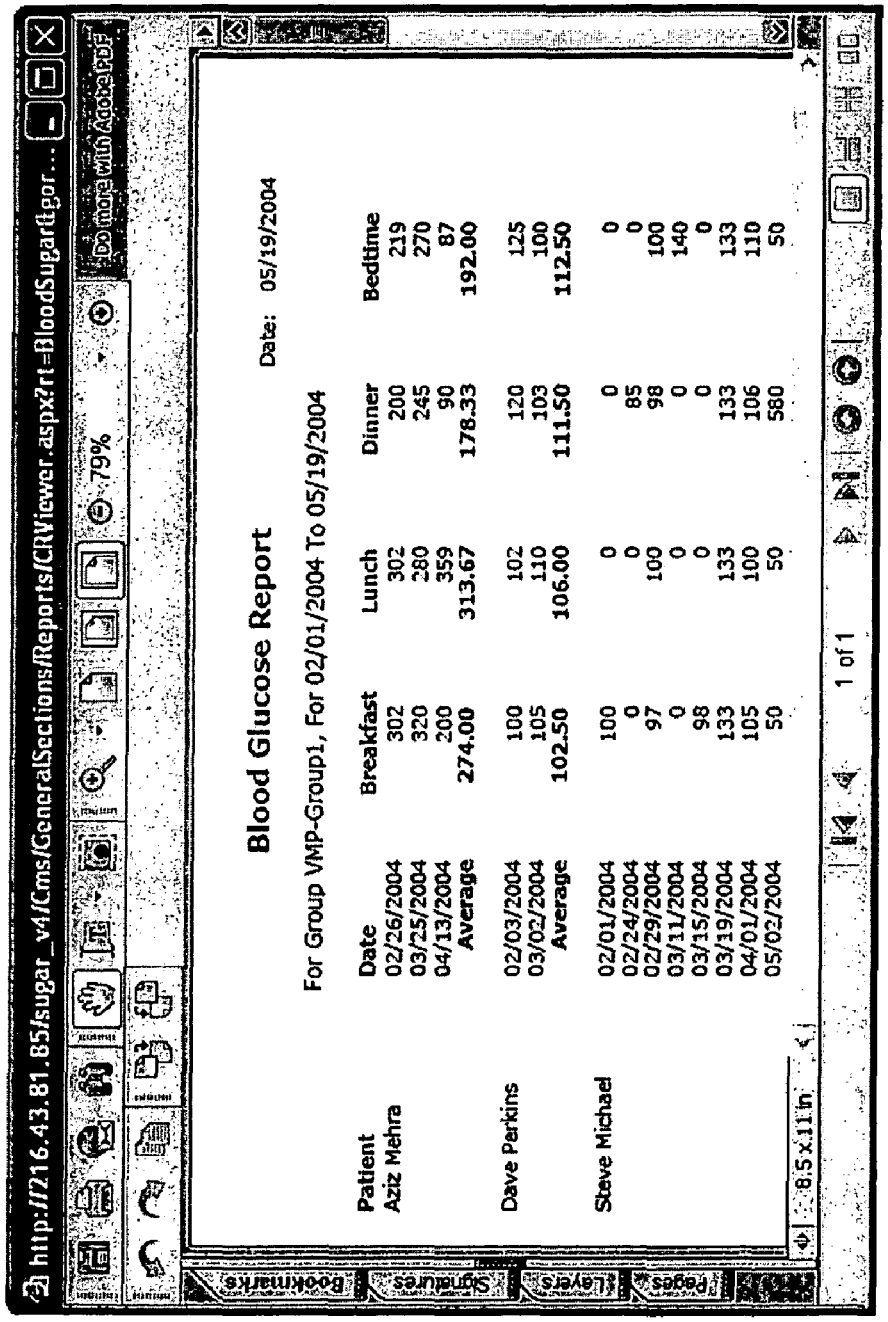
FIG. 39 is a blood glucose report screen within the Reports group.

Turning now to the fifth group of the Group Information, the Reports group allows users to select the type of report for viewing and printing such as blood sugar, blood pressure, HbA1C, lipid panel, kidney functions, weight/pulse/temperature/height, patient medications, quarterly diabetes patient summary and diabetes focused visits. Once a report is selected, a selection criteria screen will be provided. Four different criteria could be applied to each report including selecting a group of patients, selecting an individual patient, selecting a group of unassigned patients, and selecting a date range. See FIGS. 38 and 39 for exemplary screens.

Turning to the last group of the Group Information along the top axis, the Training group allows users to view individual training request lists, group training request lists, individual training reviews and group training reviews.

Administration

Figure 40A:
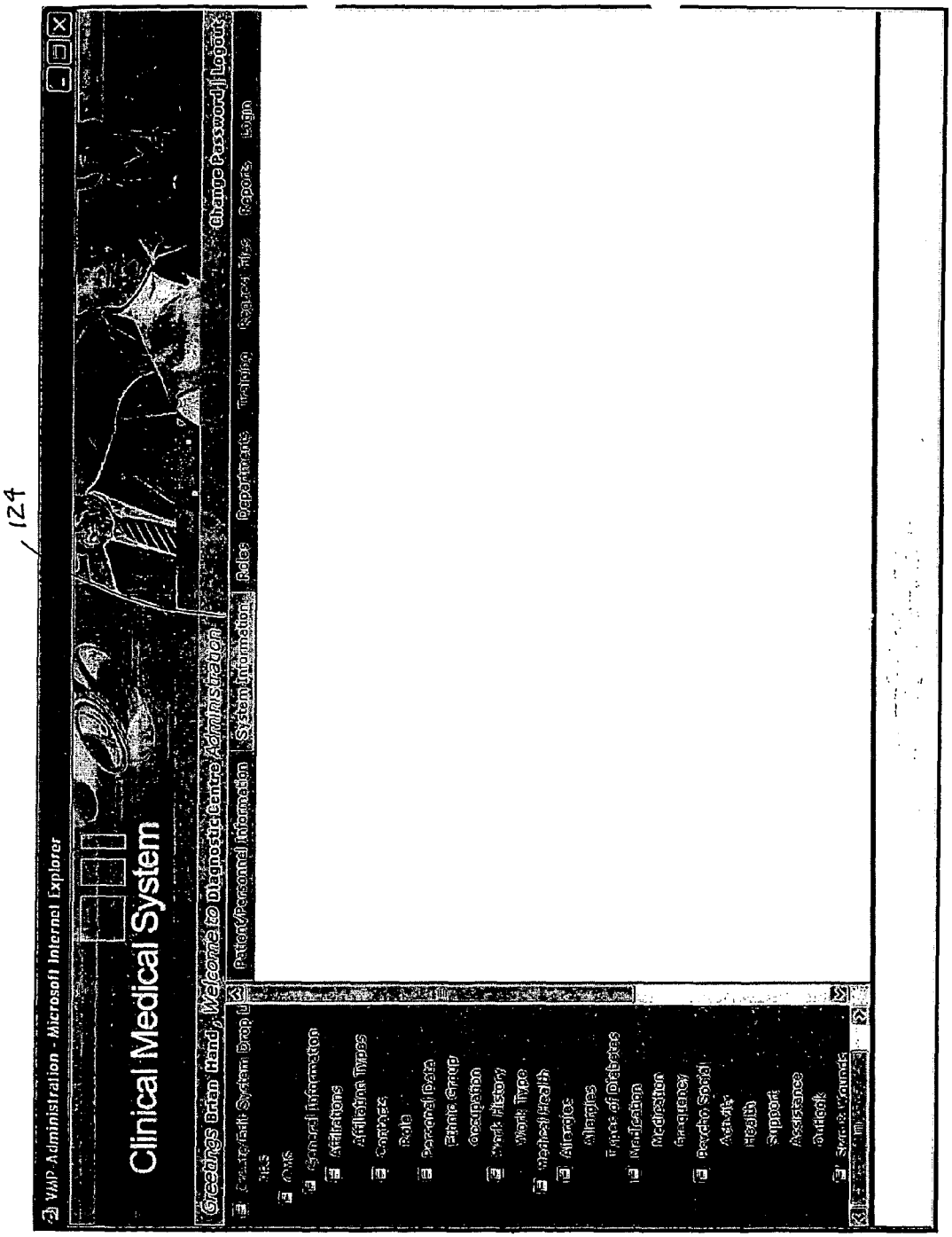
FIGS. 40A and 40B are main menu screens in an Administrator section in the CMS.
Figure 40B:
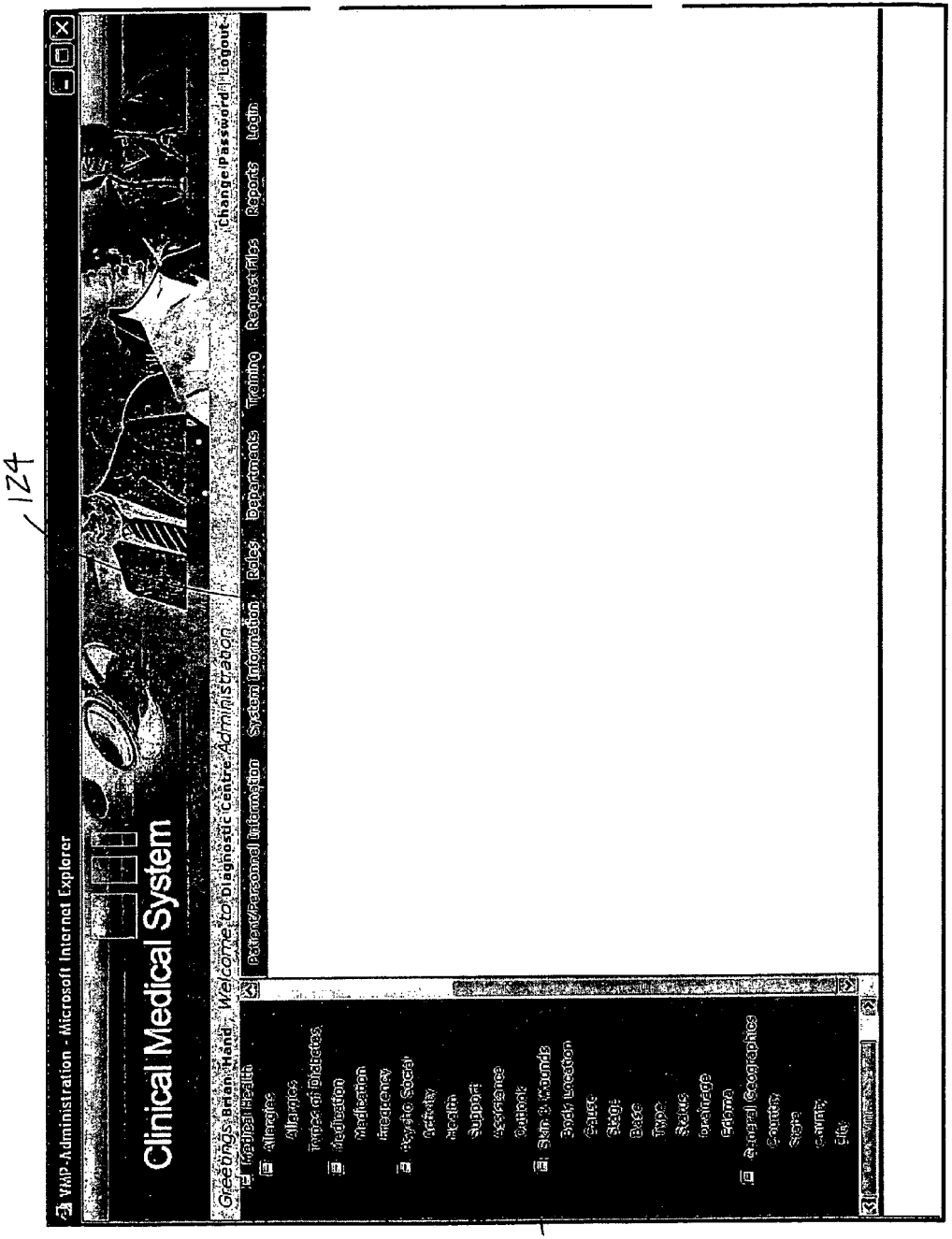

When a user logs in as an administrator, a main menu such as that set forth in FIGS. 40A and 40B is provided. Along a left column 122 is a navigation tree setting forth drop lists for the CMS for individual patient information. Along the top axis 124 is a menu of options such as Patient/Personal Information, System Information, Roles, Departments, Training, Request Files, Reports, and Login.

Figure 41:
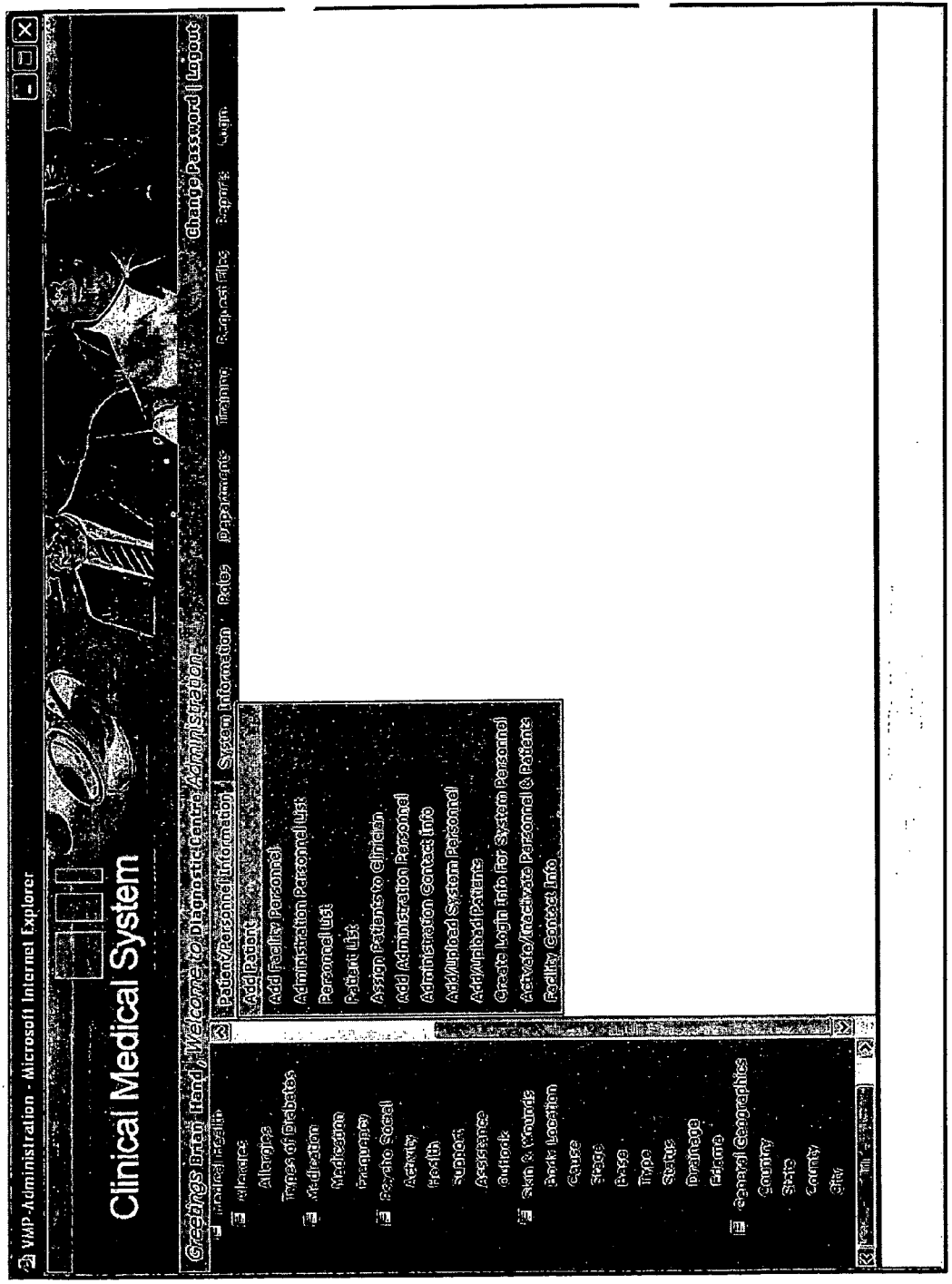
FIG. 41 is a Patient/Personnel Information pull down menu in the CMS.

Under the Patient/Personnel Information group, a pull down menu as shown in FIG. 41 includes the following sections: Add Patient, Add Facility Personnel, Administration Personnel List, Personnel List, Patient List, Assign Patients To Clinician, Add Administration Personnel, Administration Contact Info, Add/Upload System Personnel, Add/Upload Patients, Create Login Info For System Personnel, Activate/Inactivate Personnel & Patients, and Facility Contact Info.

Figure 42:
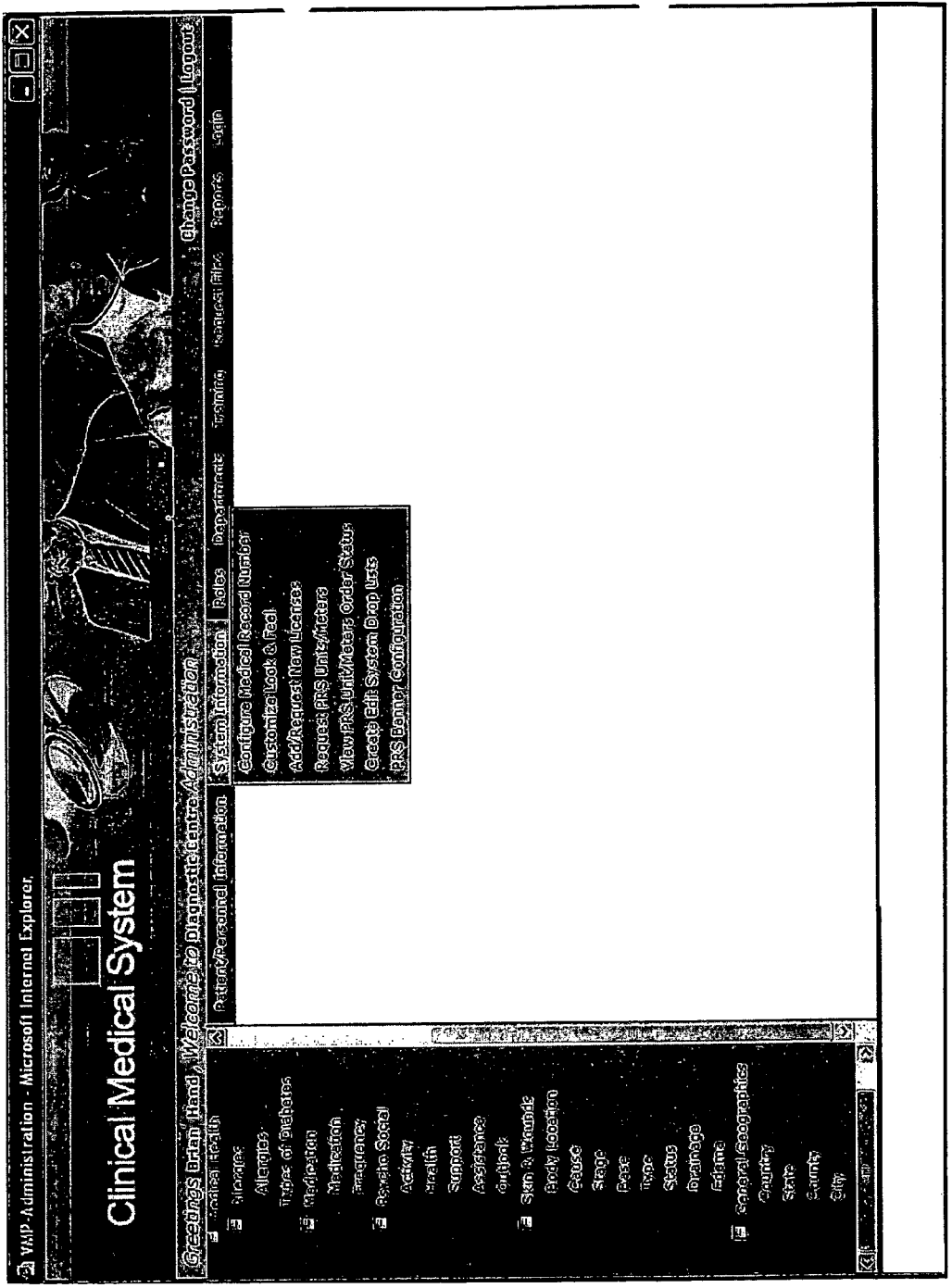
FIG. 42 is a System Information pull down menu in the CMS.

Under the System Information group, a pull down menu as shown in FIG. 42 includes the following sections: Configure Medical Records Number, Customize Look & Feel, Add/Request New Licenses, Request PRS Units/Meters, View PRS Units/Meters Order Status, Create Edit System Drop Lists, and PRS Banner Configuration.

Figure 43:
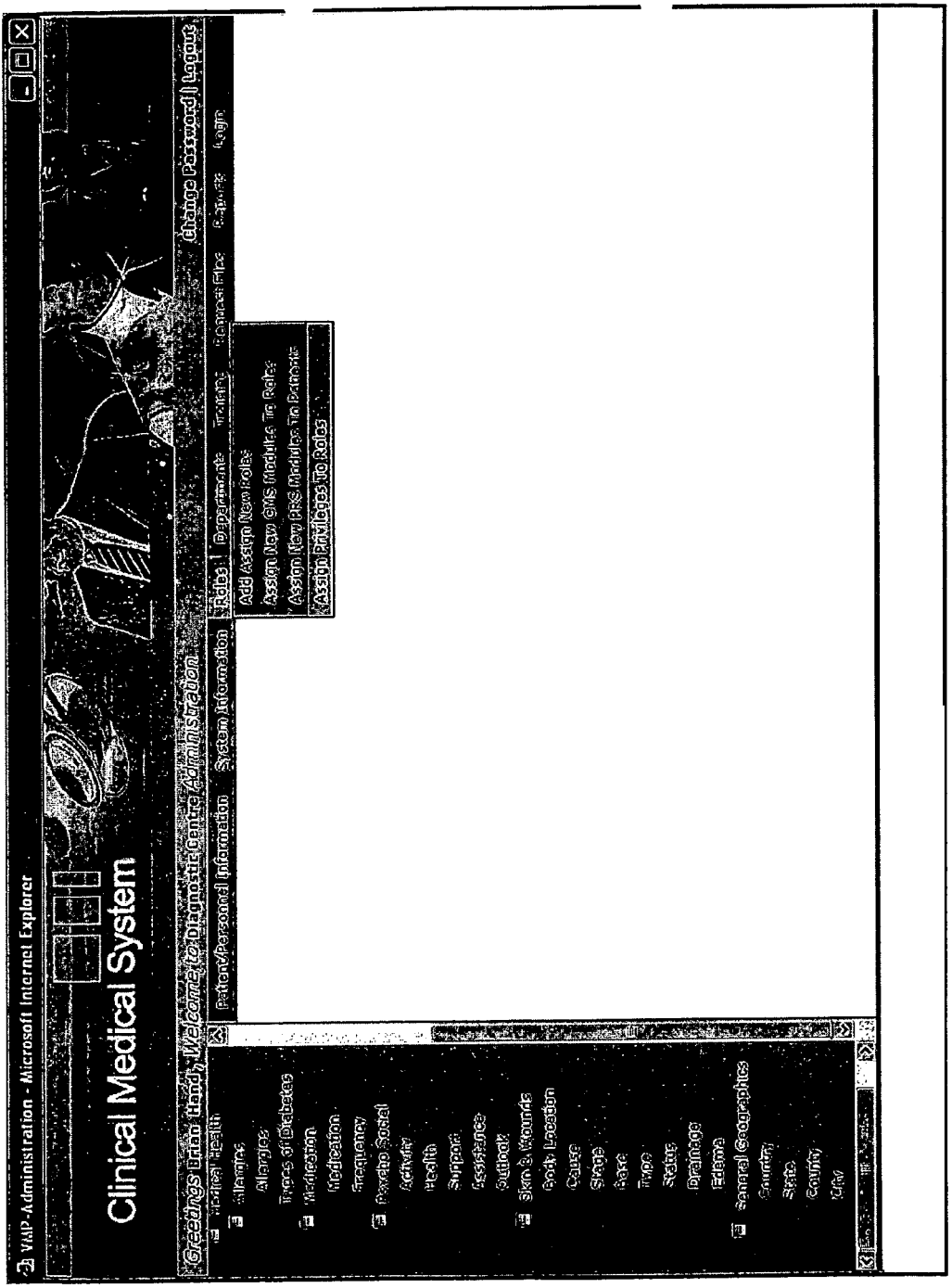
FIG. 43 is a Roles pull down menu in the CMS.

Under the Roles group, a pull down menu as shown in FIG. 43 includes the following options: Add Assign New Roles, Assign New CMS Modules To Roles, Assign New PRS Modules To Patients, and Assign Privileges To Roles.

Figure 44:
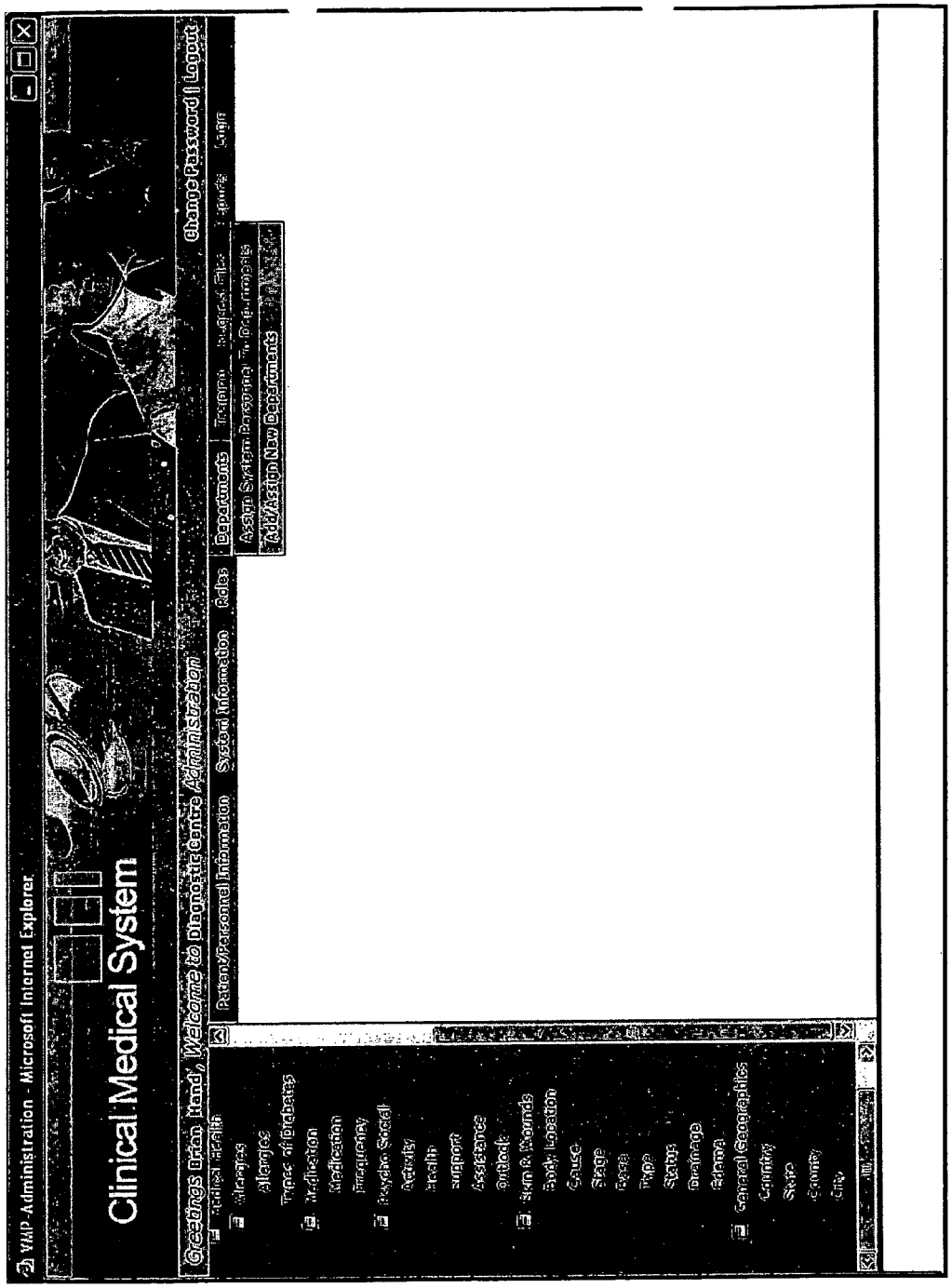
FIG. 44 is a Departments pull down menu in the CMS.

Under the Departments group, a pull down menu as shown in FIG. 44 includes the following section: Assign System Personnel To Departments and Add/Assign New Departments.

Figure 45:
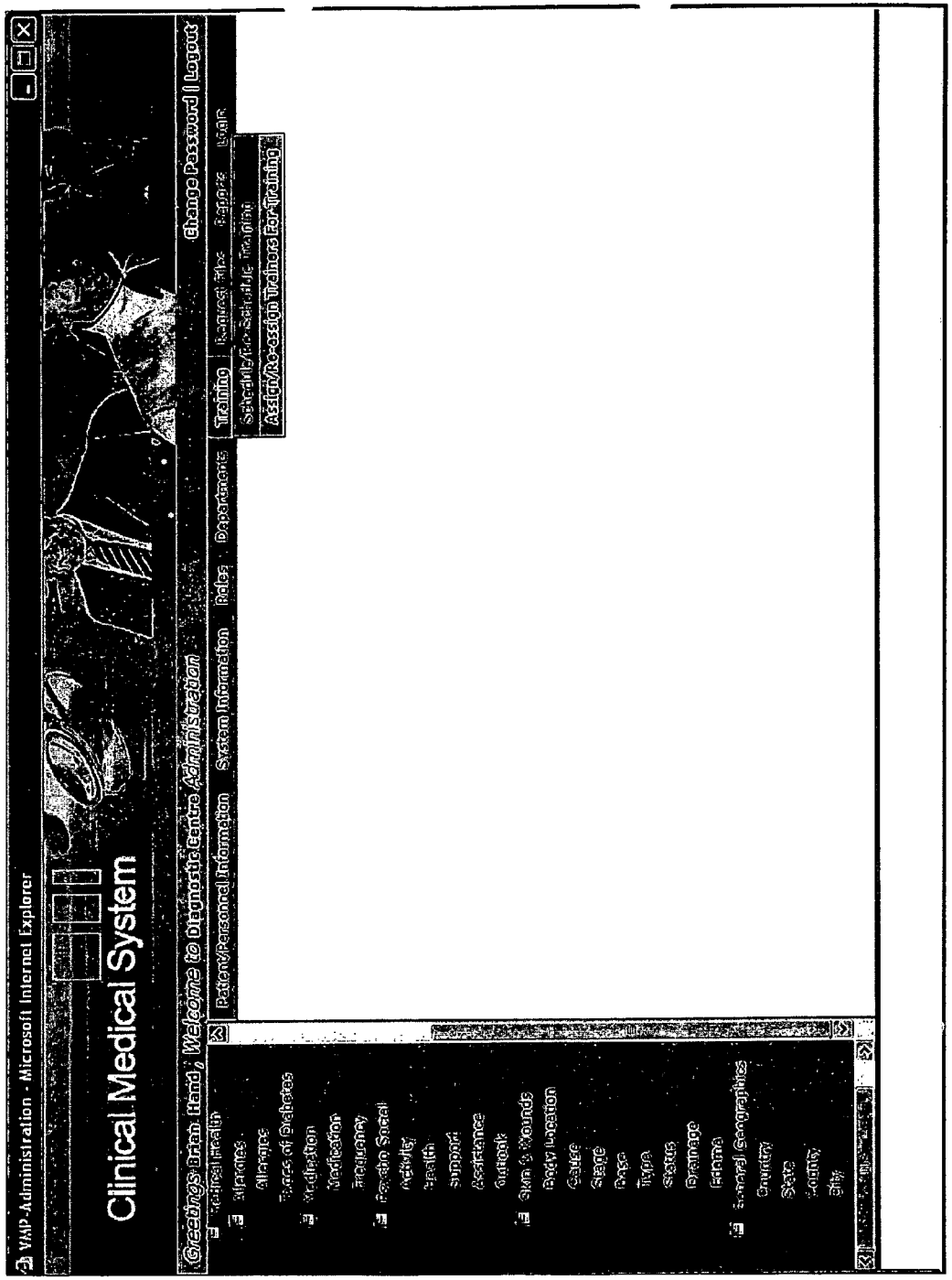
FIG. 45 is a Training pull down menu in the CMS.

Under the Training group, a pull down menu as shown in FIG. 45 includes the following section: Schedule/Re-schedule Training and Assign/Re-assign Trainers For Training.

Figure 46:
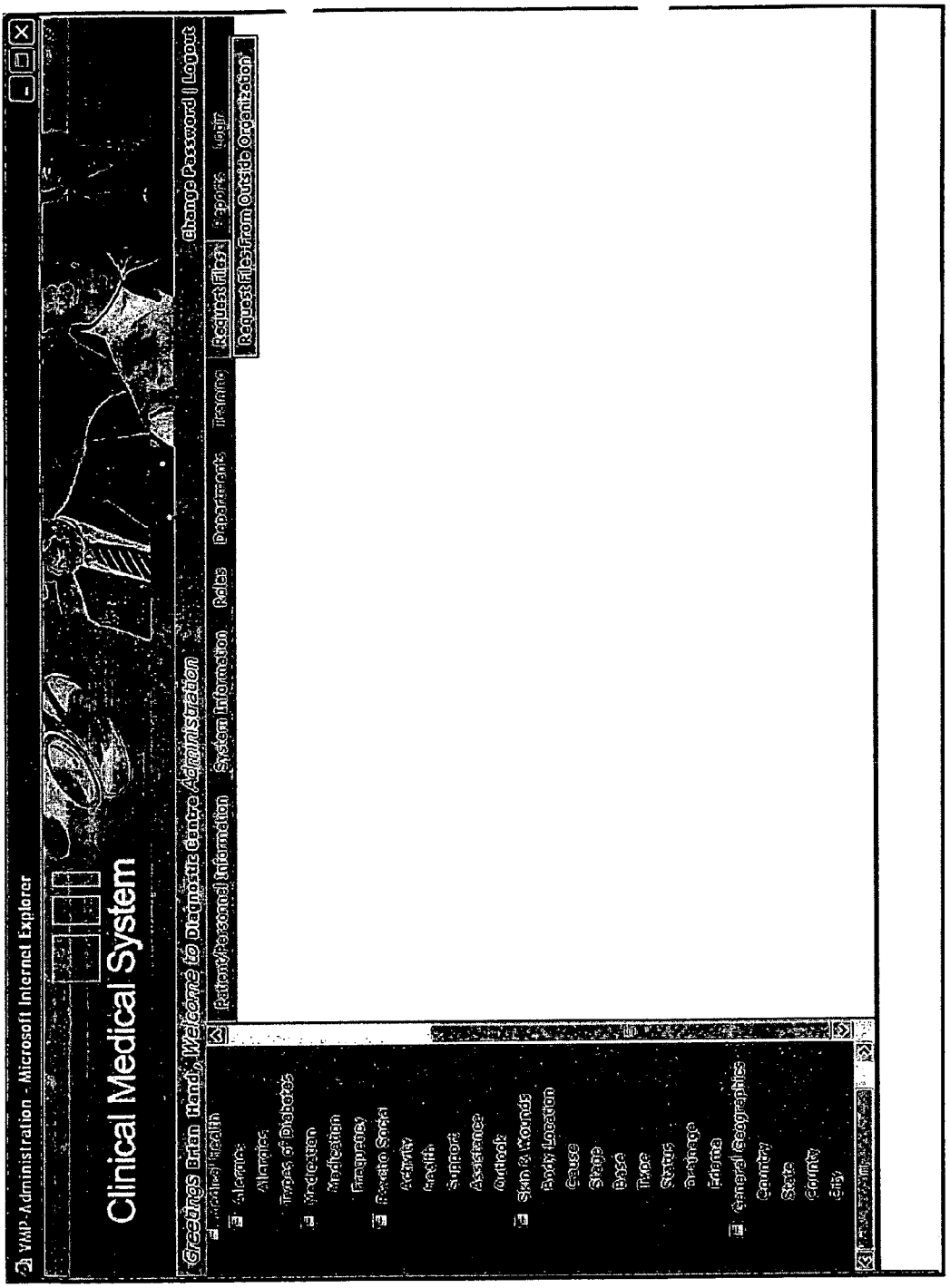
FIG. 46 is a Request Files pull down menu in the CMS.

Under the Request Files group, a pull down menu as shown in FIG. 46 includes the following section: Request Files From Outside Organization.

Figure 47:
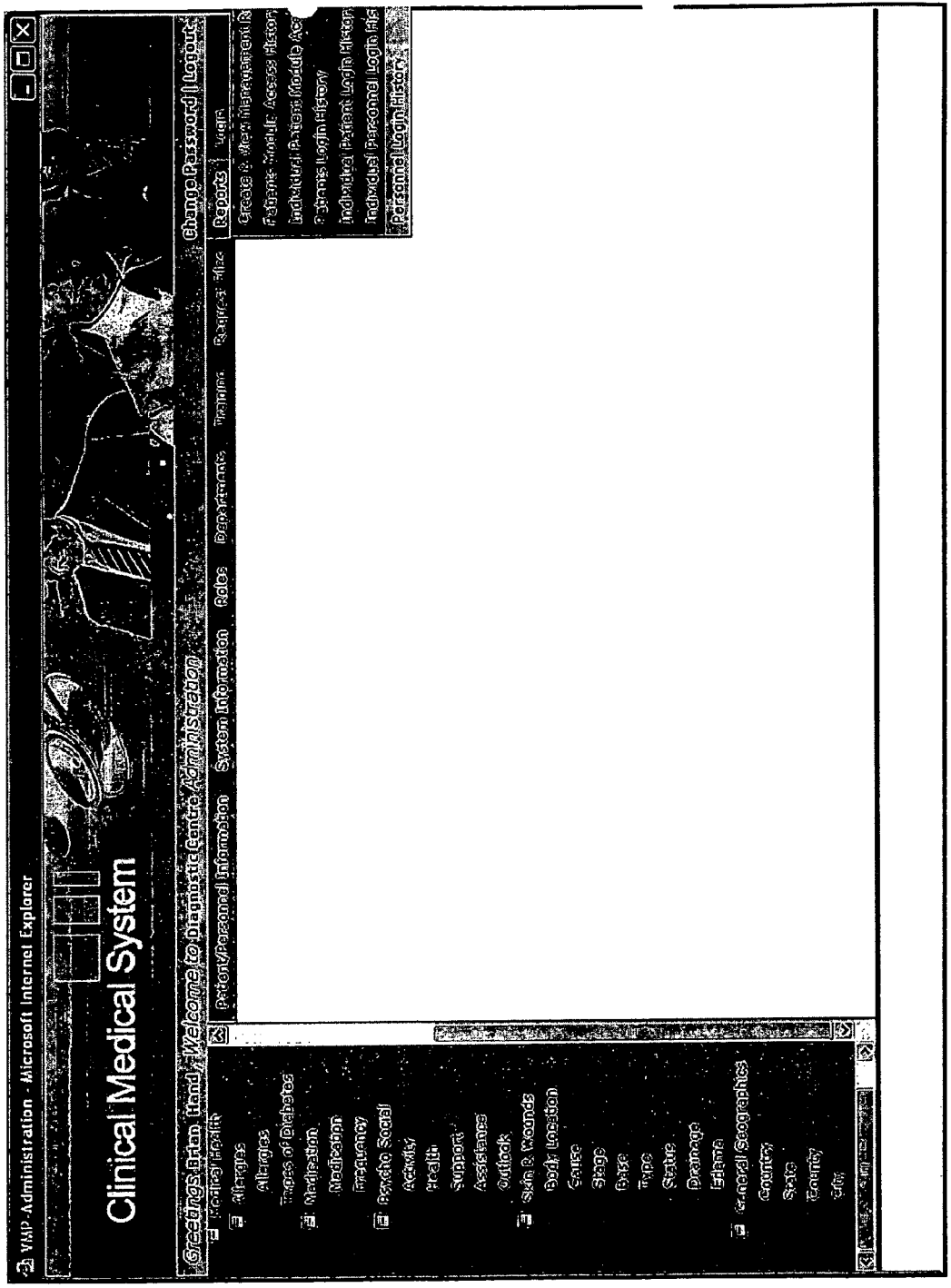
FIG. 47 is a Reports pull down menu in the CMS.

Under the Reports group, a pull down menu as shown in FIG. 47 includes the following section: Create & View Management Reports, Patients Module Access History, Individual Patient Module Access, Patients Login History, Individual Patient Login History, Individual Personnel Login History and Personnel Login History.

Figure 48:
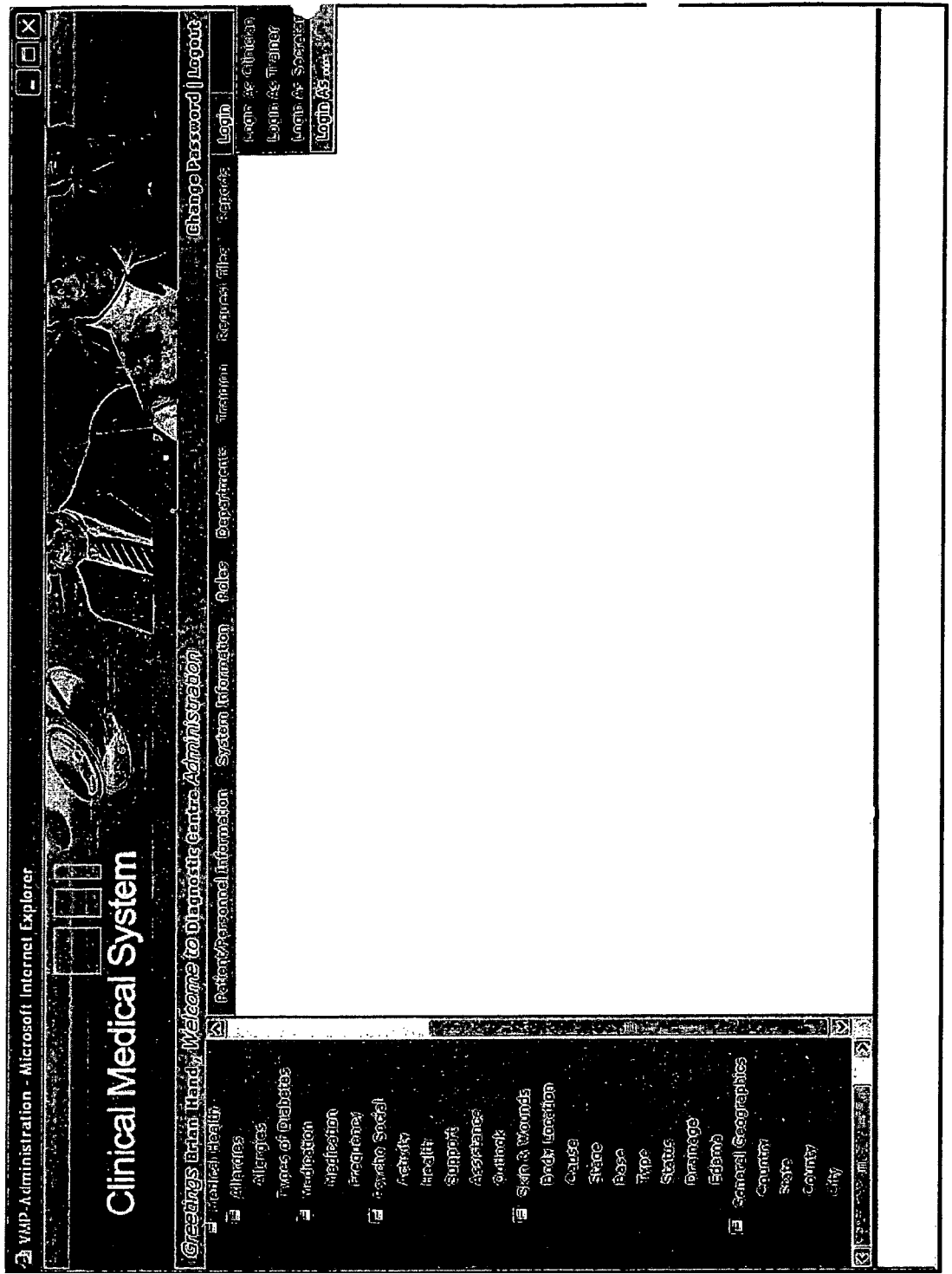
FIG. 48 is a Login pull down menu in the CMS.

Under the Login group, a pull down menu as shown in FIG. 48 includes the following sections: Login As Clinician, Login As Trainer, Login as Secretary and Login As . . . .

One role of an administrator is to create a medical records number. A medical records number needs to be assigned to every patient and is required for entering patient data information. With the CMS, automated generation of medical record numbers is setup as an administrator function. An administrator is able to automatically or manually generate a medical record number. If an administrator selects the automatic option, the administrator will be given three text boxes. The first text box is a prefix box, the second box is the starting medical record number box and third box is a suffix box. The prefix box is used to create a static prefix to a medical record number. The suffix box is used to create a static suffix to a medical record number. The starting medical record number box allows the administrator to enter a starting number that will be automatically incremented. In the automatic generation mode, a number that is generated is checked to make sure it does not already exists in the system.

If an administrator selects the manual option, each medical record number is entered manually. If the administrator enters a medical record number that already exists in the system, an error message is provided. The error message can contain the name of the patient who has the existing medical record number. If an administrator does not enter a medical records number and tries to save patient information, the system will provide an error message.

CMS Users

Users of the CMS 102 are organized into types or roles and can include the following types: general administrator, entity level administrator, facility level administrator, clinician, data entry personnel and trainer. Each type or role is described as below.

General Administrator. A General Administrator has full control and access to the CMS. A general administrator should have access and permission to configure, control and enable/disable CMS functionality. Following features can be made available to a general administrator within the CMS:
- Ability to have full control and access to the CMS
- Ability to setup HI-LO ranges for the graphs displayed in the Current Reading section
- Ability to assign permissions
- Ability to reset passwords
- Ability to activate/deactivate user accounts
- Ability to configure the system with clinicians and facilities
- Ability to perform system maintenance
- Ability to do audit log backups and purge audit logs
- Ability to deactivate knowledge base
- Ability to import educational content and knowledge base information
- Ability to provide automated deactivation of an inactive patient
- Ability to deactivate unassigned affiliations
- Ability to set up alerts for Administration
- Ability to set up alerts for a down system
- Ability to set up alerts upon hacking or multiple login tries
- Ability to generate system related reports, patient monitoring aging reports, hospital/medical facilities/clinics reports, affiliation/affiliation type reports, and audit log reports
- Ability to review information relating to allergies, clinicians, patients, diet plans, and exercise plans.

Entity Level Administrator. An entity level administrator can have the ability to add a new facility. A database check is performed when a new facility is entered to ensure that the facility is not a duplicate. Entities with multiple facilities have a drop list of all current facilities. New facility information can include facility name, location, and contact information.

Facility Level Administrator. A facility level administrator can have the ability to enter and edit new patients, clinicians, data entry personnel and trainers. A facility level administrator can have access to a user setup screen. The user set up screen consists of the following text fields: first name, last name, middle initial, social security number, city, state, zip code, telephone, fax, email, pager, and mobile. The user setup screen has a checkbox field for role (clinician, data entry, administrator, trainer, etc.) and a checkbox field for user status (active, inactive).

Clinicians. Clinicians using the CMS have access and permission to work with patient information and to access information that helps in treating a patient or a group of patients. The following features can be made available to clinicians using CMS: entering, editing and reviewing patient data and group data, reviewing and editing knowledge base, monitoring critical patient parameters and notifying correct authority for patient care, referring a patient to another clinician, identifying and taking action on feedback from patients on educational material, working with trainers to schedule reviews for patients, and identifying completed reviews.

Data Entry Personnel. Data entry personnel typically work for clinicians in entering patient data. A data entry user using the CMS should have access and permission to work with patient information for entering and editing purposes. Such a user would typically not have access to group information. The following abilities can be made available to a data entry user within the CMS: to enter/edit patient data, to enter/edit affiliations, to enter/edit educational programs, and to view information by entity or facility.

Trainers. Trainers typically work with patients in scheduling and monitoring educational programs. The following abilities can be made available to a trainer within the CMS: to monitor educational progress of individual patients, to suggest that a patient or a group needs educational review, to schedule classes for groups, to do time tracking for scheduled training sessions, to do attendance tracking for scheduled training sessions, to enter/add new manuals or teaching-related material, to run educational progress reports by patients, and to receive requests for training from a clinician for patient/group training through email or on login at the status screen.

Architecture

The system of the present invention can be packaged as an enterprise model or an ASP (Application Service Provider) model. The ASP model is a product distribution scheme involving a centralized host supporting users and requires additional database structures to accommodate the needs of vendor level administration screens, a front end portal (login) for customer access, a licensing system, data transfer formats to meet government and industry regulations (i.e., HL7 and HIPPA), customer account management, and reporting/viewing data across subscribers.

Figure 49:
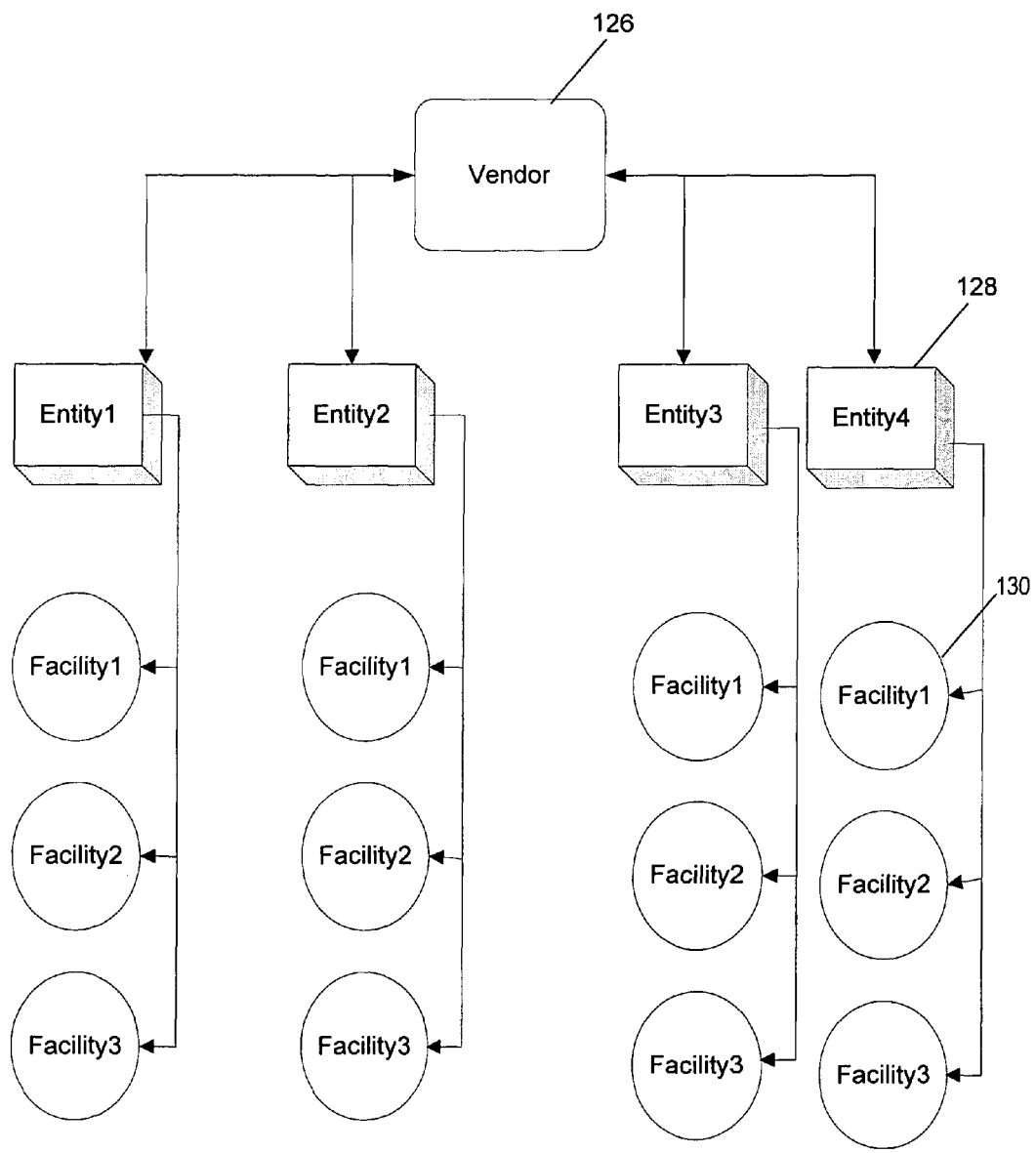
FIG. 49 is a schematic of an ASP architecture for the system.

With the ASP model and with reference to FIG. 49, the system includes three logical levels. At the top is a vendor level (ASP) 126 that sits on top of an entity level 128 that sits on top of a facilities level 130. Patient data is stored at the facility level in a separate database for each facility. Entity level databases store information regarding data relating to their facilities. A vendor database will store data relating to the various entities using the system as well as PRS unit data.

A Vendor Level Administrator can have access to the following functionality: ability to have super user privileges to use entity and facility administrator screens, ability to perform all user tasks at the facility level, ability to receive messaging from the PRS units in the form of pre-determined emails, and ability to receive notification from clinicians of a new patient request for a PRS account.

Other Modalities

The system was detailed above with respect to the chronic disease of diabetes. The PRS 100 and CMS 102 preferably allow multiple modalities to be worked together or separately. The PRS 100 and CMS 102 are designed to address other modalities such as hypertension, arthritis, kidney disease, and congestive heart failure.

A patient can be treated for the same chronic disease at two different facilities by the same clinician or by different clinicians. A patient can be treated for different conditions at two different facilities by the same clinician or by different clinicians. Using the system, a patient can see combined data from treatments at different facilities through one PRS login. A patient can use the same PRS 100 to view consolidated medical records across facilities. A clinician belonging to only one entity is able to view his/her patient records across facilities. A clinician treating a patient with different diseases at different facilities can view patient records across facilities. The same clinician treating patients with different diseases at different facilities can view records across facilities.

The invention claimed is:

1. A medical system comprising:
   a database of information relating to the management of a patient's disease including medical, education, exercise and diet information residing on a server computer;
   a patient component accessible by a patient and in communication with the database via a client computer comprising software to allow the patient access to their medical, education, diet and exercise information;
   a clinician component accessible by a clinician and in communication with the database to allow the clinician access to the patient's medical, education, diet and exercise information; and an interactive educational interactive component between the patient and the clinician comprising:
- a data store of the database comprising medical reading material;
- a selection of clinician assigned reading material selected from the medial reading material and specific to the patient or an attribute of the patient;
- a viewer for viewing the assigned reading material by the patient and indicating when such material has been read to the database; and
- a clinician alerter for providing the clinician with an indication that the patient has finished the reading assignment.

2. The medical system according to claim 1, further comprising:
- a patient alerter for providing the patient with an indication that the clinician has provided a further reading assignment.

3. The medical system according to claim 1, wherein the reading material also comprises a clinician assigned allotted time, and an alerter for alerting the clinician if the patient has not finished the reading material within the allotted time.

4. The medical system according to claim 1, wherein the assigned reading material is assigned by a plurality of trainers, and a trainer identifier is associated with each assigned reading material article.

5. The medical system according to claim 1, further comprising:
- an on-line chat utility permitting real-time communications between a clinician and a patient.

6. The medical system according to claim 1, further comprising:
- a tracker via which patients can input educational hours spent on a reading assignment, and clinicians can view individual and aggregate educational hours.

7. The medical system according to claim 1, further comprising:
- a scheduler that can be used by the clinician for scheduling the patient reading material and for taking action on education-related activities.

8. The medical system according to claim 1, wherein the reading material is designated as being for group training, individual training, or self training, wherein for the group training, the clinician identifies a trainer for conducting the group training, for the individual training, the clinician identifies a trainer for conducting the individual training, and for the self training, the clinician informs the patient through an element selected from the group consisting of a pager, telephone, e-mail, and patient residence system that a training has been assigned to them.

9. The medical system according to claim 1, further comprising:
- a feedback utility via which the patient can provide feedback to the clinician on the reading material.

* * * * *